United States Patent
Knoshaug et al.

(10) Patent No.: US 10,533,196 B2
(45) Date of Patent: Jan. 14, 2020

(54) XYLOSE UTILIZING OLEAGINOUS YEAST

(71) Applicant: Alliance for Sustainable Energy, LLC, Golden, CO (US)

(72) Inventors: Eric P. Knoshaug, Golden, CO (US); Min Zhang, Lakewood, CO (US); Arjun Singh, Lakewood, CO (US); Michael T. Guarnieri, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 406 days.

(21) Appl. No.: 15/282,591

(22) Filed: Sep. 30, 2016

(65) Prior Publication Data

US 2017/0088866 A1 Mar. 30, 2017

Related U.S. Application Data

(60) Provisional application No. 62/315,720, filed on Mar. 31, 2016, provisional application No. 62/235,057, filed on Sep. 30, 2015.

(51) Int. Cl.
| | |
|---|---|
| *C12P 7/64* | (2006.01) |
| *C12N 9/04* | (2006.01) |
| *C12N 9/12* | (2006.01) |
| *C07K 14/395* | (2006.01) |
| *C12N 9/10* | (2006.01) |
| *C12P 7/10* | (2006.01) |

(52) U.S. Cl.
CPC .......... *C12P 7/6436* (2013.01); *C07K 14/395* (2013.01); *C12N 9/0006* (2013.01); *C12N 9/1029* (2013.01); *C12N 9/12* (2013.01); *C12N 9/1205* (2013.01); *C12P 7/10* (2013.01); *C12Y 101/01009* (2013.01); *C12Y 101/01307* (2013.01); *C12Y 203/0102* (2013.01); *C12Y 207/01017* (2013.01); *C12Y 207/11001* (2013.01); *Y02E 50/16* (2013.01); *Y02E 50/17* (2013.01)

(58) Field of Classification Search
None
See application file for complete search history.

(56) References Cited

FOREIGN PATENT DOCUMENTS

WO WO-20111/131667 A1 * 10/2011

OTHER PUBLICATIONS

Eliaasson et al. Anaerobic xylose fermentation by recombinant *Saccharomyces cerevisiae* carrying XYL1, XYL2 and XKS1 in mineral medium chemostat cultures. Appl and Environ Microbiol, 2000, 66(8): 3381-3386.*
Seip et al. Snf1 Is a Regulator of Lipid Accumulation in *Yarrowia lipolytica*. Appl and Environ Microbiol, 2013, 79(23): 73607370.*
Kamisaka et al. Overexpression of the active diacylglycerol acyltransferase variants transforms *Saccharomyces cerevisiae* into an oleaginous yeast. App Microbiol Biotechnol (2013), 97: 7345-7355.*
Hickman et al. The Hog1 mitogen-activated protein kinase mediates a hypoxic response in *Saccharomyces cerevisiae*. Genetics 188: 325-338, 2011.*
Knoshaug et al., "A xylose-utilizing oleaginous *Saccharomyces cerevisiae* and a rapid near-infrared scanning methodology for lipids", Poster Session 2, Society for Industrial Microbiology & Biotechnology, Aug. 2-6, 2015, Philadelphia, PA, available at https://sim.confex.com/sim/2015/webprogram/Paper30539.html, accessed Sep. 19, 2016, p. 1.

* cited by examiner

*Primary Examiner* — Iqbal H Chowdhury
(74) *Attorney, Agent, or Firm* — Sam J. Barkley; John C. Stolpa

(57) ABSTRACT

Presented herein are oleaginous strains of yeast such as *Saccharomyces cerevisiae* that have been modified to allow for xylose utilization. Such strains are also modified to allow for higher lipid accumulation utilizing a broad range of sugar monomers such as those released during pretreatment and enzymatic saccharification of lignocellulosic biomass. Methods of producing lipids and ethanol using these yeast strains are also disclosed.

22 Claims, 23 Drawing Sheets

Specification includes a Sequence Listing.

ATGCCTTCTATTAAGTTGAACTCTGGTTACGACATGCCAGCCGTCGGTTTCGGCTGTTGGAA
AGTCGACGTCGACACCTGTTCTGAACAGATCTACCGTGCTATCAAGACCGGTTACAGATTGT
TCGACGGTGCCGAAGATTACGCCAACGAAAAGTTAGTTGGTGCCGGTGTCAAGAAGGCCATT
GACGAAGGTATCGTCAAGCGTGAAGACTTGTTCCTTACCTCCAAGTTGTGGAACAACTACCA
CCACCCAGACAACGTCGAAAAGGCCTTGAACAGAACCCTTTCTGACTTGCAAGTTGACTACG
TTGACTTGTTCTTGATCCACTTCCCAGTCACCTTCAAGTTCGTTCCATTAGAAGAAAAGTAC
CCACCAGGATTCTACTGTGGTAAGGGTGACAACTTCGACTACGAAGATGTTCCAATTTTAGA
GACCTGGAAGGCTCTTGAAAAGTTGGTCAAGGCCGGTAAGATCAGATCTATCGGTGTTTCTA
ACTTCCCAGGTGCTTTGCTCTTGGACTTGTTGAGAGGTGCTACCATCAAGCCATCTGTCTTG
CAAGTTGAACACCACCCATACTTGCAACAACCAAGATTGATCGAATTCGCTCAATCCCGTGG
TATTGCTGTCACCGCTTACTCTTCGTTCGGTCCTCAATCTTTCGTTGAATTGAACCAAGGTA
GAGCTTTGAACACTTCTCCATTGTTCGAGAACGAAACTATCAAGGCTATCGCTGCTAAGCAC
GGTAAGTCTCCAGCTCAAGTCTTGTTGAGATGGTCTTCCCAAAGAGGCATTGCCATCATTCC
AAAGTCCAACACTGTCCCAAGATTGTTGGAAAACAAGGACGTCAACAGCTTCGACTTGGACG
AACAAGATTTCGCTGACATTGCCAAGTTGGACATCAACTTGAGATTCAACGACCCATGGGAC
TGGGACAAGATTCCTATCTTCGTC

B.

MPSIKLNSGYDMPAVGFGCWKVDVDTCSEQIYRAIKTGYRLFDGAEDYANEKLVGAGVKKAI
DEGIVKREDLFLTSKLWNNYHHPDNVEKALNRTLSDLQVDYVDLFLIHFPVTFKFVPLEEKY
PPGFYCGKGDNFDYEDVPILETWKALEKLVKAGKIRSIGVSNFPGALLLDLLRGATIKPSVL
QVEHHPYLQQPRLIEFAQSRGIAVTAYSSFGPQSFVELNQGRALNTSPLFENETIKAIAAKH
GKSPAQVLLRWSSQRGIAIIPKSNTVPRLLENKDVNSFDLDEQDFADIAKLDINLRFNDPWD
WDKIPIFV

```
ATGACTGCTAACCCTTCCTTGGTGTTGAACAAGATCGACGACATTTCGTTCGAAACTTACGA
TGCCCCAGAAATCTCTGAACCTACCGATGTCCTCGTCCAGGTCAAGAAAACCGGTATCTGTG
GTTCCGACATCCACTTCTACGCCCATGGTAGAATCGGTAACTTCGTTTTGACCAAGCCAATG
GTCTTGGGTCACGAATCCGCCGGTACTGTTGTCCAGGTTGGTAAGGGTGTCACCTCTCTTAA
GGTTGGTGACAACGTCGCTATCGAACCAGGTATTCCATCCAGATTCTCCGACGAATACAAGA
GCGGTCACTACAACTTGTGTCCTCACATGGCCTTCGCCGCTACTCCAACTCCAAGGAAGGC
GAACCAAACCCACCAGGTACCTTATGTAAGTACTTCAAGTCGCCAGAAGACTTCTTGGTCAA
GTTGCCAGACCACGTCAGCTTGGAACTCGGTGCTCTTGTTGAGCCATTGTCTGTTGGTGTCC
ACGCCTCTAAGTTGGGTTCCGTTGCTTTCGGCGACTACGTTGCCGTCTTTGGTGCTGGTCCT
GTTGGTCTTTTGGCTGCTGCTGTCGCCAAGACCTTCGGTGCTAAGGGTGTCATCGTCGTTGA
CATTTTCGACAACAAGTTGAAGATGGCCAAGGACATTGGTGCTGCTACTCACACCTTCAACT
CCAAGACCGGTGGTTCTGAAGAATTGATCAAGGCTTTCGGTGGTAACGTGCCAAACGTCGTT
TTGGAATGTACTGGTGCTGAACCTTGTATCAAGTTGGGTGTTGACGCCATTGCCCCAGGTGG
TCGTTTCGTTCAAGTCGGTAACGCTGCTGGTCCAGTCAGCTTCCCAATCACCGTTTTCGCCA
TGAAGGAATTGACTTTGTTCGGTTCTTTCAGATACGGATTCAACGACTACAAGACTGCTGTT
GGAATCTTTGACACTAACTACCAAAACGGTAGAGAAATGCTCCAATTGACTTTGAACAATT
GATCACCCACAGATACAAGTTCAAGGACGCTATTGAAGCCTACGACTTGGTCAGAGCCGGTA
AGGGTGCTGTCAAGTGTCTCATTGACGGCCCTGAG
```

B.

```
MTANPSLVLNKIDDISFETYDAPEISEPTDVLVQVKKTGICGSDIHFYAHGRIGNFVLTKPM
VLGHESAGTVVQVGKGVTSLKVGDNVAIEPGIPSRFSDEYKSGHYNLCPHMAFAATPNSKEG
EPNPPGTLCKYFKSPEDFLVKLPDHVSLELGALVEPLSVGVHASKLGSVAFGDYVAVFGAGP
VGLLAAAVAKTFGAKGVIVVDIFDNKLKMAKDIGAATHTFNSKTGGSEELIKAFGGNVPNVV
LECTGAEPCIKLGVDAIAPGGRFVQVGNAAGPVSFPITVFAMKELTLFGSFRYGFNDYKTAV
GIFDTNYQNGRENAPIDFEQLITHRYKFKDAIEAYDLVRAGKGAVKCLIDGPE
```

ATGTTGTGTTCAGTAATTCAGAGACAGACAAGAGAGGTTTCCAACACAATGTCTTTAGACTC
ATACTATCTTGGGTTTGATCTTTCGACCCAACAACTGAAATGTCTCGCCATTAACCAGGACC
TAAAAATTGTCCATTCAGAAACAGTGGAATTTGAAAAGGATCTTCCGCATTATCACACAAAG
AAGGGTGTCTATATACACGGCGACACTATCGAATGTCCCGTAGCCATGTGGTTAGAGGCTCT
AGATCTGGTTCTCTCGAAATATCGCGAGGCTAAATTTCCATTGAACAAAGTTATGGCCGTCT
CAGGGTCCTGCCAGCAGCACGGGTCTGTCTACTGGTCCTCCCAAGCCGAATCTCTGTTAGAG
CAATTGAATAAGAAACCGGAAAAGATTTATTGCACTACGTGAGCTCTGTAGCATTTGCAAG
GCAAACCGCCCCCAATTGGCAAGACCACAGTACTGCAAAGCAATGTCAAGAGTTTGAAGAGT
GCATAGGTGGGCCTGAAAAATGGCTCAATTAACAGGGTCCAGAGCCCATTTTAGATTTACT
GGTCCTCAAATTCTGAAAATTGCACAATTAGAACCAGAAGCTTACGAAAAAACAAAGACCAT
TTCTTTAGTGTCTAATTTTTTGACTTCTATCTTAGTGGGCCATCTTGTTGAATTAGAGGAGG
CAGATGCCTGTGGTATGAACCTTTATGATATACGTGAAAGAAAATTCAGTGATGAGCTACTA
CATCTAATTGATAGTTCTTCTAAGGATAAAACTATCAGACAAAAATTAATGAGAGCACCCAT
GAAAAATTTGATAGCGGGTACCATCTGTAAATATTTTATTGAGAAGTACGGTTTCAATACAA
ACTGCAAGGTCTCTCCCATGACTGGGGATAATTTAGCCACTATATGTTCTTTACCCCTGCGG
AAGAATGACGTTCTCGTTTCCCTAGGAACAAGTACTACAGTTCTTCTGGTCACCGATAAGTA
TCACCCCTCTCCGAACTATCATCTTTTCATTCATCCAACTCTGCCAAACCATTATATGGGTA
TGATTTGTTATTGTAATGGTTCTTTGGCAAGGGAGAGGATAAGAGACGAGTTAAACAAAGAA
CGGGAAAATAATTATGAGAAGACTAACGATTGGACTCTTTTTAATCAAGCTGTGCTAGATGA
CTCAGAAAGTAGTGAAATGAATTAGGTGTATATTTTCCTCTGGGGGAGATCGTTCCTAGCG
TAAAAGCCATAAACAAAGGGTTATCTTCAATCCAAAAACGGGTATGATTGAAAGAGAGGTG
GCCAAGTTCAAAGACAAGAGGCACGATGCCAAAAATATTGTAGAATCACAGGCTTTAAGTTG
CAGGGTAAGAATATCTCCCCTGCTTTCGGATTCAAACGCAAGCTCACAACAGAGACTGAACG
AAGATACAATCGTGAAGTTTGATTACGATGAATCTCCGCTGCGGGACTACCTAAATAAAAGG
CCAGAAAGGACTTTTTTTGTAGGTGGGGCTTCTAAAAACGATGCTATTGTGAAGAAGTTTGC
TCAAGTCATTGGTGCTACAAAGGGTAATTTTAGGCTAGAAACACCAAACTCATGTGCCCTTG
GTGGTTGTTATAAGGCCATGTGGTCATTGTTATATGACTCTAATAAAATTGCAGTTCCTTTT
GATAAATTTCTGAATGACAATTTTCCATGGCATGTAATGGAAAGCATATCCGATGTGGATAA
TGAAAATTGGGATCGCTATAATTCCAAGATTGTCCCCTTAAGCGAACTGGAAAAGACTCTCA
TC

B.

MLCSVIQRQTREVSNTMSLDSYYLGFDLSTQQLKCLAINQDLKIVHSETVEFEKDLPHYHTK
KGVYIHGDTIECPVAMWLEALDLVLSKYREAKFPLNKVMAVSGSCQQHGSVYWSSQAESLLE
QLNKKPEKDLLHYVSSVAFARQTAPNWQDHSTAKQCQEFEECIGGPEKMAQLTGSRAHFRFT
GPQILKIAQLEPEAYEKTKTISLVSNFLTSILVGHLVELEEADACGMNLYDIRERKFSDELL
HLIDSSSKDKTIRQKLMRAPMKNLIAGTICKYFIEKYGFNTNCKVSPMTGDNLATICSLPLR
KNDVLVSLGTSTTVLLVTDKYHPSPNYHLFIHPTLPNYMGMICYCNGSLARERIRDELNKE
RENNYEKTNDWTLFNQAVLDDSESSENELGVYFPLGEIVPSVKAINKRVIFNPKTGMIEREV
AKFKDKRHDAKNIVESQALSCRVRISPLLSDSNASSQQRLNEDTIVKFDYDESPLRDYLNKR
PERTFFVGGASKNDAIVKKFAQVIGATKGNFRLETPNSCALGGCYKAMWSLLYDSNKIAVPF
DKFLNDNFPWHVMESISDVDNENWDRYNSKIVPLSELEKTLI

ATGAGCAGTAACAACAACACAAACACAGCACCTGCCAATGCAAATTCTAGCCACCACCACCACCATCA
CCACCATCACCACCACCATCACGGTCATGGCGGAAGCAACTCGACGCTAAACAATCCCAAGTCGTCCT
TAGCGGATGGTGCACATATCGGGAACTACCAAATCGTCAAAACGCTGGGAGAGGGGTCCTTTGGTAAA
GTTAAATTGGCATATCATACCACTACGGGCCAAAAGTTGCTCTAAAAATCATTAATAAGAAGGTTTT
GGCAAAGAGTGATATGCAGGGCAGAATTGAAAGAGAAATATCTTATCTGAGACTCTTAAGACACCCC
ACATCATCAAACTGTATGATGTTATCAAATCCAAAGATGAAATCATTATGGTTATAGAGTACGCCGGG
AACGAATTGTTTGACTATATTGTTCAGAGAGACAAAATGAGCGAGCAAGAGGCAAGAAGATTTTTCCA
GCAGATCATCAGTGCCGTCGAGTACTGCCATAGGCACAAAATTGTCCATAGAGATCTGAAGCCTGAAA
ACTTACTACTAGATGAGCATCTGAATGTAAAGATTGCCGATTTTGGTTTGTCAAACATCATGACTGAT
GGTAATTTCTTAAAGACTTCTTGTGGTTCTCCCAATTATGCGGCTCCTGAAGTTATCAGCGGTAAGCT
GTACGCAGGCCCAGAAGTGGACGTGTGGTCATGTGGGGTTATCCTTTATGTTATGCTTTGTCGTCGTC
TACCGTTTGACGATGAAAGCATCCCAGTGCTTTTCAAGAATATCAGCAACGGTGTTTACACCTTGCCT
AAATTTTTATCTCCTGGAGCTGCTGGGCTAATCAAAAGAATGTTAATCGTTAATCCATTGAACAGAAT
AAGCATTCATGAAATTATGCAAGACGATTGGTTCAAAGTTGACCTGCCAGAATATCTACTTCCACCAG
ATTTGAAACCACACCCAGAAGAAGAGAATGAAAATAATGACTCAAAAAAGGATGGCAGCAGCCCAGAT
AACGATGAAATTGATGACAACCTTGTCAATATTTTATCATCGACCATGGGTTACGAAAAGACGAGAT
TTATGAGTCCTTAGAATCATCAGAAGACACTCCTGCATTCAACGAAATTAGGGACGCGTACATGTTGA
TTAAGGAGAATAAATCTTTGATCAAGGATATGAAGGCAAACAAAAGCGTCAGTGATGAACTGGATACC
TTTCTGTCCCAGTCACCTCCAACTTTTCAACAACAAAGCAAATCCCATCAAAAGAGTCAAGTAGATCA
TGAAACTGCCAAGCAACACGCAAGAAGGATGGCAAGTGCTATCACTCAACAAAGGACATATCACCAAT
CACCCTTCATGGATCAGTATAAAGAAGAAGACTCTACAGTTTCCATTTTGCCTACATCTTTACCTCAG
ATCCACAGAGCTAATATGTTAGCACAAGGTTCGCCAGCTGCCTCTAAAATATCTCCTCTTGTAACGAA
AAAATCTAAAACGAGATGGCATTTTGGTATACGATCTCGCTCATATCCATTAGACGTTATGGGTGAAA
TTTATATTGCCTTGAAGAATTTGGGTGCCGAATGGGCCAAGCCATCTGAAGAGGATTTATGGACTATC
AAATTAAGGTGGAAATATGATATTGGAAACAAGACAAACACTAATGAAAAATACCTGATTTAATGAA
AATGGTAATTCAATTATTTCAAATTGAAACCAATAATTATTTGGTGGATTTCAAATTTGACGGCTGGG
AAAGTAGTTATGGAGATGATACTACTGTTTCTAATATTTCTGAAGATGAAATGAGTACTTTTTCAGCC
TACCCATTTTTACATTTAACAACAAAACTAATTATGGAATTAGCCGTTAACAGTCAAAGCAAT

B.

MSSNNNTNTAPANANSSHHHHHHHHHHHHHGHGGSNSTLNNPKSSLADGAHIGNYQIVKTLGEGSFGK
VKLAYHTTTGQKVALKIINKKVLAKSDMQGRIEREISYLRLLRHPHIIKLYDVIKSKDEIIMVIEYAG
NELFDYIVQRDKMSEQEARRFFQQIISAVEYCHRHKIVHRDLKPENLLLDEHLNVKIADFGLSNIMTD
GNFLKTSCGSPNYAAPEVISGKLYAGPEVDVWSCGVILYVMLCRRLPFDDESIPVLFKNISNGVYTLP
KFLSPGAAGLIKRMLIVNPLNRISIHEIMQDDWFKVDLPEYLLPPDLKPHPEEENENNDSKKDGSSPD
NDEIDDNLVNILSSTMGYEKDEIYESLESSEDTPAFNEIRDAYMLIKENKSLIKDMKANKSVSDELDT
FLSQSPPTFQQQSKSHQKSQVDHETAKQHARRMASAITQQRTYHQSPFMDQYKEEDSTVSILPTSLPQ
IHRANMLAQGSPAASKISPLVTKKSKTRWHFGIRSRSYPLDVMGEIYIALKNLGAEWAKPSEEDLWTI
KLRWKYDIGNKTNTNEKIPDLMKMVIQLFQIETNNYLVDFKFDGWESSYGDDTTVSNISEDEMSTFSA
YPFLHLTTKLIMELAVNSQSN

```
ATGCGATTTGGCCTGCCATCAAAATTGGAACTCACTCCTCCGTTTAGGATAGGCATCCGAACTCAACTAACGGCA
CTAGTTAGTATAGTGGCTTTGGGCTCACTGATTATTCTGGCTGTAACGACAGGGGTCTATTTTACCTCGAACTAT
AAAAATTTAAGGTCCGATAGACTGTACATTGCCGCTCAGTTAAAGTCATCACAGATTGACCAAACTCTAAACTAC
TTATATTACCAGGCGTACTATTTGGCATCAAGAGACGCCCTGCAAAGCTCACTAACAAGTTACGTTGCAGGTAAC
AAGAGTGCAGATAATTGGGTAGATTCCTTGAGTGTGATTCAAAAATTTTTGAGCTCTTCAAACTTGTTTTATGTT
GCTAAAGTTTACGATTCTTCATTTAATGCTGTTTTGAACGCTACGAATAATGGAACTGGTGATCTAATTCCAGAA
GATGTTTTAGACAGTTTGTTCCCATTATCCACCGATACACCGCTACCTTCTTCACTGGAAACTATAGGTATATTG
ACGGATCCAGTACTAAATAGCACCGACTATTTGATGTCTATGTCTTTACCTATTTTTGCCAATCCTTCTATTATC
TTGACTGATTCAAGGGTTTACGGATACATTACTATAATAATGTCGGCAGAGGGTCTGAAAAGTGTGTTCAACGAT
ACAACTGCTTTAGAACATTCCACAATTGCCATTATTTCTGCAGTATATAATAGTCAAGGCAAAGCTTCAGGGTAT
CATTTTGTCTTTCCACCGTATGGATCACGATCAGACCTCCCGCAAAAAGTTTTTCTATAAAAAATGATACATTC
ATTAGTAGCGCATTTAGAAACGGGAAGGGAGGGTCTTTGAAACAAACCAATATCCTTTCTACACGGAATACTGCT
TTAGGCTATTCACCATGTTCGTTTAACCTAGTTAATTGGGTCGCGATAGTTTCACAGCCTGAGTCGGTTTTCCTT
TCTCCAGCAACGAAACTAGCAAAAATCATCACCGGCACTGTCATCGCTATTGGTGTCTTTGTCATTTTGTTAACC
CTTCCTCTAGCACACTGGGCAGTGCAACCAATTGTACGTCTACAAAAGGCAACTGAATTAATTACAGAGGGGAGA
GGCCTTCGACCGAGCACCCCAAGAACGATAAGCAGAGCCAGTTCATTCAAAAGAGGATTTAGTTCTGGATTTGCT
GTTCCTTCTTCGTTATTACAATTTAATACTGCTGAAGCTGGCAGCACCACAAGCGTAAGTGGCCATGGAGGCAGT
GGCCATGGCAGTGGTGCAGCTTTTTCAGCAAATAGTAGCATGAAAAGCGCTATAAACCTTGGAAATGAGAAAATG
TCACCTCCAGAGGAGGAGAACAAAATACCGAATAACCACACCGATGCTAAAATATCAATGGATGGCTCGCTAAAT
CACGATTTGCTTGGACCACATTCCTTGAGACATAATGACACTGACAGAAGTTCCAATAGATCTCACATTCTCACA
ACTTCTGCAAATTTAACTGAAGCTAGGCTACCAGATTATAGAAGACTATTTTCTGATGAACTTTCCGATTTAACA
GAAACCTTCAATACTATGACAGACGCATTAGACCAACATTATGCTCTTCTAGAAGAAAGAGTTAGGGCGAGGACA
AAACAACTCGAAGCTGCCAAGATTGAGGCAGAGGCCGCAAATGAAGCAAAAACCGTCTTTATTGCCAATATTTCG
CACGAATTGAGAACGCCTTTAAATGGTATTCTGGGTATGACGGCTATTTCAATGGAAGAAACCGATGTTAACAAA
ATAAGAAATAGTTTAAAACTCATTTTTAGATCAGGTGAGCTTTTGCTTCATATTCTAACGGAATTGTTAACTTTT
TCCAAAAACGTTCTTCAAAGAACGAAACTGGAGAAAAGAGATTTTTGCATTACCGATGTTGCCTTACAAATAAAA
TCGATATTTGGTAAAGTTGCAAAGGATCAGCGTGTTCGTCTTTCAATATCATTGTTTCCTAATTTGATAAGGACA
ATGGTTCTTTGGGGTGATTCCAACAGAATTATTCAAATTGTGATGAATCTAGTGTCCAATGCACTAAAGTTCACC
CCTGTAGATGGTACCGTTGATGTAAGAATGAAACTGTTGGGTGAATACGACAAAGAATTAAGCGAGAAGAAGCAA
TACAAAGAAGTGTATATCAAAAAAGGGACAGAAGTAACCGAAAATTTAGAAACTACAGATAAATACGATCTTCCA
ACTTTATCGAACCATAGGAAAAGTGTCGATTTAGAATCCAGCGCTACTTCCCTAGGAAGTAATAGAGACACTTCG
ACAATTCAGGAAGAGATAACAAAAAGAAATACTGTTGCGAATGAAAGTATCTATAAGAAAGTGAATGACAGGGAA
AAAGCTTCGAATGATGATGTATCTTCTATAGTATCAACAACTACCAGCTCGTATGATAACGCTATCTTCAATAGT
CAGTTCAATAAAGCACCTGGCTCAGATGATGAAGAAGGTGGTAACCTAGGAAGACCTATCGAAAACCCCAAAACG
TGGGTTATTTCTATTGAAGTGGAAGACACTGGGCCTGGTATTGACCCTTCCTTACAAGAATCTGTATTTCATCCA
TTTGTTCAAGGTGATCAAACATTGTCCAGGCAATATGGTGGTACTGGCTTAGGTCTATCAATCTGTAGACAGTTA
GCAAATATGATGCATGGAACGATGAAATTAGAGTCGAAAGTAGGTGTTGGTAGTAAATTCACTTTTACCTTGCCA
TTAAATCAAACTAAAGAGATCAGTTTTGCAGATATGGAGTTTCCTTTTGAGGACGAATTTAATCCTGAGAGTAGA
AAGAACAGAAGAGTCAAGTTTAGTGTTGCTAAAAGCATCAAGAGCCGACAATCCACATCATCTGTTGCAACACCA
GCTACAAATAGAAGTAGCCTAACCAACGACGTGCTACCGGAGGTAAGAAGTAAAGGTAAGCATGAGACGAAAGAT
GTTGGAAATCCTAACATGGGAAGAGAAGAAAAAACGACAATGGAGGGCTTGAACAACTGCAGGAAAAAATATT
AAACCTTCTATATGTCTTACAGGTGCTGAAGTTAACGAACAAAATTCCTTGTCTTCTAAGCATCGTTCTCGACAT
GAAGGTCTAGGTTCTGTCAATCTTGATAGACCATTTTTGCAAAGTACTGGTACAGCCACATCAAGTAGAAACATC
CCCACAGTCAAAGACGACGATAAAAATGAAACAAGTGTCAAAATTTTGGTTGTAGAAGATAATCATGTAAATCAG
GAAGTTATCAAAAGAATGTTGAACTTGGAGGGCATTGAAAATATTGAACTGGCTTGCGATGGCCAAGAAGCATTC
GACAAAGTTAAAGAATTGACATCTAAGGGCGAAAATTATAATATGATTTTCATGGATGTCCAGATGCCTAAAGTG
GATGGTTTACTTTCTACCAAGATGATAAGGCGCGATTTAGGTTATACCTCACCTATTGTCGCTCTAACCGCTTTT
GCTGACGATAGCAACATTAAAGAATGTTTGGAATCAGGAATGAACGGATTTTTATCGAAACCAATCAAAAGACCA
AAATTGAAAACTATTCTTACTGAGTTTTGTGCAGCATATCAGGGAAAGAAAAATAACAAA
```

MRFGLPSKLELTPPFRIGIRTQLTALVSIVALGSLIILAVTTGVYFTSNYKNLRSDRLYIAAQLKSSQ
IDQTLNYLYYQAYYLASRDALQSSLTSYVAGNKSADNWVDSLSVIQKFLSSSNLFYVAKVYDSSFNAV
LNATNNGTGDLIPEDVLDSLFPLSTDTPLPSSLETIGILTDPVLNSTDYLMSMSLPIFANPSIILTDS
RVYGYITIIMSAEGLKSVFNDTTALEHSTIAIISAVYNSQGKASGYHFVFPPYGSRSDLPQKVFSIKN
DTFISSAFRNGKGGSLKQTNILSTRNTALGYSPCSFNLVNWVAIVSQPESVFLSPATKLAKIITGTVI
AIGVFVILLTLPLAHWAVQPIVRLQKATELITEGRGLRPSTPRTISRASSFKRGFSSGFAVPSSLLQF
NTAEAGSTTSVSGHGGSGHGSGAAFSANSSMKSAINLGNEKMSPPEEENKIPNNHTDAKISMDGSLNH
DLLGPHSLRHNDTDRSSNRSHILTTSANLTEARLPDYRRLFSDELSDLTETFNTMTDALDQHYALLEE
RVRARTKQLEAAKIEAEAANEAKTVFIANISHELRTPLNGILGMTAISMEETDVNKIRNSLKLIFRSG
ELLLHILTELLTFSKNVLQRTKLEKRDFCITDVALQIKSIFGKVAKDQRVRLSISLFPNLIRTMVLWG
DSNRIIQIVMNLVSNALKFTPVDGTVDVRMKLLGEYDKELSEKKQYKEVYIKKGTEVTENLETTDKYD
LPTLSNHRKSVDLESSATSLGSNRDTSTIQEEITKRNTVANESIYKKVNDREKASNDDVSSIVSTTTS
SYDNAIFNSQFNKAPGSDDEEGGNLGRPIENPKTWVISIEVEDTGPGIDPSLQESVFHPFVQGDQTLS
RQYGGTGLGLSICRQLANMMHGTMKLESKVGVGSKFTFTLPLNQTKEISFADMEFPFEDEFNPESRKN
RRVKFSVAKSIKSRQSTSSVATPATNRSSLTNDVLPEVRSKGKHETKDVGNPNMGREEKNDNGGLEQL
QEKNIKPSICLTGAEVNEQNSLSSKHRSRHEGLGSVNLDRPFLQSTGTATSSRNIPTVKDDDKNETSV
KILVVEDNHVNQEVIKRMLNLEGIENIELACDGQEAFDKVKELTSKGENYNMIFMDVQMPKVDGLLST
KMIRRDLGYTSPIVALTAFADDSNIKECLESGMNGFLSKPIKRPKLKTILTEFCAAYQGKKNNK

```
ATGAGCTTTTCCACCATAAATAGCAACGTCAATAAAACCACCGGCGATAGCAATAATAACACCACCGA
GAACAGTTCGACTGCAGACCTTTTAGGAATGGACTTGTTGCAGAGCGGGCCTCGACTGATGAACACGA
TGCAGCCAAACAACTCTTCTGACATGCTGCACATTAACAACAAGACTAATAACGTTCAACAACCAGCT
GGAAACACAAATATCAGCAGTGCTAATGCGGGAGCAAAGGCTCCAGCAAATGAGTTCGTAAGAAAACT
GTTCAGGATACTGGAAAACAATGAATATCCTGACATTGTAACTTGGACTGAGAACGGCAAAAGTTTCG
TCGTTTTGGACACAGGAAAGTTCACTACGCATATATTGCCTAATCACTTCAAACATTCAAATTTTGCA
TCTTTTGTAAGGCAACTAAACAAGTATGACTTTCACAAGGTTAAGAGAAGTCCCGAGGAAAGACAGAG
ATGTAAATATGGCGAACAAAGTTGGGAGTTTCAGCATCCAGAATTTAGAGTCCATTACGGAAAAGGTC
TCGATAACATCAAAAGGAAAATTCCGGCGCAAAGGAAAGTGCTTTTGGATGAATCTCAAAAGGCTCTT
TTGCATTTCAATAGTGAAGGCACTAACCCCAACAATCCTTCTGGGTCTCTTTTGAATGAATCCACCAC
AGAGCTGTTGTTAAGCAATACCGTAAGTAAAGATGCATTTGGAAATCTAAGAAGGCGAGTAGACAAAC
TACAAAAGGAGTTGGATATGTCCAAAATGGAGAGTTATGCTACTAAAGTAGAACTACAAAAGTTGAAC
TCGAAATACAATACGGTTATCGAAAGTTTGATAACATTCAAGACCATAAATGAAAATTTACTCAACAA
CTTCAACACTCTGTGTTCCACTTTGGCAAATAATGGTATTGAAGTGCCAATATTTGGCGACAATGGAA
ACCGTAACCCAACTGGTAATACCAACCCAGCAACAACAACAGCTATCCAAAGCAACAACAACACCAAC
AATGCTTCTCCGGCAACATCTACAGTTTCCTTACAACTACCTAATTTACCCGATCAGAATAGCCTAAC
ACCAAATGCTCAAAATAACACAGTCACGCTACGAAAAGGTTTCCATGTACTGTTGGTGGAAGATGACG
CAGTGTCTATACAGTTGTGTTCAAAATTTTTACGGAAATATGGCTGTACTGTCCAAGTTGTCAGCGAC
GGTCTTTCAGCTATCTCAACACTAGAGAAGTATAGGTATGATTTGGTTTTAATGGACATTGTTATGCC
AAACCTAGATGGTGCCACAGCGACATCCATTGTCAGAAGTTTTGATAATGAGACTCCCATCATTGCCA
TGACAGGTAACATTATGAATCAAGACTTGATCACATACTTACAACATGGAATGAATGATATCTTGGCC
AAACCATTCACGAGGGATGATTTACACTCAATTTTAATACGTTATCTAAAGGACCGTATTCCTTTATG
CGAACAGCAATTACCACCTCGCAACTCTTCGCCACAAACTCATTCCAACACCAATACTGCTAATTCGA
ATCCTAATACGATTAATGAACAGTCGTTAGCCATGTTACCACAAGATAATCCGTCAACTACTACCCCT
GTTACCCCAGGTGCCTCTATATCTTCTGCACAGCATGTTCAACAAGGTCAACAAGAACAGCAGCATCA
AATTTTCCATGCTCAGCAGCAGCAGCAGCATCACAACGCCATTGCTAATGCTAGGTCAGACGTAGCCA
TACCGAATTTGGAACATGAAATCAACACTGTACCACATTCCTCAATGGGTTCCACTCCGCAATTACCA
CAATCTACACTTCAAGAAAACCAGCTATCA
```

B.

```
MSFSTINSNVNKTTGDSNNNTTENSSTADLLGMDLLQSGPRLMNTMQPNNSSDMLHINNKTNNVQQPA
GNTNISSANAGAKAPANEFVRKLFRILENNEYPDIVTWTENGKSFVVLDTGKFTTHILPNHFKHSNFA
SFVRQLNKYDFHKVKRSPEERQRCKYGEQSWEFQHPEFRVHYGKGLDNIKRKIPAQRKVLLDESQKAL
LHFNSEGTNPNNPSGSLLNESTTELLLSNTVSKDAFGNLRRRVDKLQKELDMSKMESYATKVELQKLN
SKYNTVIESLITFKTINENLLNNFNTLCSTLANNGIEVPIFGDNGNRNPTGNTNPATTTAIQSNNNTN
NASPATSTVSLQLPNLPDQNSLTPNAQNNTVTLRKGFHVLLVEDDAVSIQLCSKFLRKYGCTVQVVSD
GLSAISTLEKYRYDLVLMDIVMPNLDGATATSIVRSFDNETPIIAMTGNIMNQDLITYLQHGMNDILA
KPFTRDDLHSILIRYLKDRIPLCEQQLPPRNSSPQTHSNTNTANSNPNTINEQSLAMLPQDNPSTTTP
VTPGASISSAQHVQQGQQEQQHQIFHAQQQQQHHNAIANARSDVAIPNLEHEINTVPHSSMGSTPQLP
QSTLQENQLS
```

ATGGACTACAACAAGAGATCTTCGGTCTCAACCGTGCCTAATGCAGCTCCCATAAGAGTCGG
ATTCGTCGGTCTCAACGCAGCCAAAGGATGGGCAATCAAGACACATTACCCCGCCATACTGC
AACTATCGTCACAATTTCAAATCACTGCCTTATACAGTCCAAAAATTGAGACTTCTATTGCC
ACCATTCAGCGTCTAAAATTGAGTAATGCCACTGCTTTTCCCACTTTAGAGTCATTTGCATC
ATCTTCCACTATAGATATGATAGTGATAGCTATCCAAGTGGCCAGCCATTATGAAGTTGTTA
TGCCTCTCTTGGAATTCTCCAAAAATAATCCGAACCTCAAGTATCTTTTCGTAGAATGGGCC
CTTGCATGTTCACTAGATCAAGCCGAATCCATTTATAAGGCTGCTGCTGAACGTGGGGTTCA
AACCATCATCTCTTTACAAGGTCGTAAATCACCATATATTTTGAGAGCAAAAGAATTAATAT
CTCAAGGCTATATCGGCGACATTAATTCGATCGAGATTGCTGGAAATGGCGGTTGGTACGGC
TACGAAAGGCCTGTTAAATCACCAAAATACATCTATGAAATCGGGAACGGTGTAGATCTGGT
AACCACAACATTTGGTCACACAATCGATATTTTACAATACATGACAAGTTCGTACTTTTCCA
GGATAAATGCAATGGTTTTCAATAATATTCCAGAGCAAGAGCTGATAGATGAGCGTGGTAAC
CGATTGGGCCAGCGAGTCCCAAAGACAGTACCGGATCATCTTTTATTCCAAGGCACATTGTT
AAATGGCAATGTTCCAGTGTCATGCAGTTTCAAAGGTGGCAAACCTACCAAAAAATTTACCA
AAAATTTGGTCATTGACATTCACGGTACCAAGGGAGATTTGAAACTTGAAGGCGATGCCGGC
TTCGCAGAAATTTCAAATCTGGTCCTTTACTACAGTGGAACTAGAGCAAACGACTTCCCGCT
AGCCAATGGACAACAAGCTCCTTTAGACCCGGGGTATGATGCAGGTAAAGAAATCATGGAAG
TATATCATTTACGAAATTATAATGCCATTGTGGGTAATATTCATCGACTGTATCAATCTATC
TCTGACTTCCACTTCAATACAAAGAAAATTCCTGAATTACCCTCACAATTTGTAATGCAAGG
TTTCGATTTCGAAGGCTTTCCCACCTTGATGGATGCTCTGATATTACACAGGTTAATCGAGA
GCGTTTATAAAGTAACATGATGGCTCCACATTAAACGTTAGCAATATCTCGCATTATAGT
TTA

B.

MDYNKRSSVSTVPNAAPIRVGFVGLNAAKGWAIKTHYPAILQLSSQFQITALYSPKIETSIA
TIQRLKLSNATAFPTLESFASSSTIDMIVIAIQVASHYEVVMPLLEFSKNNPNLKYLFVEWA
LACSLDQAESIYKAAAERGVQTIISLQGRKSPYILRAKELISQGYIGDINSIEIAGNGGWYG
YERPVKSPKYIYEIGNGVDLVTTTFGHTIDILQYMTSSYFSRINAMVFNNIPEQELIDERGN
RLGQRVPKTVPDHLLFQGTLLNGNVPVSCSFKGGKPTKKFTKNLVIDIHGTKGDLKLEGDAG
FAEISNLVLYYSGTRANDFPLANGQQAPLDPGYDAGKEIMEVYHLRNYNAIVGNIHRLYQSI
SDFHFNTKKIPELPSQFVMQGFDFEGFPTLMDALILHRLIESVYKSNMMGSTLNVSNISHYS
L

ATGAGTGAGAAGGCAGAGATCGAGGTTCCGCCGCAAAAATCGACATTCCCTCGCAGTGTGCA
CTTCGCTCCACTTCATATTCCACTGGAGAGACGCCTACAGACTTTGGCAGTCTTATTCCACA
CTGTCGCGCTACCATACTGCATCGGTCTGTTCTTTCTCATGCTCGCGTTCCCTCCTTTTTGG
CCATTATTGGTAATGTATGTCATATACGCATACGGGTTCGACCACTCGAGCTCGAACGGAGA
GATCTCCGCCGGCGATCGCCGCTGTTTCGAAGACTCCCGTTGTTCAGGCTGTATTGTGATT
ACTTCCCCATCCACATTCACCGGGAGGTTCCGCTCGAGCCGACGTTTCCTGGTCGCCTTCGC
GAACCGAGTGGCCTTGTCGAGCGGTGGATTGCGAAGATGTTCGGCGTGCAGGACGCTGTTGT
CGAGGGAAATGAATCTGACGTTAAGGCCACGGCCAACGGCAATGGGACGACGAAAGAAATCG
GACCGACGTATGTTTTCGGCTATCATCCGCATGGAATTGTTAGCTTGGGTGCGTTTGGTGCT
ATTGGTACGGAAGGCGCTGGATGGGAGAAGCTCTTTCCTGGGATCCCGGTGTCACTGCTGAC
TCTCGAAACAAATTTCAGCCTTCCATTTTACAGAGAGTATTTGCTGTCACTTGGGATTGCTT
CAGTATCTCGACGGTCTTGTACCAATCTCCTCAAACACGACCAATCCATCTGCATCGTTATC
GGCGGCGCCCAAGAGTCGCTCTTAGCGGAACCAGGCACTCTAGATCTGATCCTCGTTAAACG
TCGCGGTTTTGTCAAACTTGCAATGTCAACGGCGCGGGTATCTGACCAACCGATTTGTCTTG
TTCCGATCCTCAGTTTCGGCGAGAACGACGTGTACGACCAAGTCCGCGGGGACCGATCGTCG
AAGTTGTATAAGATCCAGACTTTTATCAAGAAAGCGGCCGGGTTTACGCTACCATTGATGTA
TGCGCGCGGTATATTTAATTACGACTTTGGGCTGATGCCGTACCGCAGGCAAATGACGCTCG
TGGTCGGCAAGCCGATTGCAGTGCCGTACGTGGCCCAGCCTACGGAGGCTGAAATCGAAGTG
TATCACAAGCAGTACATGGATGAATTGAGGAGGTTATGGGACACGTATAAGGACGACTATTT
TGTAGACCACAAGGGCAAGGGGGTCAAGAATTCCGAGATGCGTTTTGTGGAG

B.

MSEKAEIEVPPQKSTFPRSVHFAPLHIPLERRLQTLAVLFHTVALPYCIGLFFLMLAFPPFW
PLLVMYVIYAYGFDHSSSNGEISRRRSPLFRRLPLFRLYCDYFPIHIHREVPLEPTFPGRLR
EPSGLVERWIAKMFGVQDAVVEGNESDVKATANGNGTTKEIGPTYVFGYHPHGIVSLGAFGA
IGTEGAGWEKLFPGIPVSLLTLETNFSLPFYREYLLSLGIASVSRRSCTNLLKHDQSICIVI
GGAQESLLAEPGTLDLILVKRRGFVKLAMSTARVSDQPICLVPILSFGENDVYDQVRGDRSS
KLYKIQTFIKKAAGFTLPLMYARGIFNYDFGLMPYRRQMTLVVGKPIAVPYVAQPTEAEIEV
YHKQYMDELRRLWDTYKDDYFVDHKGKVKNSEMRFVE

ATGTCAGGAACATTCAATGATATAAGAAGAAGGAAGAAGGAAGAAGGAAGCCCTACAGCCGG
TATTACCGAAAGGCATGAGAATAAGTCTTTGTCAAGCATCGATAAAAGAGAACAGACTCTCA
AACCACAACTAGAGTCATGCTGTCCATTGGCGACCCCTTTTGAAAGAAGGTTACAAACTCTG
GCTGTAGCATGGCACACTTCTTCATTTGTACTCTTCTCCATATTTACGTTATTTGCAATCTC
GACACCAGCACTGTGGGTTCTTGCTATTCCATATATGATTTATTTTTTTTCGATAGGTCTC
CTGCAACTGGCGAAGTGGTAAATCGATACTCTCTTCGATTTCGTTCATTGCCCATTTGGAAG
TGGTATTGTGATTATTTCCCTATAAGTTTGATTAAAACTGTCAATTTAAAACCAACTTTTAC
GCTTTCAAAAAATAAGAGAGTTAACGAAAAAAATTACAAGATTAGATTGTGGCCAACTAAGT
ATTCCATTAATCTCAAAAGCAACTCTACTATTGACTATCGCAACCAGGAATGTACAGGGCCA
ACGTACTTATTTGGTTACCATCCACACGGCATAGGAGCACTTGGTGCGTTTGGAGCGTTTGC
AACAGAAGGTTGTAACTATTCCAAGATTTTCCCAGGTATTCCTATTTCTCTGATGACACTGG
TCACACAATTTCATATCCCATTGTATAGAGACTACTTATTGGCGTTAGGTATTCTTCAGTA
TCTCGGAAAAACGCTTTAAGGACTCTAAGCAAAAATCAGTCGATCTGCATTGTTGTTGGTGG
CGCTAGGGAATCTTTATTAAGTTCAACAAATGGTACACAACTGATTTTAAACAAAGAAAGG
GTTTTATTAAACTGGCCATTCAAACGGGGAATATTAACCTAGTGCCTGTGTTTGCATTTGGA
GAGGTGGACTGTTATAATGTTCTGAGCACAAAAAAGATTCAGTCCTGGGTAAAATGCAACT
ATGGTTCAAAGAAACTTTGGTTTTACCATTCCCATTTTCTACGCAAGAGGATTATTCAATT
ACGATTTCGGTTTGTTGCCATTTAGAGCGCCTATCAATGTTGTTGTTGGAAGGCCTATATAC
GTTGAAAAGAAAATAACAAATCCGCCAGATGATGTTGTTAATCATTTCCATGATTTGTATAT
TGCGGAGTTGAAAAGACTATATTACGAAAATAGAGAAAAATATGGGGTACCGGATGCAGAAT
TGAAGATAGTTGGG

B.

MSGTFNDIRRRKKEEGSPTAGITERHENKSLSSIDKREQTLKPQLESCCPLATPFERRLQTL
AVAWHTSSFVLFSIFTLFAISTPALWVLAIPYMIYFFFDRSPATGEVVNRYSLRFRSLPIWK
WYCDYFPISLIKTVNLKPTFTLSKNKRVNEKNYKIRLWPTKYSINLKSNSTIDYRNQECTGP
TYLFGYHPHGIGALGAFGAFATEGCNYSKIFPGIPISLMTLVTQFHIPLYRDYLLALGISSV
SRKNALRTLSKNQSICIVVGGARESLLSSTNGTQLILNKRKGFIKLAIQTGNINLVPVFAFG
EVDCYNVLSTKKDSVLGKMQLWFKENFGFTIPIFYARGLFNYDFGLLPFRAPINVVGRPIY
VEKKITNPPDDVVNHFHDLYIAELKRLYYENREKYGVPDAELKIVG

A.

B.

A.

B.

A.

B.

FIGURE 15
A.
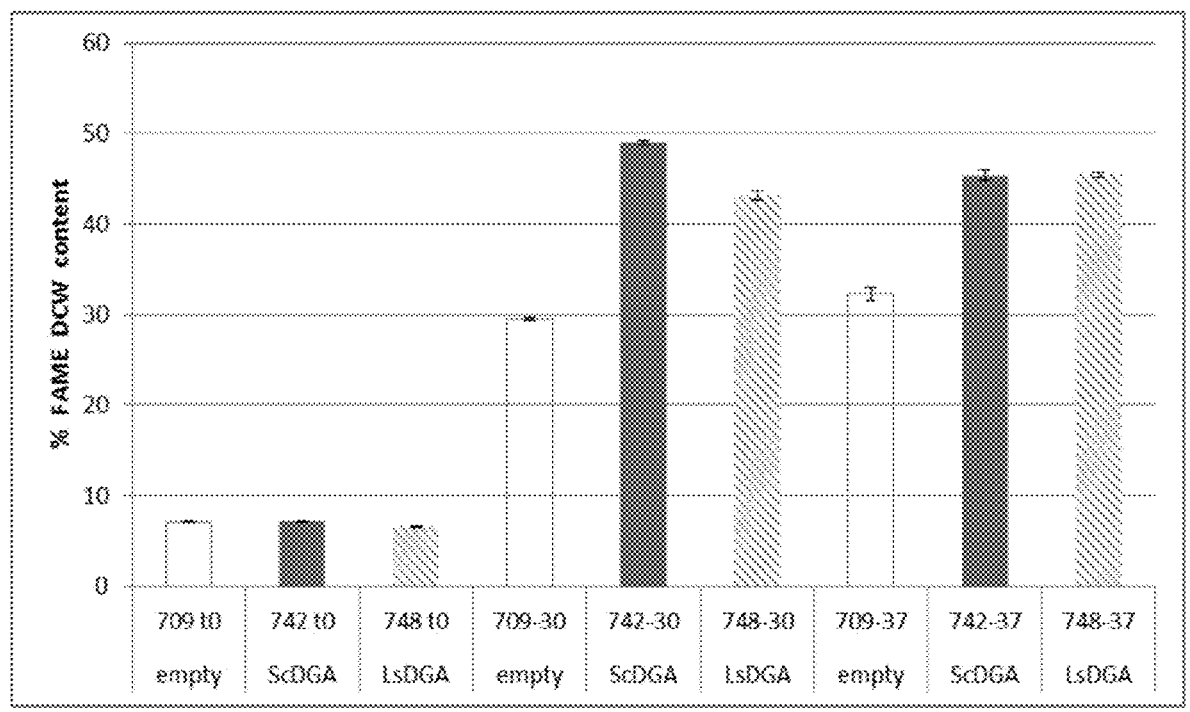
B.
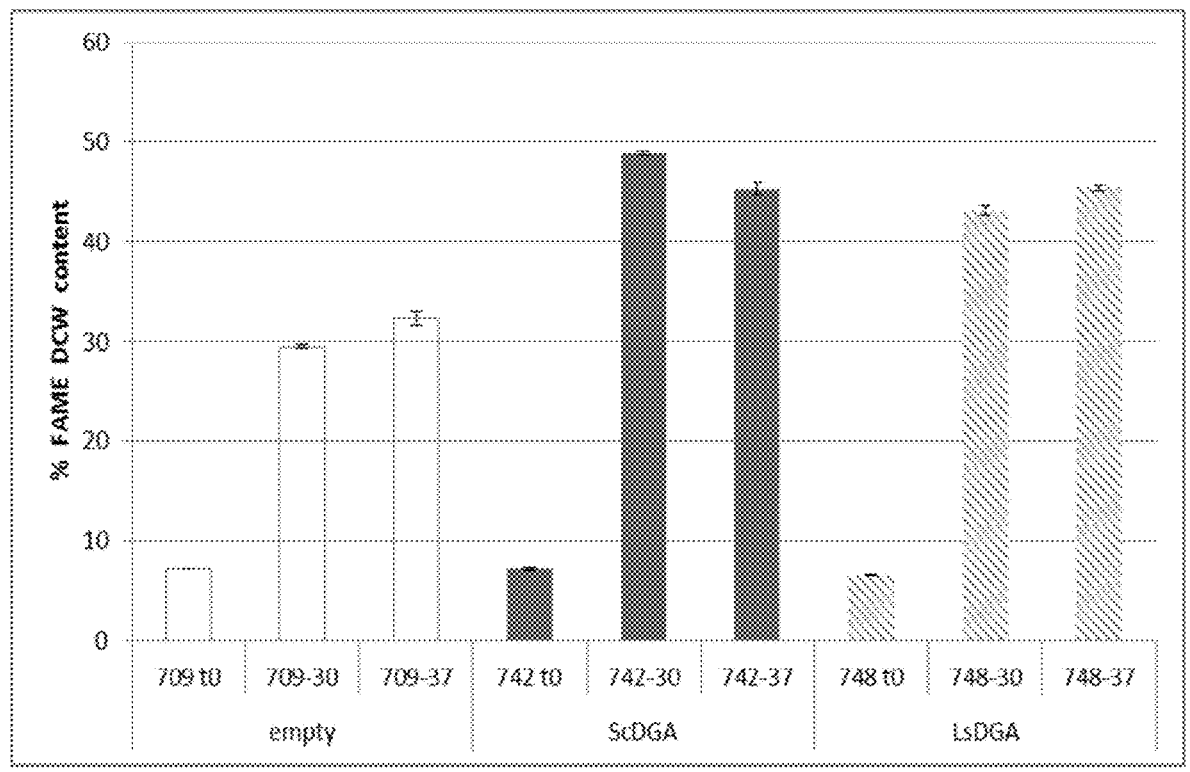

FIGURE 16
A.
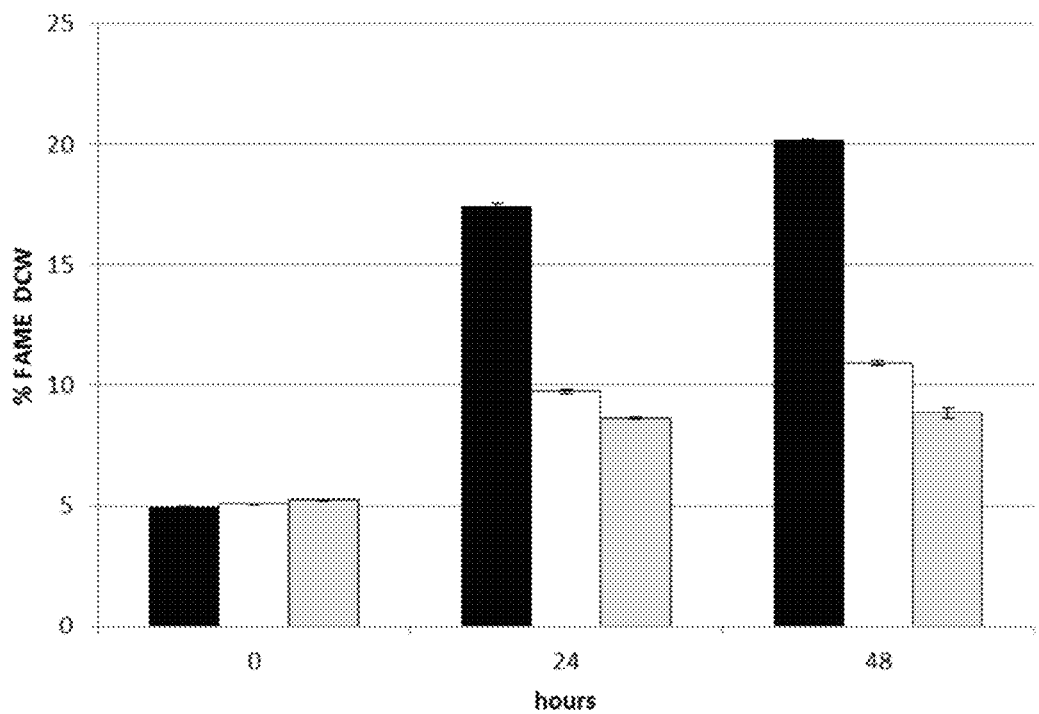
B.
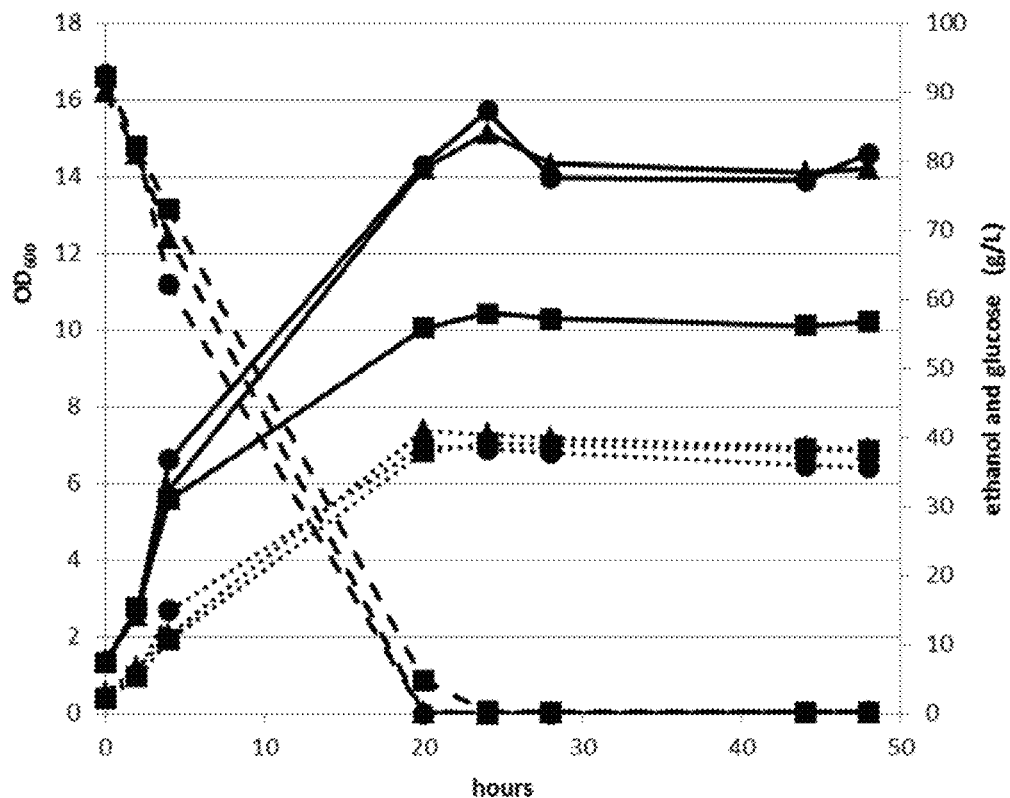

FIGURE 17
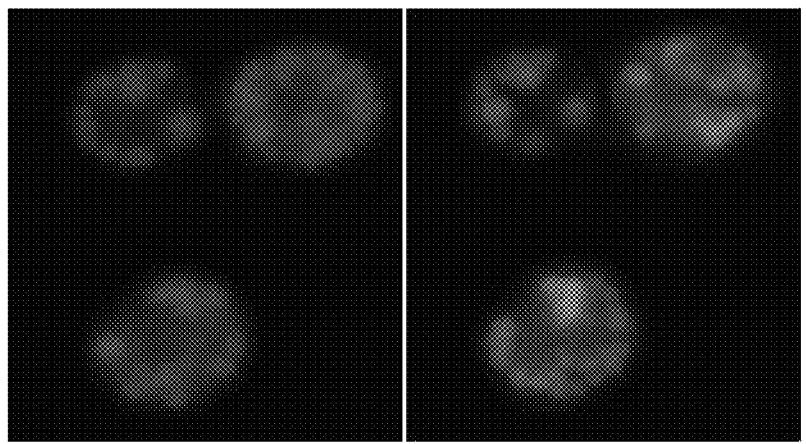
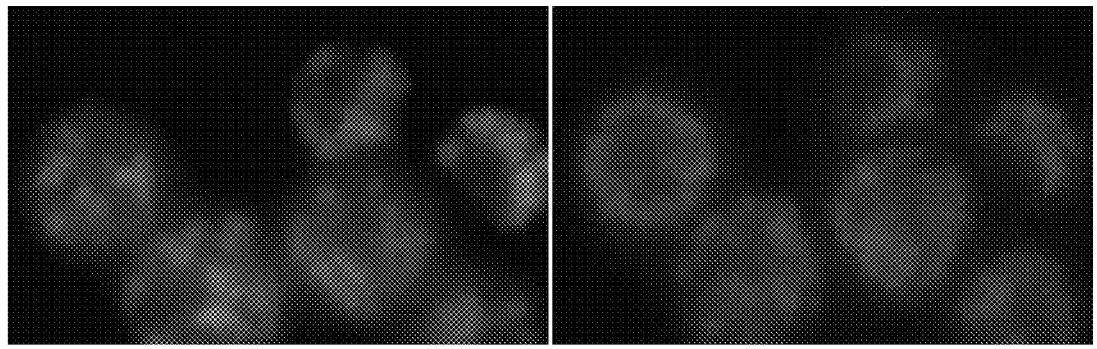

Regulates many cellular functions in response to various stresses. Upregulates TAG accumulation in *S. cerevisiae* when knocked-out.

XYLOSE UTILIZING OLEAGINOUS YEAST

CROSS-REFERENCE TO RELATED APPLICATIONS

This application claims priority to U.S. Provisional Applications No. 62/315,720, filed Mar. 31, 2016, and No. 62/235,057, filed Sep. 30, 2015, the contents of which are incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "14-96_ST25.txt," having a size in bytes of 127 kb and created on Sep. 28, 2016. Pursuant to 37 CFR § 1.52(e)(5), the information contained in the above electronic file is hereby incorporated by reference in its entirety.

BACKGROUND

*Saccharomyces cerevisiae* is known for robust ethanolic fermentation of various pre-treated lignocellulosic feedstocks for renewable fuels production. The two main monomeric sugars released during pretreatment and enzymatic saccharification of these feedstocks are glucose and xylose. The *S. cerevisiae* strain D5A has previously been used to ferment pre-treated switchgrass, rice straw, distiller's grains, and lodgepole pine feedstocks and was found to be tolerant to hydrolyzate products present in pre-treated hardwoods and to butanol up to 1%. However, the native strain, like all wild type *S. cerevisiae* strains, is unable to utilize xylose as a carbon source.

Likewise, *S. cerevisiae* is not typically considered an oleaginous yeast. The classical definition of an oleaginous yeast is one that accumulates greater than 20% dry cell weight (dcw) as lipids. *S. cerevisiae* is not known as being oleaginous, typically only accumulating 10-15% of its dry cell weight as lipids, whereas oleaginous yeasts may accumulate 25% to greater than 60% lipids dcw.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Provided herein are engineered yeast cells that express exogenously added genes encoding xylose reductase, xylitol dehydrogenase and xylulose kinase enzymes, that have been modified so that the snf1 gene of the yeast cell is ablated, and that have been modified to express the GAL2 transporter in the presence of glucose.

In some embodiments, the xylose reductase and xylitol dehydrogenase enzymes are from *Pichia stipitis*, such as the xylose reductase and xylitol dehydrogenase enzymes XYL1 and XYL2. In various embodiments, the xylulose kinase enzyme is *S. cerevisiae* XKS1. In others, the modification to express the GAL2 transporter in the presence of glucose is the ablation of at least one copy of a gene encoding a GAL80 protein.

In certain embodiments, the yeast cell also comprises a genetic modification that allows for overexpression of a diacylglycerol acyltransferase, such as DGA1 from *S. cerevisiae* or *L. starkeyi*.

In additional embodiments, the yeast cells also contain a genetic modification that allows for overexpression of a gene in the SLN1-YPD1-SKN7/SSK1 two-component regulatory system, such as a histidine kinase or SLN1 or SKN7.

In certain embodiments, the yeast cell is from of strain of the genus *Saccharomyces*, such as *Saccharomyces cerevisiae*.

In various embodiments, the yeast cell is from the strain BFY709, BFY742 or BFY748.

In some embodiments, the yeast cell accumulates at least 25% dcw, at least 30% dcw, or at least 35% dcw lipids when cultured in the presence of sugars. In additional embodiments, the yeast cell produces ethanol when cultured in the presence of sugars.

Also provided are methods for producing lipids or ethanol by culturing yeast cells with a source of sugar and recovering the lipids or ethanol from the culture.

In certain embodiments, the source of sugar is lignocellulosic biomass that has been subjected to enzymatic treatment to produce sugars.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 1 shows the nucleic acid sequence (A; SEQ ID NO:1) and amino acid sequence (B; SEQ ID NO:2) of XYL1 from *Pichia stipitis*.

FIG. 2 shows the nucleic acid sequence (A; SEQ ID NO:3) and amino acid sequence (B; SEQ ID NO:4) of XYL2 from *Pichia stipitis*.

FIG. 3 shows the nucleic acid sequence (A; SEQ ID NO:5) and amino acid sequence (B; SEQ ID NO:6) of XKS1 from *S. cerevisiae*.

FIG. 4 shows the nucleic acid sequence (A; SEQ ID NO:7) and amino acid sequence (B; SEQ ID NO:8) of SNF1 from *S. cerevisiae*.

FIG. 5 shows the nucleic acid sequence (A; SEQ ID NO:9) and amino acid sequence (B; SEQ ID NO:10) of SLN1 from *S. cerevisiae*.

FIG. 6 shows the nucleic acid sequence (A; SEQ ID NO:11) and amino acid sequence (B; SEQ ID NO:12) of SKN7 from *S. cerevisiae*.

FIG. 8 shows the nucleic acid sequence (A; SEQ ID NO:13) and amino acid sequence (B; SEQ ID NO:14) of GAL80 from *S. cerevisiae*.

FIG. 9 shows the nucleic acid sequence (A; SEQ ID NO:15) and amino acid sequence (B; SEQ ID NO:16) of DGA1 from *Lipomyces starkeyi*.

FIG. 10 shows the nucleic acid sequence (A; SEQ ID NO:17) and amino acid sequence (B; SEQ ID NO:18) of DGA1 from *S. cerevisiae*.

FIG. 15 shows lipid production of *S. cerevisiae* strains in aerobic shake flasks, with the data grouped by time and growth temperature (A) or strain (B). Strains shown are BFY709 (white bars), BFY742 (solid bars), and BFY748 (diagonal stripes). Initial lipid content for each strain is represented by t0, while the −30 and −37 data represent growth of each strain at 30° C. or 37° C., respectively, for 120 hours.

FIG. 16 shows FAME and ethanol production, growth, and sugar utilization by BFY709 in pH and aeration controlled fermentors. (A) FAME accumulation: 5 mM $NH_4$ (black bars), 10 mM $NH_4$ (white bars), and YPD (grey bars). (B) Growth ($OD_{600}$, solid lines), ethanol production (dotted lines) and glucose consumption (g/L, dashed lines) for 5 mM $NH_4$ (squares), 10 mM $NH_4$ (circles) and YPD (triangles).

FIG. 17 shows Nile Red stained cells of *S. cerevisiae* BFY709 accumulated lipids after 72 hours of growth on glucose (A) or xylose (B). The two panels show the same cells with different focal planes illustrating the different levels of stained lipid vesicles.

DETAILED DESCRIPTION

Figure 7:
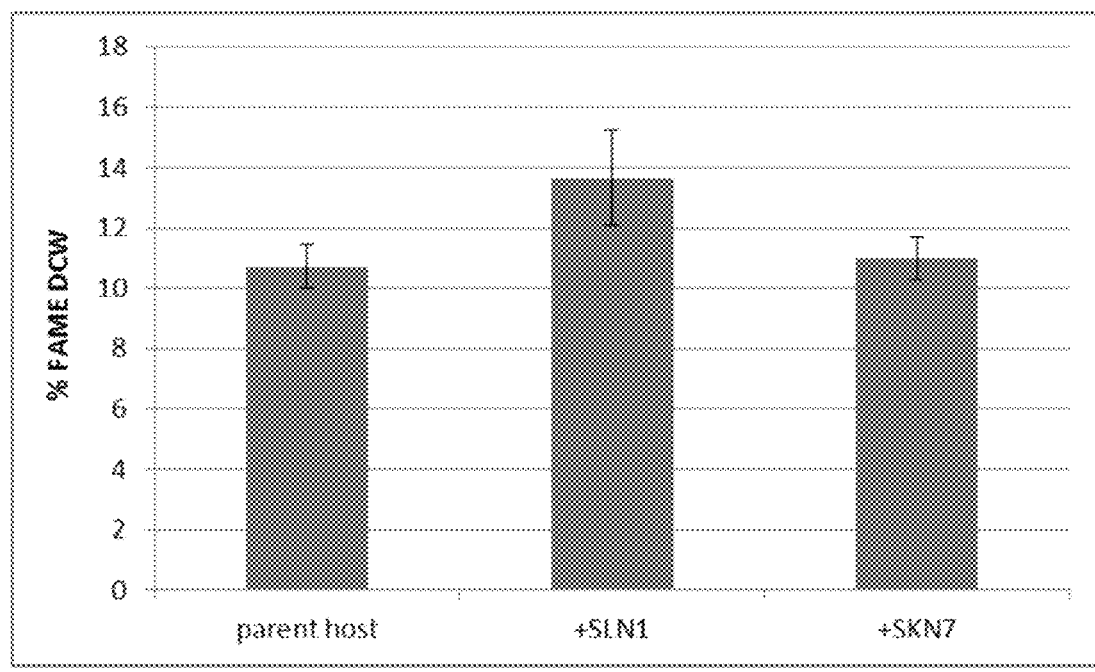
FIG. 7 shows lipid production of *S. cerevisiae* strains engineered to overexpress the histidine kinase/transcription factor homologs SLN1 and SKN7.

Presented herein are yeast strains that have been engineered to be capable of utilizing the lignocellulosic biomass derived sugar monomer xylose to produce ethanol while also exhibiting increased lipid accumulation. Such oleaginous yeast strains concurrently produce high titers of ethanol and up to 35% or greater lipids from either glucose or xylose. These next-generation biocatalysts exhibit expanded product ranges from a variety of feedstock sugars.

The modified yeast strains disclosed herein are able to accumulate lipids at higher levels when compared to the native, unmodified strains. Many native yeasts strains, including most strains of *Saccharomyces cerevisiae*, are not known to be lipid accumulating and typically accumulate less than 15-20% dry cell weight (dcw) internal lipids. In contrast the modified strains herein can reach lipid accumulation levels of up to 35% or 40% or more dcw lipids. In certain embodiments, the lipid accumulation levels may be greater than 20%, 25%, 30%, 35%, 40%, 45% or 50%.

Likewise, many native yeasts strains, including most strains of *Saccharomyces cerevisiae*, are not capable of utilizing xylose as a carbon source for growth, metabolism, or the production of lipids or ethanol. The modified yeast strains disclosed herein, in contrast, are able to grow and produce lipids and ethanol using xylose or mixed sugar streams that include xylose along with other sugars. The modifications result in oleaginous strains of yeast such as *S. cerevisiae* that can utilize the lignocellulosic biomass-derived sugar monomer xylose to produce ethanol concurrently with increased lipid accumulation. The strains demonstrate high lipid accumulation when specifically grown on xylose, allowing the production of a lipid feedstock from cellulosic-derived biomass at similar rates to glucose.

The yeast cells may be modified to express one or more exogenously added genes encoding enzymes that allow the cell to metabolize xylose. Exemplary enzymes include xylose reductase, xylitol dehydrogenase and xylulose kinase enzymes. Specific examples include the xylose reductase XYL1 and xylitol dehydrogenase XYL2 from *Pichia stipitis* and the xylulose kinase XKS1 from *S. cerevisiae*, the nucleic acid and amino acid sequences of which are provided in FIG. 1-3. Functional homologs of these enzymes from other species are also suitable for use in the present disclosure.

The yeast cells may be modified to not express the endogenous SNF1 enzyme by, for example, ablating or "knocking-out" one or both copies of the snf1 gene. In *S. cerevisiae*, the gene snf1 encodes the enzyme SNF1, an ADP-activated serine/threonine kinase that has many roles, including regulating carbon homeostasis and general stress responses, regulating genes involved in lipid synthesis and nitrogen metabolism, and phosphorylating, and thus inactivating, acetyl-CoA carboxylase. The nucleic acid sequence of snf1 and amino acid sequence of SNF1 in *S. cerevisiae* are presented in FIG. 4. Homologs of the snf1 gene and SNF1 enzyme from other species are also suitable for use in the present disclosure.

The yeast cells may be modified to express one or more exogenously added genes encoding a histidine kinase or transcription factor. Suitable histidine kinases or transcription factors include those that are part of two-component sensing and response regulatory systems induced by external stimuli, but have not been shown to govern lipid biosynthesis. Examples include SLN1 and SKN7 from *S. cerevisiae*, the nucleic acid and amino acid sequences for which are provided in FIGS. 5 and 6, respectively. FIG. 7 shows the lipid production of some exemplary strains of *S. cerevisiae* engineered to express exogenously added SLN1 or SKN7.

SLN1 is a histidine kinase that acts as an osmosensor at the plasma membrane. Part of the bifurcated SLN1-YPD1-SKN7/SSK1 two-component regulatory system, which controls activity of the HOG1 pathway and gene expression in response to changes in the osmolarity of the extracellular environment. Under normal osmotic conditions, the histidine kinase autophosphorylates His-576. This phosphate is subsequently transferred to Asp-1144, from where it is relayed to 'His-64' of the phosphorelay intermediate protein YPD1. Under high osmolarity conditions, the histidine kinase is no longer active.

SKN7, a nuclear response regulator and transcription factor, physically interacts with the Tup1-Cyc8 complex and recruits Tup1p to its targets. It is part of a branched two-component signaling system and required for optimal induction of heat-shock genes in response to oxidative stress SKN7 is also involved in osmoregulation and relocalizes to the cytosol in response to hypoxia. SKN7 has a paralog, HMS2, that arose from the whole genome duplication, and may be suitable for overexpression in cells are described herein.

In yeast, the GAL2 transporter is a major transporter of the pentose sugars xylose and arabinose, as well as glucose and galactose. In the presence of glucose, expression of the yeast GAL genes, including GAL2, is repressed via a GAL80-mediated repression mechanism. Disruption at the GAL80 locus can remove GAL80 repression of the galactose genes when glucose is present, providing active expression of the GAL2 transporter gene and allowing for co-fermentation of glucose and xylose. The nucleic acid and amino acid sequences for GAL80 from S. cerevisiae are provided in FIG. 8.

The yeast cells may be modified to provide constitutive expression of the pentose sugar transporter GAL2 even in the presence of glucose. This may be achieved by promoting the overexpression of GAL2 or by ablating a gene that acts as a negative regulator of GAL2 expression, such as GAL80. For example, the GAL80 locus may be disrupted by insertion of a targeting sequence into the locus. In the Examples below, genes encoding the xylose reductase, xylitol dehydrogenase and xylulose kinase enzymes are targeted to the GAL80 locus, thereby allowing for the overexpression of the xylose reductase, xylitol dehydrogenase and xylulose kinase enzymes while simultaneously ablating the expression of the GAL80 repressor. In some embodiments, one copy of GAL80 is ablated; in other embodiments, both copies of GAL80 may be ablated.

The yeast cells may be modified to express one or more exogenously added genes encoding a diacylglycerol acyltransferase. Diacylglycerol acyltransferase (DGA or DGAT) enzymes catalyze the formation of triglycerides from diacylglycerol and Acyl-CoA. While yeast naturally express various genes encoding DGAs, lipid production may be increased in yeast by engineering strains to overexpress DGA (for example, by adding one or more copies of an exogenous gene encoding DGA). Exemplary diacylglycerol acyltransferases include DGA1 from yeasts such as *Lipomyces starkeyi* and *S. cerevisiae*. The nucleic acid and amino acid sequences for DGA1 from *Lipomyces starkeyi* and *S. cerevisiae* are provided in FIGS. 9 and 10, respectively. Additional suitable diacylglycerol acyltransferases include those from diatoms, such as PtDGA from *Phaeodactylum tricornutum* (see SEQ ID NOS: 19 and 20). Type 1 or Type 2 diacylglycerol acyltransferase genes (e.g., DGAT1 or DGAT2 genes) from a variety of yeast and other microorganisms are suitable for use herein.

Yeast are typically cultured in nitrogen-rich media to promote robust growth, then shifted to media that lacks nitrogen or is nitrogen-deplete to promote lipid accumulation. In addition to increasing lipid accumulation in yeast cultured in this manner, the modifications disclosed herein may allow for enhanced lipid accumulation in nitrogen-rich conditions that also promote strong growth. This may allow the added advantage of eliminating a nitrogen starvation step during late stage growth in processes directed to oil production by yeast cells.

While the examples provided herein utilize strains of In *S. cerevisiae*, other yeasts are suitable for use with the described methods. Examples include yeast cells from the genus *Saccharomyces*, such as *S. pastorianus*, *S. paradoxus*, *S. bayanus*, and *S. boulardii*, among others. Additional suitable yeast cells include those from the genera *Brettanomyces* (e.g., *B. bruxellensis*, *B. anomalus*, *B. custersianus*, *B. naardenensis*, and *B. nanus*), *Lipomyces* (e.g., *L. starkeyi*), *Cryptococcus* (e.g., *C. curvatus*), *Rhodosporidium*, (e.g., *Rhodosporidium* sp.), *Rhodotorula* (e.g., *Rhodotorula* sp.), and *Yarrowia* (e.g., *Y. lipolytica* sp.). Exemplary *S. cerevisiae* strains include D5A and BY4741.

Yeast cells may be grown in any rich media (e.g., YPD) or minimum media conventionally used in the field. YPD medium contains about 1% yeast extract, 2% peptone and 2% dextrose. Yeast minimum media typically contains 0.67% of yeast nitrogen base ("YNB") without amino acids supplemented with appropriate amino acids or purine or pyrimidine bases. An amount of sugar, typically 2% unless otherwise indicated, may be used as carbon source, including glucose (dextrose), xylose, galactose, maltose or L-arabinose, among others.

The engineered strains can accumulate greater than 35%, 40% or 45% lipids dcw concurrently with ethanol production using xylose as the sole carbon source. In an exemplary embodiment, a large majority of the extracted lipids consist of 5 fatty acid species, C16:0 (palmitic), C16:1n7 (palmitoleic), C18:0 (stearic), C18:1n7 (oleic), and C18:1n9 (vaccenic). The relative distributions of lipids produced, however, may be varied with changes to the growth conditions.

In certain embodiments, a nucleic acid may be identical to the sequence represented herein. In other embodiments, the nucleic acids may be least about 80%, 81%, 82%, 83%, 84%, 85%, 86%, 87%, 88%, 89%, 90%, 91%, 92%, 93%, 94%, 95%, 96%, 97%, 98% or 99% identical to a nucleic acid sequence presented herein, or 80%, 81%, 82%, 83%, 84%, 85%, 86%, 87%, 88%, 89%, 90%, 91%, 92%, 93%, 94%, 95%, 96%, 97%, 98% or 99% identical to a nucleic acid sequence presented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

The nucleic acid molecules exemplified herein encode polypeptides with amino acid sequences represented herein. In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the reference amino acid sequence while possessing the function. The present disclosure encompasses yeast cells such as *S. cerevisiae* cells that contain the nucleic acid molecules described herein, have genetic modifications to the nucleic acid molecules, or express the polypeptides described herein.

Suitable vectors for gene expression may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including algal, bacterial, yeast, and mammalian vectors, have been described for replication and/or expression in various host cells or cell-free systems, and may be used with genes encoding the enzymes described herein for simple cloning or protein expression.

Certain embodiments may employ promoters or regulatory operons. The efficiency of expression may be enhanced by the inclusion of enhancers that are appropriate for the particular cell system that is used, such as those described in the literature. Suitable promoters also include inducible promoters. Expression systems for constitutive expression in yeast cells are available from commercial sources. Inducible expression systems are also suitable for use.

In exemplary embodiments, the host cell may be a microbial cell, such as a yeast cell or an algal cell, and may be from any genera or species of algae that is known to produce lipids or is genetically manipulable. Exemplary microorganisms include, but are not limited to, bacteria; fungi; archaea; protists; eukaryotes, such as algae; and animals such as plankton, planarian, and amoeba.

Host cells may be cultured in an appropriate fermentation medium. An appropriate, or effective, fermentation medium refers to any medium in which a host cell, including a genetically modified microorganism, when cultured, is capable of growing and producing products such as lipids or ethanol. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors or photobioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing yeast cells, for example, are available from ATCC.

Isolation or extraction of lipids from the cells may be aided by mechanical processes such as crushing, for example, with an expeller or press, by supercritical fluid extraction, or the like. Once the lipids have been released from the cells, they can be recovered or separated from a slurry of debris material (such as cellular residue, by-products, etc.). This can be done, for example, using techniques such as sedimentation or centrifugation. Recovered lipids can be collected and directed to a conversion process if desired.

Following lipid accumulation, lipids may be extracted from the cells by solvent extraction using, for example, a mixture of a non-polar solvent (e.g., hexane) and a polar solvent (e.g., isopropanol). Exemplary non-polar solvents include liquid alkanes such as pentane, hexane, heptane, octane, nonane or decane, while exemplary polar solvents include alcohols such as ethanol, propanol, or butanol (including the iso-forms such as isopropanol and isobutanol). Solvents are typically mixed at ratios ranging from 1:1 to 5:4 (vol/vol), and the solvent mix ratios may be tested to ensure full single-phase mixing.

Cell slurries may be mixed with solvents such as hexane and isopropanol for a period of time ranging from several minutes to several hours. The resulting solvent fraction may be separated from the solids fraction by, for example, centrifugation. Solvent phases may be separated by, for example, decanting or solvent aspiration. Lipids may then be isolated from the solvent fraction by removing the solvent and further purified or fractionated as desired. For example, lipids may be removed from the isolated solvent phase by vacuum distillation, allowing for recycling of the solvents for subsequent extractions, leaving behind the pure lipid fraction. Cell samples may be dewatered to alter the percentage of solids in the sample prior to the solvent extraction.

EXAMPLES

Example 1

Yeast Strains, Media, and Seed Culture Growth Conditions

The *S. cerevisiae* strains D5a, PE-2, AGL, and Fali (Broin, Inc.) used in this study were grown in YPD (Difco) at 30° C., 37° C., or 42° C. with shaking at 225 rpm for seed culture generation and strain maintenance.

Example 2

Genetic Methods

Figure 11:
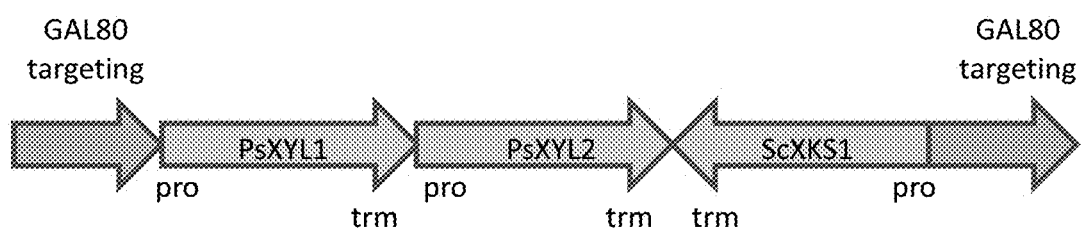
FIG. 11 shows a diagram of the expression vector that allows for xylose metabolism.

The XYL1-XYL2-XKS expression construct with 500 bp GAL80 targeting flanking sequences was synthesized as depicted in FIG. 11. Promoter sequences are indicated by "pro" and terminator sequences are indicated by "trm." The PGK1 promoter and Gala) terminator were used to drive XYL1 expression while the TDH3 promoter and GAL2 terminator were used to drive XYL2 expression and finally the PGI1 promoter and PDC1 terminator were used to drive XKS1 expression. The construct was isolated from the vector with the restriction enzyme NotI and 1 μg of gel-purified DNA was transformed into *S. cerevisiae* D5A.

As typical *S. cerevisiae* are not natively competent to utilize xylose, D5A was engineered to utilize xylose by integration of the XYL1-XYL2-XKS expression cassette. An over-expression construct harboring the xylose reductase (XYL1) and xylitol dehydrogenase (XYL2) from *Pichia stipitis* and xylulose kinase (XKS1) from *S. cerevisiae* was integrated at the chromosomal GAL80 locus completely replacing the GAL80 ORF to create strain BFY692. Proper targeting and knock-out of GAL80 was confirmed by PCR. Insertion at the GAL80 locus served to remove gal80 repression of the galactose genes when glucose is present providing active expression of the GAL2 transporter gene. GAL2 transporter is a major transporter of the pentose sugars xylose and arabinose, as well as glucose and galactose. Integration of the three-gene expression cassette was targeted to replace and knock-out a negative regulator of the pentose transporter GAL2 such as to effect constitutive expression of this transporter even in the presence of glucose, allowing for co-fermentation of glucose and xylose.

Strain BFY692 was further engineered to knock out the snf1 gene. This required a two-step process as D5A is a diploid yeast. One copy was ablated using a Snf1 targeted G418 resistance integration cassette, then the other copy using a similarly targeted Hygromycin B resistance integration cassette. Integration at one locus, then the other was confirmed by PCR. When grown for lipid accumulation in a nitrogen-limited culture, 34% FAME dcw accumulated in the double Snf1 knock out strain BFY709 compared to just 23% in the BFY692 parent FIG. 13).

The Snf1 deletion mutant was generated in two steps. Two snf1-targeting constructs were built either having G418 or hygromycin B as the selection markers. For integrative targeting, 690 and 400 bp of sequence upstream and downstream of the SNF1 locus respectively were added to either end of the constructs. In both constructs, the selection marker was driven by the PGK1 promoter and the GAL2 terminator.

Transformation of the linear xylose utilization construct or the SNF knock-out construct into S. cerevisiae D5A was performed using DMSO-enhanced lithium-acetate transformation with the following modifications. Cells were initially washed in water. Six-hundred µl of PEG4000 solution was added and just prior to heat shocking, 70 µl DMSO was added. Cells were heat-shocked for 15 minutes at 42° C. and the last wash step was eliminated. Cells were re-suspended in 10 mM TE and plated on appropriate selective plates.

Strain BFY709 was further engineered to overexpress a gene encoding diacylglycerol-acyltransferase (DGA) from either Saccharomyces cerevisiae or Lipomyces starkeyi (See sequences depicted in FIGS. 9 and 10). Each gene was cloned downstream of the S. cerevisiae TDH3 promoter and upstream of the GAL2 terminator for constitutive expression. The gene constructs were delivered on yeast plasmids bearing a 2u point of origin and using uracil auxotrophy (ura3 gene expression) for selection. The resulting strains were designated BFY742 (S. cerevisiae DGA) and BFY748 (L. starkeyi DGA).

Electrotransformation of E. coli DH5a was performed as described (Invitrogen 11319-019) and plated on LB plates containing 100 µg/ml ampicillin. E. coli plasmid DNA was isolated using a plasmid spin mini-prep kit (Qiagen, 27106).

Example 3

Lipid Accumulation in Shake Flasks or Fermentors

For lipid accumulation, yeast strains were grown in yeast nitrogen base (YNB) (Sigma Y-0626) containing 5% glucose and 5 mM $NH_4^+$. For shake flasks studies, cultures were grown at 30° C. with shaking at 225 rpm. Seed cultures were grown in 100 ml YPD in a 500 ml baffled flask. For lipid accumulation, yeast were grown in 300 ml of media in a 1 liter baffled flask in duplicate inoculated with washed cells from an overnight YPD seed culture to an initial $OD_{600}$ of 1. Cultures were incubated at 30° C. at 225 rpm. Fermentor experiments were done in Sartorius BioStat Q-Plus fermentors (Bohemia, N.Y.) at a 300 mL working volume. Three different media types containing 100 g/L glucose were used: YNB without ammonium sulfate (Sigma Y-1251) with 5 mM ammonium added back, YNB, and yeast peptone media (10 g/L yeast extract and 20 g/L peptone). The fermentations were inoculated at a starting $OD_{600}$ of 1 and were fermented for 48 hours at a pH of 5.2 and 10% saturation of dissolved oxygen. At each time point, 45 ml of culture was collected. From this sample, 5 ml were removed for OD, HPLC, and YSI analytics and the remaining 40 ml of culture was pelleted, washed with 50 ml water, and the washed pellet was frozen at −80° C. for in situ FAME analysis.

Figure 12:
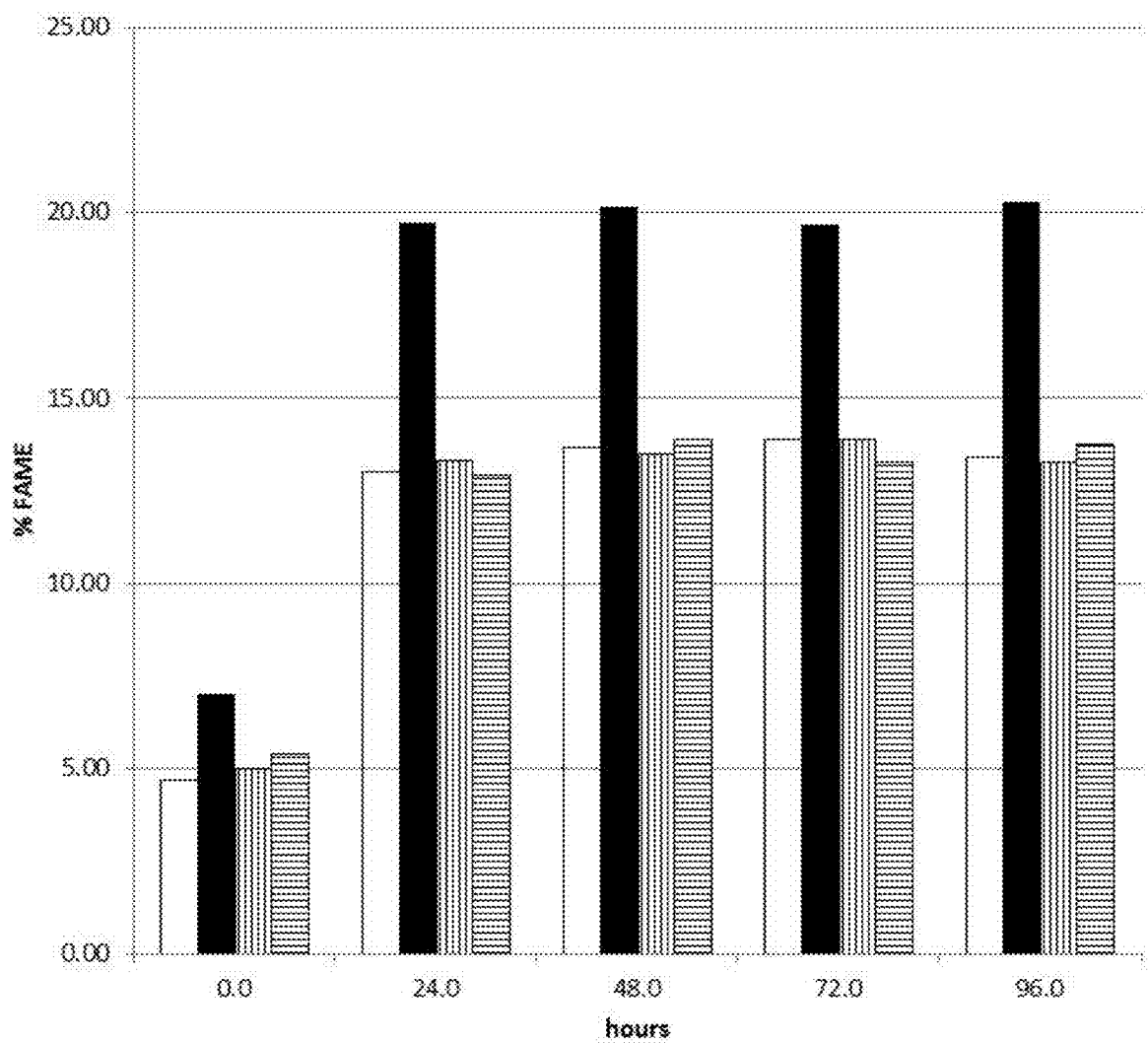
FIG. 12 shows FAME content and growth in *S. cerevisiae* strains. (A) FAME content (% dcw); AGL, white bar; D5a, black bar; Fali, vertical stripes; PE, horizontal stripes. (B) Growth ($OD_{600}$), ethanol production and glucose consumption (g/L); $OD_{600}$: AGL, diamonds, solid line; D5a, squares, solid line; Fali, triangles, solid line; PE, X, solid line. Ethanol production: AGL, diamonds, dotted line; D5a, squares, dotted line; Fali, triangles, dotted line; PE, X, dotted line. Glucose consumption: AGL, diamonds, dashed line; D5a, squares, dashed line; Fali, triangles, dashed line; PE, X, dashed line.
Figure 12:
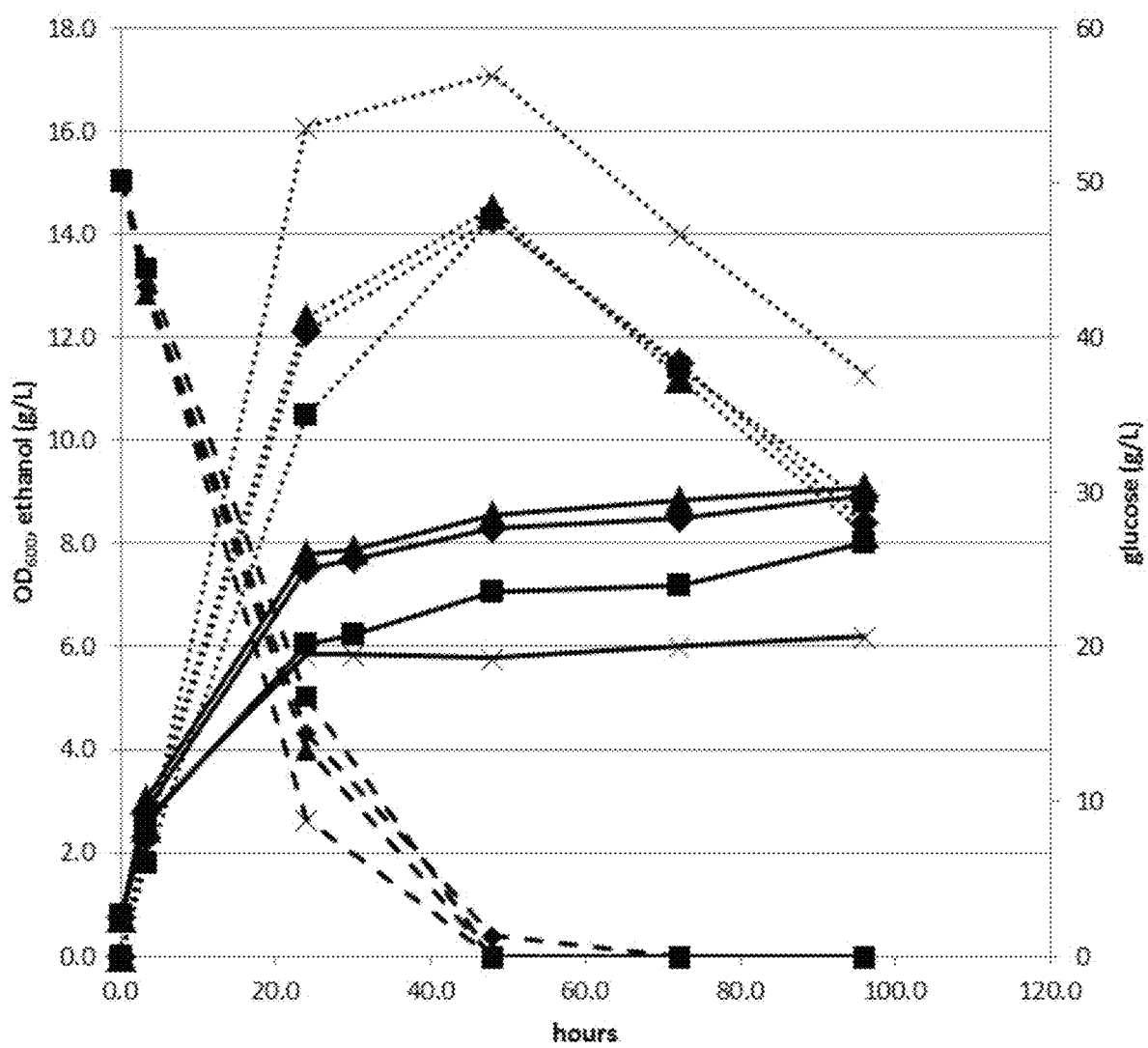

Four strains of S. cerevisiae, AGL, D5a, Fali and PE-2, previously used in industrial scale ethanol fermentations were characterized for lipid accumulation. As shown in panel a of FIG. 12, D5A accumulated 20% FAME on a dcw basis in a nitrogen-limited culture compared to less than 15% FAME dcw for the other 3 strains. D5A also produced the same amount of ethanol, 14 g/L, as two other strains while the PE-2 strain produced up to 3 g/L more ethanol. Glucose consumption was nearly identical with PE-2 being the most rapid (FIG. 12, panel B). Cell density of the PE-2 strain was the lowest while D5A was intermediate between PE-2 and the other two industrial strains.

Example 4

Growth, Ethanol Production and Lipid Accumulation of Engineered Yeast Strains

Figure 13:
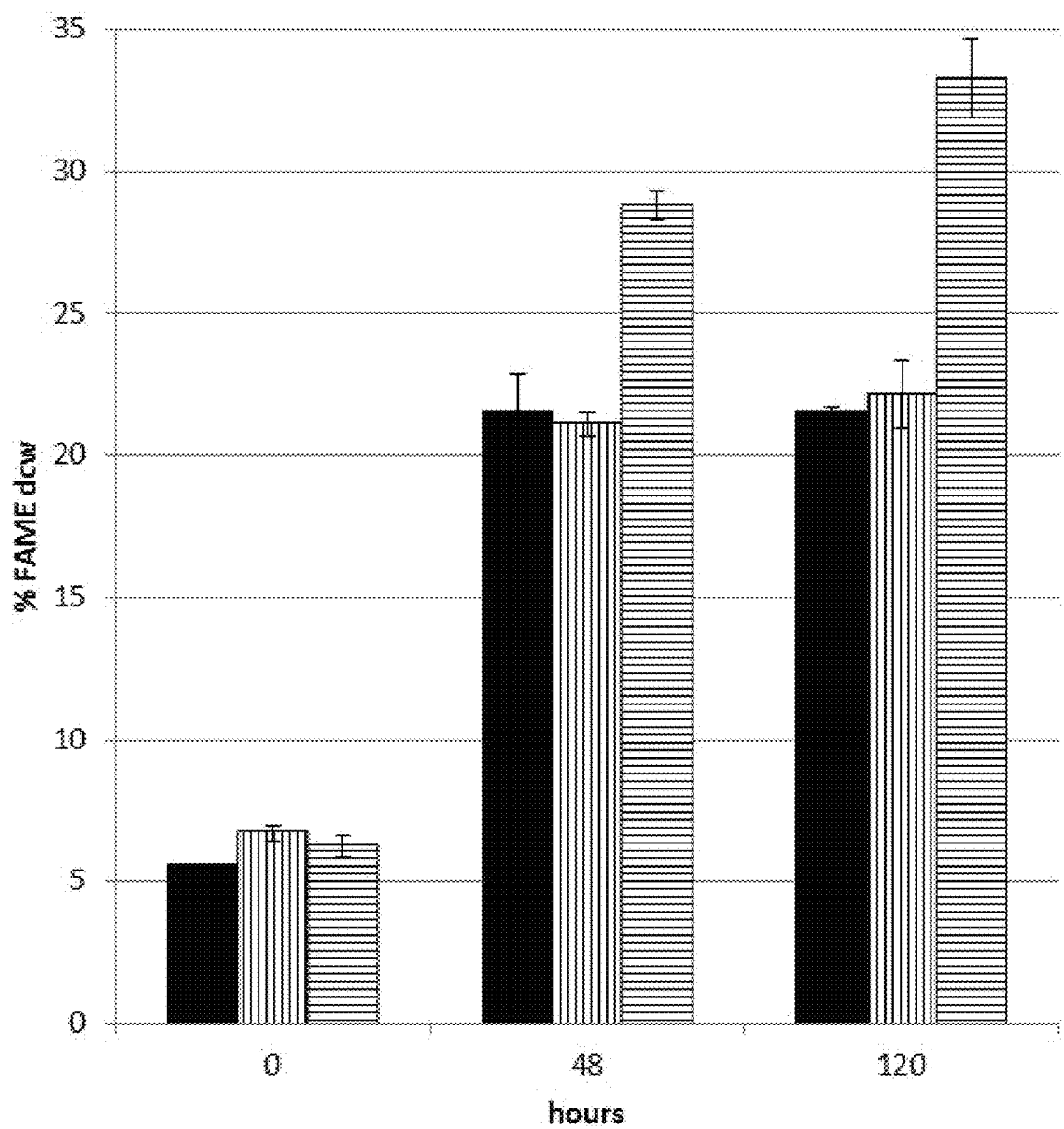
FIG. 13 shows (A) lipid production and (B) ethanol production, growth (optical density, $OD_{600}$), and glucose utilization (g/L) of *S. cerevisiae* strains in aerobic shake flasks. Strains shown in (A) are BFY692 (black bars), BFY692 with one copy of SNF1 (vertical stripes), and BFY692 with no copies of SNF1 (BFY709, horizontal stripes). In (B), optical densities are shown as solid lines, ethanol production as dotted lines, and glucose consumption as dashed lines. Strains shown in (B) are BFY692 (diamonds), BFY692 with one copy of SNF1 (squares), and BFY692 with no copies of SNF1 (BFY709, triangles).
Figure 13:
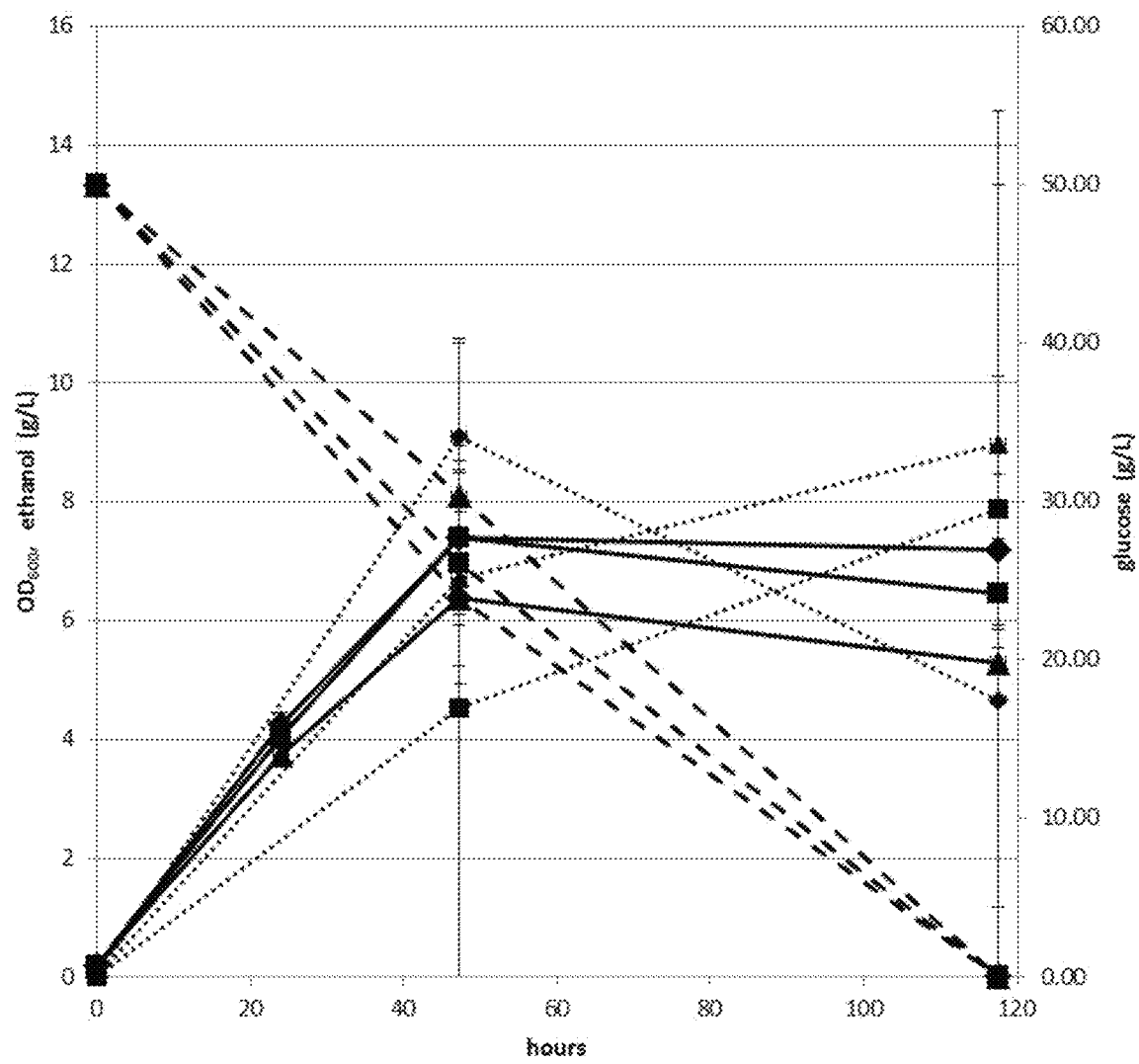

To realize an increase in lipid accumulation for SNF1 knockouts, both copies of SNF1 had to be ablated, as there was no intermediate response with only one copy of SNF1 (FIG. 13, panel A). In these conditions, one copy of SNF1 was adequate to perform its regulatory duties. The double SNF1 knock-out strain accumulates considerably more lipids than the parent and produces nearly the same amount of ethanol by the end of the fermentation (FIG. 13).

Glucose utilization and growth rates between the parent stain and the single or double SNF1 knock-out strains were similar, with the double Snf1 knock-out strain reaching a slightly lower $OD_{600}$ (FIG. 13, panel B). The lower cell density might be due to the funneling of more of the available carbon into lipid accumulation rather than cell growth in the double knockout strain. Though these were aerobic shake flasks, ethanol was produced (also later metabolized to some degree) showing that ethanol and lipids can be produced simultaneously. With the decrease in glycogen synthesis and β-oxidation and the increase in the acetyl-CoA pool due to the loss of SNF1 regulation of these pathways, a plausible mechanism for the increase in lipid accumulation is that carbon flux now funnels into the de novo lipid synthesis pathway while being protected from catabolism.

Figure 14:
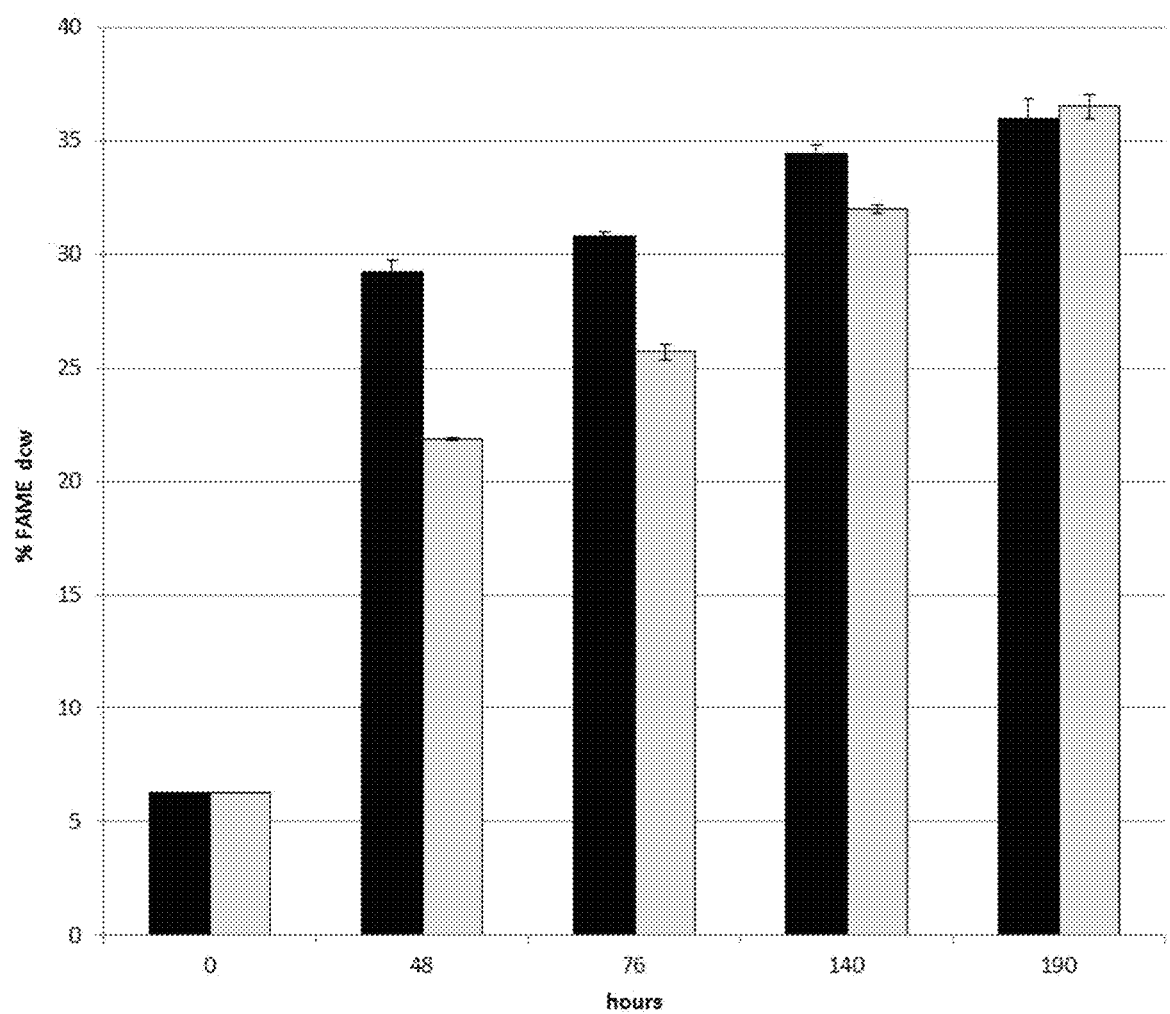
FIG. 14 shows (A) lipid production and (B) ethanol production (dotted lines), growth ($OD_{600}$, solid lines), and sugar utilization (g/L, dashed lines) by *S. cerevisiae* BFY709 in aerobic shake flasks from glucose (black bars in (A); triangles in (B)) or xylose (grey bars in (A); squares in (B)).
Figure 14:
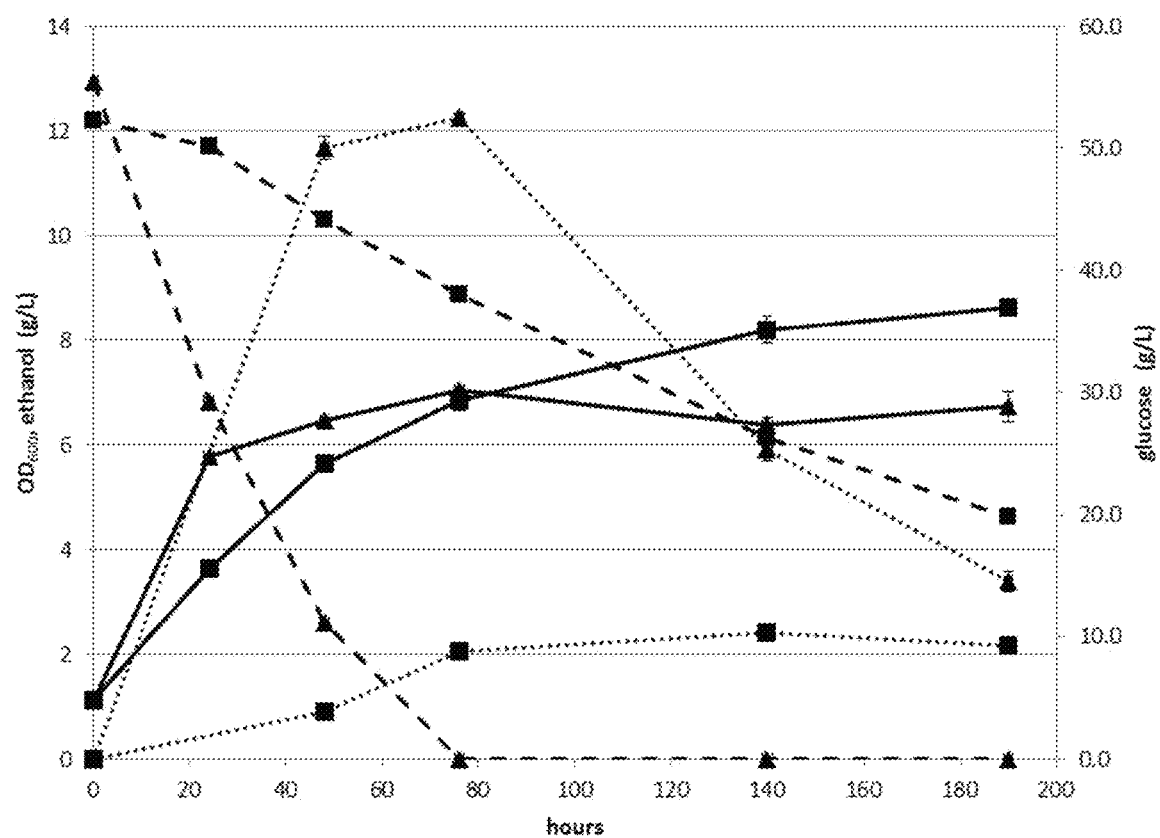

Strain BFY709 accumulated up to 36% FAME dcw from xylose as the sole carbon source (FIG. 14, panel A). The accumulation of lipids from xylose took longer than when grown on glucose while ethanol production from xylose was lower (FIG. 14, panel B). Up to 0.5 g/L xylitol was also produced when grown on xylose. Cell density was slightly higher when grown on xylose while the consumption of xylose was considerably slower than the consumption of glucose, with nearly half the xylose still present after 190 hours of incubation. These data suggest that carbon liberated from xylose is first shunted to lipid synthesis with ethanol production being secondary. In addition, ethanol production appears to cease while internal lipids continue to increase after 80 hours. However, with aerobic flasks, it is not possible to determine how much ethanol metabolism is occurring and thus reducing accumulation in the media, though this is unlikely as xylose continues to decrease linearly.

Strains BFY742 and BFY748 (engineered to express exogenous S. cerevisiae DGA and L. starkeyi DGA, respectively) demonstrated improved lipid production in comparison to strain BFY709. As shown in FIG. 15, strains BFY742 and BFY748 both accumulated over 43% FAME dcw from xylose as the sole carbon source, compared to approximately 30% FAME dcw for strain BFY709. These levels of lipids could be achieved by growth at either 30° C. or 37° C. Strains disclosed herein may also be cultured at 42° C. (or any temperature between 30° C. and 42° C. to achieve lipid production.

Lipid and ethanol co-production was further investigated in pH and aeration controlled fermenters. Fermenters with pH controlled at 5.2 and dissolved oxygen controlled at 10% contained YNB media with either low (5 mM) or high (35 mM) NH$_4$ concentration, or a rich media (YPD) and were inoculated with BFY709 cells. The results shown in FIG. 16 indicate rapid utilization of glucose with production of ethanol. Lipids accumulated only to 20% dcw in the low NH$_4$ medium, lower than the 34% lipids dcw that accumulated in the shake flasks.

Controlling dissolved oxygen at 10% may have negatively impacted both the ethanol titer and lipid accumulation. Dissolved oxygen content in 250 ml non-baffled shake flasks during growth of *S. cerevisiae* typically drops from near 100% to less than 10% down to undetectable levels for volumes of 50 ml at 350 rpm and 75 ml at 250 rpm, respectively. Sampling of shake flasks also causes a precipitous drop in dissolved oxygen. Thus control of dissolved oxygen concentration may prove necessary for effective lipid accumulation and is at odds with ethanol production. Maximum ethanol production is favored in anaerobic fermentations while lipid production is typically an aerobic process thus, if both products are desired, ethanol may need to be stripped off and recovered during an aerobic fermentation.

Example 5

Analytical Methods

Concentrations of sugars and ethanol were measured using a high performance liquid chromatograph (HPLC) equipped with HP refractive index detectors (Agilent Technologies, Palo Alto, Calif.). A Bio-Rad HPX-87H organic acids column and H+ guard column (BioRad Laboratories, Hercules, Calif.) operated at 55° C. The eluent was 0.01 N H$_2$SO$_4$ at a flow rate of 0.6 mL min$^{-1}$. Samples and standards were filtered through 0.45 mm nylon membrane syringe filters (Pall Corp., East Hills, N.Y.) prior to injection onto the column. Ammonium concentrations were determined using a YSI 7100 multi-parameter bioanalytical system.

Intracellular lipid accumulation was measured as fatty acid methyl esters (FAMEs) after in situ transesterification of the endogenous lipids to FAME, followed by GC analysis determined as follows: 7 to 10 mg of lyophilized microbial biomass (dried overnight at 40° C. under vacuum) was homogenized with 0.2 mL of chloroform:methanol (2:1 v/v), and the resulting solubilized lipids were transesterified in situ with 0.3 mL of HCl:methanol (5%, v/v) for one hour at 85° C. in the presence of tridecanoic acid (C13) methyl ester as an internal standard. FAMEs were extracted with 1 ml of hexane at room temperature for one hour and analyzed by gas chromatography:flame ionization detection (GC:FID) on an Agilent (Santa Clara, Calif., USA) 6890N with a DB-WAX column with dimensions 30 m×0.25 mm i.d. and 0.25 µm film thickness. Individual fatty acids were identified by mass spectrometry for the location of the unsaturation of the fatty acid positional isomers. The FAMEs were quantified based on a 37-FAME calibration mixture (Supelco, certified reference material, CRM47885, Sigma-Aldrich, St. Louis, Mo., USA) after normalizing for the internal standard. The sum of the individual fatty acids was calculated and expressed as weight % of dry biomass.

Example 6

Imaging

Images were acquired by staining a 100 µl cell suspension in water with 1 µl of Nile Red dissolved in acetone at 250 µg/ml. Cells and stain were allowed to incubate for 5 minutes prior to imaging. Images were collected on a Nikon epifluorescent microscope with 100× objective. Cells were illuminated by a mercury lamp and a 480/40 excitation and 505 long pass emission filter set.

To visualize the internal lipids, Nile Red was used to stain lipid vesicles within the cells after 72 hours of growth on glucose or xylose (FIG. 17). Side-by-side images display two different focal planes within the same cells showing that multiple levels of lipid vesicles exist throughout the cells, but there were no large differences in lipid vesicle size, number, or distribution observed between cells grown on glucose or xylose.

Example 7

Fatty Acid Profiles

Figure 18:
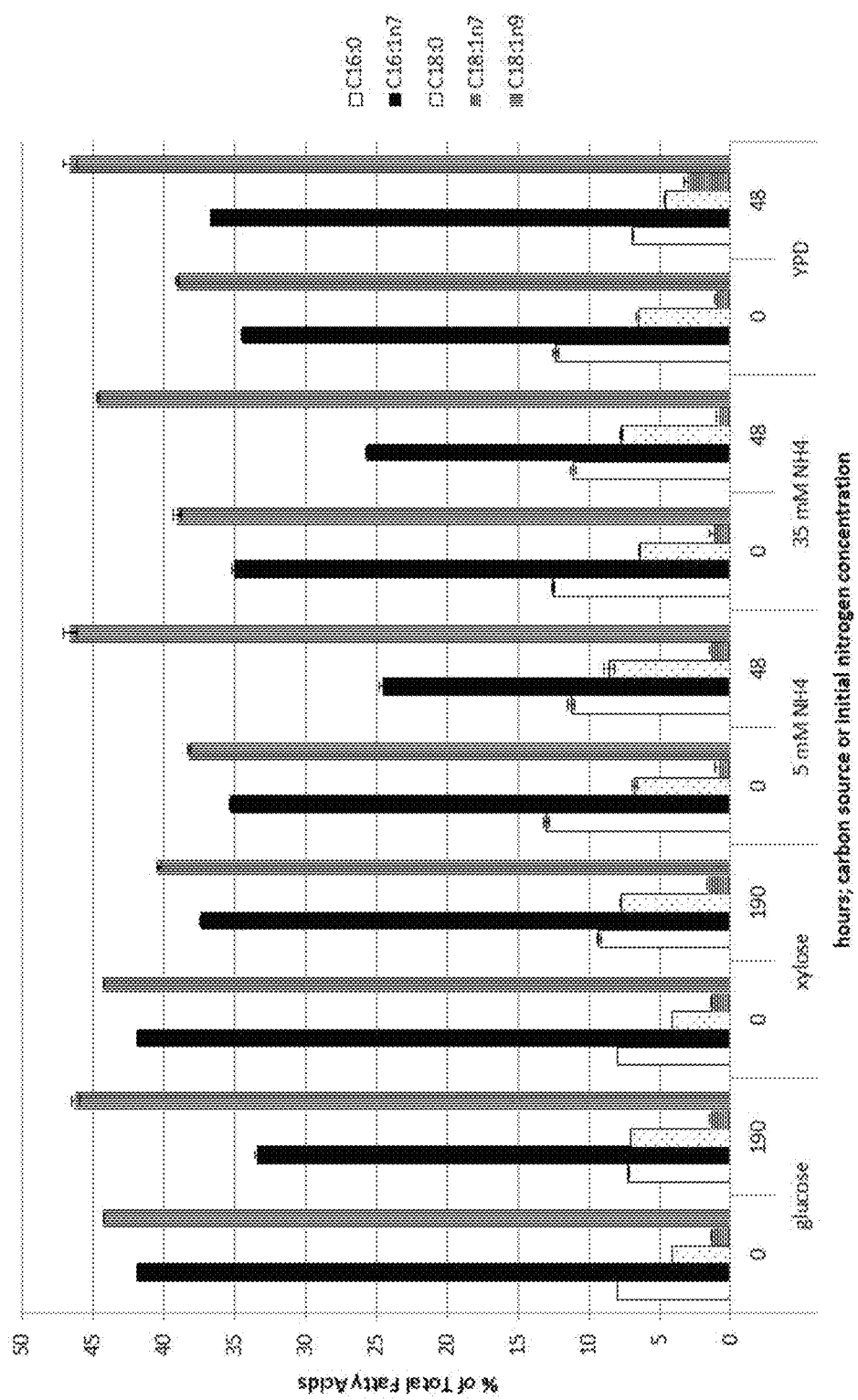
FIG. 18 shows changes in fatty acid speciation in different media as lipid accumulation occurs.
Figure 19:
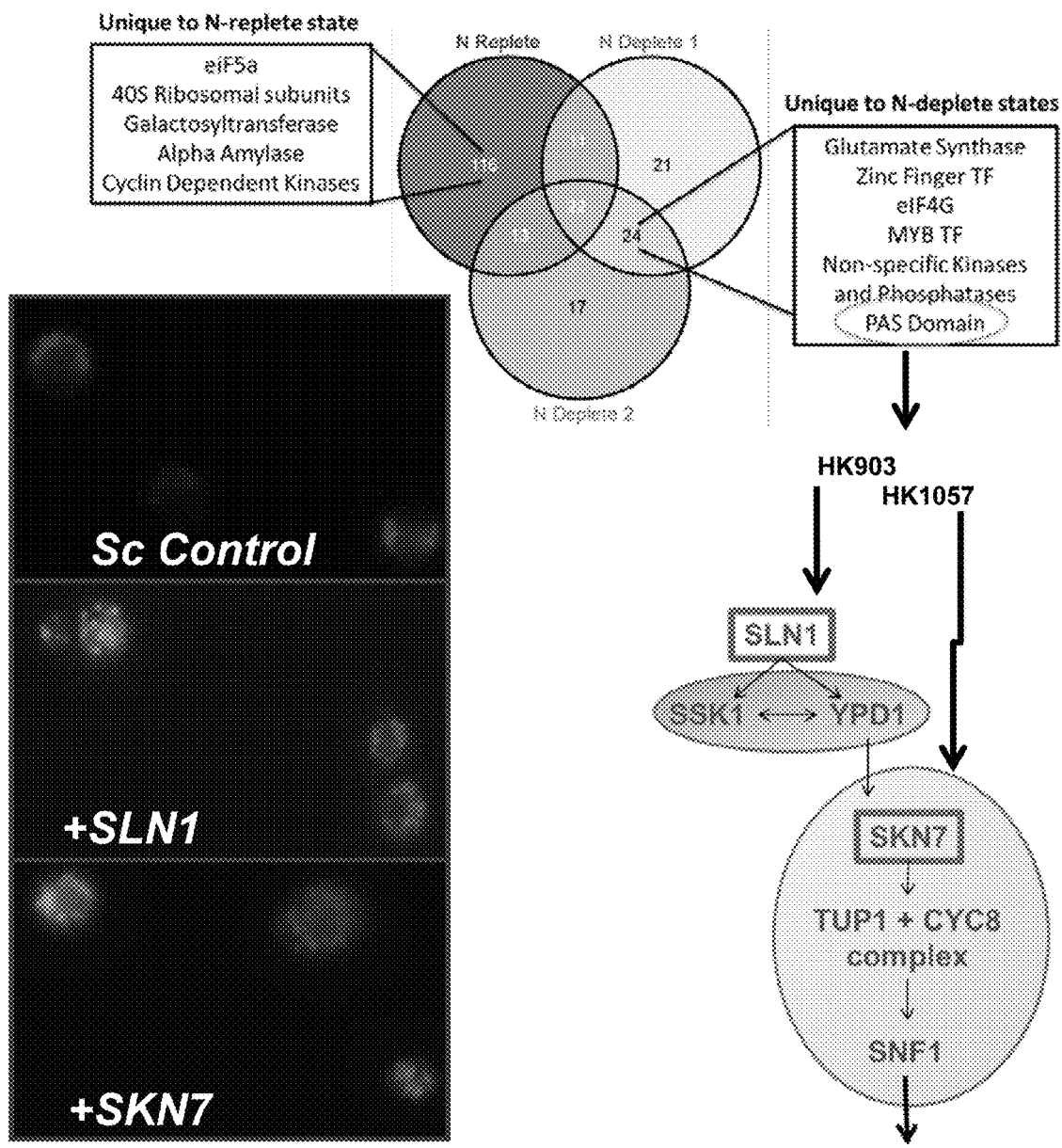
FIG. 19 shows algal protein phosphorylation and practical applications thereof. PAS domain (signal sensor) containing proteins were identified under N-deplete conditions and are found in histidine kinases of TCS phosphoregulatory systems. Over-expression of SLN1 in *S. cerevisiae* increased lipid content as measured by lipid extraction FAME analysis.

The distribution of fatty acids changed over the course of the fermentations. In all, 21 different fatty acids species were found yet only 5 fatty acid species, C16:0 (palmitic), C16:1n7 (palmitoleic), C18:0 (stearic), C18:1n7 (oleic), and C18:1n9 (vaccenic), made up greater than 94% of the total fatty acids (FIG. 18). Over the course of the fermentations, when glucose was the sole carbon source in YNB (defined) media, C16:1n7 decreased, C18:0 and C18:1n9 increased, and C16:0 and C18:1n7 acids did not change appreciably. When YPD, a rich medium, was used as the fermentation medium, C16:0 and C18:0 decreased, C16:1n7, C18:1n7, and C18:1n9 increased, signaling a shift from saturated to unsaturated fatty acid species. In contrast, when xylose was the sole carbon source on YNB media, C16:1n7 and C18:1n9 decreased, C16:0 and C18:0 increased, while C18:1n7 remained unchanged, signaling a small shift from unsaturated to saturated.

Aeration did not greatly alter the fatty acid speciation. Aerobic shake flasks and fermenters having only 10% dissolved oxygen showed identical changes in fatty acid speciation on YNB medium. These fatty acid speciation data agrees with previously reported values of C16:1 and C18:1 being the main species present, up greater than 72% of TAGs, with C16:0 and C18:0 making up the bulk of the remainder. The fatty acid speciation was different from that of oleaginous yeast of the Lipomyceteceae family in that C16:0 was typically between 15-50% whereas C16:1 was typically less than 10% for the majority of the strains with the exception of some species of Myxozyma. These fatty acid engineering efforts demonstrate the potential to change levels of different species of the fatty acids present in cells, making possible designer ratios of lipids and fatty acid chain lengths as well as efforts to produce free fatty acids, fatty alcohols, and fatty acid ethyl esters.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

We claim:

1. An engineered yeast cell, comprising exogenously added genes encoding xylose reductase, xylitol dehydrogenase and xylulose kinase enzymes; wherein a snf1 gene of the yeast cell has been ablated; and wherein the yeast cell has been modified to express the GAL2 transporter in the presence of glucose; and
further comprising a genetic modification that allows for overexpression of a diacylglycerol acyltransferase; and wherein the yeast cell is strain BFY709.

2. The yeast cell of claim 1, wherein the xylose reductase and xylitol dehydrogenase enzymes are from *Pichia stipitis*.

3. The yeast cell of claim 2, wherein the xylose reductase and xylitol dehydrogenase enzymes are XYL1 and XYL2.

4. The yeast cell of claim 1, wherein the xylulose kinase enzyme is *S. cerevisiae* XKS1.

5. The yeast cell of claim 1, wherein the modification to express the GAL2 transporter in the presence of glucose is the ablation of at least one copy of a gene encoding a GAL80 protein.

6. The yeast cell of claim 1, wherein the yeast cell accumulates at least 25% dry cell weight lipids when cultured in the presence of sugars.

7. The yeast cell of claim 6, wherein the yeast cell produces ethanol when cultured in the presence of sugars.

8. The yeast cell of claim 1, further comprising a genetic modification that allows for overexpression of a gene in the SLN1-YPD1-SKN7/SSK1 two-component regulatory system.

9. The yeast cell of claim 8, wherein the gene in the SLN1-YPD1-SKN7/SSK1 two-component regulatory system is a histidine kinase.

10. The yeast cell of claim 8, wherein the gene in the SLN1-YPD1-SKN7/SSK1 two-component regulatory system is SLN1 or SKN7.

11. A method for producing lipids or ethanol, comprising:
a) culturing the yeast cell of claim 1 with a source of sugar; and
b) recovering the lipids or ethanol from the culture.

12. The method of claim 11, wherein the source of sugar is lignocellulosic biomass that has been subjected to enzymatic treatment to produce sugars.

13. An engineered yeast cell, comprising exogenously added genes encoding xylose reductase, xylitol dehydrogenase and xylulose kinase enzymes; wherein the snf1 gene of the yeast cell has been ablated; and wherein the yeast cell has been modified to express the GAL2 transporter in the presence of glucose, further comprising a genetic modification that allows for overexpression of a diacylglycerol acyltransferase; and wherein the diacylglycerol acyltransferase is DGA1 from *S. cerevisiae* or *L. starkeyi*; and wherein the cell is the strain BFY742 or BFY748.

14. The yeast cell of claim 13, wherein the xylose reductase and xylitol dehydrogenase enzymes are from *Pichia stipitis*.

15. The yeast cell of claim 14, wherein the xylose reductase and xylitol dehydrogenase enzymes are XYL1 and XYL2.

16. The yeast cell of claim 13, wherein the xylulose kinase enzyme is *S. cerevisiae* XKS1.

17. The yeast cell of claim 13, wherein the modification to express the GAL2 transporter in the presence of glucose is the ablation of at least one copy of a gene encoding a GAL80 protein.

18. The yeast cell of claim 13, wherein the yeast cell accumulates at least 25% dry cell weight lipids when cultured in the presence of sugars.

19. The yeast cell of claim 18, wherein the yeast cell produces ethanol when cultured in the presence of sugars.

20. The yeast cell of claim 13, further comprising a genetic modification that allows for overexpression of a gene in the SLN1-YPD1-SKN7/SSK1 two-component regulatory system.

21. The yeast cell of claim 20, wherein the gene in the SLN1-YPD1-SKN7/SSK1 two-component regulatory system is a histidine kinase.

22. The yeast cell of claim 20, wherein the gene in the SLN1-YPD1-SKN7/SSK1 two-component regulatory system is SLN1 or SKN7.

* * * * *

SEQUENCE LISTING

<160> NUMBER OF SEQ ID NOS: 20

<210> SEQ ID NO 1
<211> LENGTH: 954
<212> TYPE: DNA
<213> ORGANISM: Pichia stipitis
<220> FEATURE:
<221> NAME/KEY: CDS
<222> LOCATION: (1)..(954)

<400> SEQUENCE: 1

```
atg cct tct att aag ttg aac tct ggt tac gac atg cca gcc gtc ggt      48
Met Pro Ser Ile Lys Leu Asn Ser Gly Tyr Asp Met Pro Ala Val Gly
1               5                   10                  15 ttc ggc tgt tgg aaa gtc gac gtc gac acc tgt tct gaa cag atc tac      96
Phe Gly Cys Trp Lys Val Asp Val Asp Thr Cys Ser Glu Gln Ile Tyr
            20                  25                  30 cgt gct atc aag acc ggt tac aga ttg ttc gac ggt gcc gaa gat tac     144
Arg Ala Ile Lys Thr Gly Tyr Arg Leu Phe Asp Gly Ala Glu Asp Tyr
        35                  40                  45 gcc aac gaa aag tta gtt ggt gcc ggt gtc aag aag gcc att gac gaa     192
Ala Asn Glu Lys Leu Val Gly Ala Gly Val Lys Lys Ala Ile Asp Glu
    50                  55                  60 ggt atc gtc aag cgt gaa gac ttg ttc ctt acc tcc aag ttg tgg aac     240
Gly Ile Val Lys Arg Glu Asp Leu Phe Leu Thr Ser Lys Leu Trp Asn
65                  70                  75                  80 aac tac cac cac cca gac aac gtc gaa aag gcc ttg aac aga acc ctt     288
Asn Tyr His His Pro Asp Asn Val Glu Lys Ala Leu Asn Arg Thr Leu
                85                  90                  95 tct gac ttg caa gtt gac tac gtt gac ttg ttc ttg atc cac ttc cca     336
Ser Asp Leu Gln Val Asp Tyr Val Asp Leu Phe Leu Ile His Phe Pro
            100                 105                 110 gtc acc ttc aag ttc gtt cca tta gaa gaa aag tac cca cca gga ttc     384
Val Thr Phe Lys Phe Val Pro Leu Glu Glu Lys Tyr Pro Pro Gly Phe
        115                 120                 125 tac tgt ggt aag ggt gac aac ttc gac tac gaa gat gtt cca att tta     432
Tyr Cys Gly Lys Gly Asp Asn Phe Asp Tyr Glu Asp Val Pro Ile Leu
    130                 135                 140 gag acc tgg aag gct ctt gaa aag ttg gtc aag gcc ggt aag atc aga     480
Glu Thr Trp Lys Ala Leu Glu Lys Leu Val Lys Ala Gly Lys Ile Arg
145                 150                 155                 160 tct atc ggt gtt tct aac ttc cca ggt gct ttg ctc ttg gac ttg ttg     528
Ser Ile Gly Val Ser Asn Phe Pro Gly Ala Leu Leu Leu Asp Leu Leu
                165                 170                 175 aga ggt gct acc atc aag cca tct gtc ttg caa gtt gaa cac cac cca     576
Arg Gly Ala Thr Ile Lys Pro Ser Val Leu Gln Val Glu His His Pro
            180                 185                 190 tac ttg caa caa cca aga ttg atc gaa ttc gct caa tcc cgt ggt att     624
Tyr Leu Gln Gln Pro Arg Leu Ile Glu Phe Ala Gln Ser Arg Gly Ile
        195                 200                 205 gct gtc acc gct tac tct tcg ttc ggt cct caa tct ttc gtt gaa ttg     672
Ala Val Thr Ala Tyr Ser Ser Phe Gly Pro Gln Ser Phe Val Glu Leu
    210                 215                 220 aac caa ggt aga gct ttg aac act tct cca ttg ttc gag aac gaa act     720
Asn Gln Gly Arg Ala Leu Asn Thr Ser Pro Leu Phe Glu Asn Glu Thr
225                 230                 235                 240 atc aag gct atc gct gct aag cac ggt aag tct cca gct caa gtc ttg     768
Ile Lys Ala Ile Ala Ala Lys His Gly Lys Ser Pro Ala Gln Val Leu
                245                 250                 255 ttg aga tgg tct tcc caa aga ggc att gcc atc att cca aag tcc aac     816
Leu Arg Trp Ser Ser Gln Arg Gly Ile Ala Ile Ile Pro Lys Ser Asn
```

```
                     260                 265                 270
act gtc cca aga ttg ttg gaa aac aag gac gtc aac agc ttc gac ttg      864
Thr Val Pro Arg Leu Leu Glu Asn Lys Asp Val Asn Ser Phe Asp Leu
        275                 280                 285 gac gaa caa gat ttc gct gac att gcc aag ttg gac atc aac ttg aga      912
Asp Glu Gln Asp Phe Ala Asp Ile Ala Lys Leu Asp Ile Asn Leu Arg
290                 295                 300 ttc aac gac cca tgg gac tgg gac aag att cct atc ttc gtc              954
Phe Asn Asp Pro Trp Asp Trp Asp Lys Ile Pro Ile Phe Val
305                 310                 315
```

<210> SEQ ID NO 2
<211> LENGTH: 318
<212> TYPE: PRT
<213> ORGANISM: Pichia stipitis

<400> SEQUENCE: 2

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300
```

```
                                        Phe Asn Asp Pro Trp Asp Trp Asp Lys Ile Pro Ile Phe Val
                                        305                 310                 315

<210> SEQ ID NO 3
<211> LENGTH: 1089
<212> TYPE: DNA
<213> ORGANISM: Pichia stipitis
<220> FEATURE:
<221> NAME/KEY: CDS
<222> LOCATION: (1)..(1089)

<400> SEQUENCE: 3 atg act gct aac cct tcc ttg gtg ttg aac aag atc gac gac att tcg        48
Met Thr Ala Asn Pro Ser Leu Val Leu Asn Lys Ile Asp Asp Ile Ser
1               5                   10                  15 ttc gaa act tac gat gcc cca gaa atc tct gaa cct acc gat gtc ctc        96
Phe Glu Thr Tyr Asp Ala Pro Glu Ile Ser Glu Pro Thr Asp Val Leu
                20                  25                  30 gtc cag gtc aag aaa acc ggt atc tgt ggt tcc gac atc cac ttc tac       144
Val Gln Val Lys Lys Thr Gly Ile Cys Gly Ser Asp Ile His Phe Tyr
            35                  40                  45 gcc cat ggt aga atc ggt aac ttc gtt ttg acc aag cca atg gtc ttg       192
Ala His Gly Arg Ile Gly Asn Phe Val Leu Thr Lys Pro Met Val Leu
        50                  55                  60 ggt cac gaa tcc gcc ggt act gtt gtc cag gtt ggt aag ggt gtc acc       240
Gly His Glu Ser Ala Gly Thr Val Val Gln Val Gly Lys Gly Val Thr
65                  70                  75                  80 tct ctt aag gtt ggt gac aac gtc gct atc gaa cca ggt att cca tcc       288
Ser Leu Lys Val Gly Asp Asn Val Ala Ile Glu Pro Gly Ile Pro Ser
                85                  90                  95 aga ttc tcc gac gaa tac aag agc ggt cac tac aac ttg tgt cct cac       336
Arg Phe Ser Asp Glu Tyr Lys Ser Gly His Tyr Asn Leu Cys Pro His
                100                 105                 110 atg gcc ttc gcc gct act cct aac tcc aag gaa ggc gaa cca aac cca       384
Met Ala Phe Ala Ala Thr Pro Asn Ser Lys Glu Gly Glu Pro Asn Pro
            115                 120                 125 cca ggt acc tta tgt aag tac ttc aag tcg cca gaa gac ttc ttg gtc       432
Pro Gly Thr Leu Cys Lys Tyr Phe Lys Ser Pro Glu Asp Phe Leu Val
        130                 135                 140 aag ttg cca gac cac gtc agc ttg gaa ctc ggt gct ctt gtt gag cca       480
Lys Leu Pro Asp His Val Ser Leu Glu Leu Gly Ala Leu Val Glu Pro
145                 150                 155                 160 ttg tct gtt ggt gtc cac gcc tct aag ttg ggt tcc gtt gct ttc ggc       528
Leu Ser Val Gly Val His Ala Ser Lys Leu Gly Ser Val Ala Phe Gly
                165                 170                 175 gac tac gtt gcc gtc ttt ggt gct ggt cct gtt ggt ctt ttg gct gct       576
Asp Tyr Val Ala Val Phe Gly Ala Gly Pro Val Gly Leu Leu Ala Ala
            180                 185                 190 gct gtc gcc aag acc ttc ggt gct aag ggt gtc atc gtc gtt gac att       624
Ala Val Ala Lys Thr Phe Gly Ala Lys Gly Val Ile Val Val Asp Ile
        195                 200                 205 ttc gac aac aag ttg aag atg gcc aag gac att ggt gct gct act cac       672
Phe Asp Asn Lys Leu Lys Met Ala Lys Asp Ile Gly Ala Ala Thr His
        210                 215                 220 acc ttc aac tcc aag acc ggt ggt tct gaa gaa ttg atc aag gct ttc       720
Thr Phe Asn Ser Lys Thr Gly Gly Ser Glu Glu Leu Ile Lys Ala Phe
225                 230                 235                 240 ggt ggt aac gtg cca aac gtc gtt ttg gaa tgt act ggt gct gaa cct       768
Gly Gly Asn Val Pro Asn Val Val Leu Glu Cys Thr Gly Ala Glu Pro
                245                 250                 255 tgt atc aag ttg ggt gtt gac gcc att gcc cca ggt ggt cgt ttc gtt       816
```

```
Cys Ile Lys Leu Gly Val Asp Ala Ile Ala Pro Gly Gly Arg Phe Val
            260                 265                 270 caa gtc ggt aac gct gct ggt cca gtc agc ttc cca atc acc gtt ttc       864
Gln Val Gly Asn Ala Ala Gly Pro Val Ser Phe Pro Ile Thr Val Phe
            275                 280                 285 gcc atg aag gaa ttg act ttg ttc ggt tct ttc aga tac gga ttc aac       912
Ala Met Lys Glu Leu Thr Leu Phe Gly Ser Phe Arg Tyr Gly Phe Asn
            290                 295                 300 gac tac aag act gct gtt gga atc ttt gac act aac tac caa aac ggt       960
Asp Tyr Lys Thr Ala Val Gly Ile Phe Asp Thr Asn Tyr Gln Asn Gly
305                 310                 315                 320 aga gaa aat gct cca att gac ttt gaa caa ttg atc acc cac aga tac      1008
Arg Glu Asn Ala Pro Ile Asp Phe Glu Gln Leu Ile Thr His Arg Tyr
                325                 330                 335 aag ttc aag gac gct att gaa gcc tac gac ttg gtc aga gcc ggt aag      1056
Lys Phe Lys Asp Ala Ile Glu Ala Tyr Asp Leu Val Arg Ala Gly Lys
            340                 345                 350 ggt gct gtc aag tgt ctc att gac ggc cct gag                          1089
Gly Ala Val Lys Cys Leu Ile Asp Gly Pro Glu
            355                 360

<210> SEQ ID NO 4
<211> LENGTH: 363
<212> TYPE: PRT
<213> ORGANISM: Pichia stipitis

<400> SEQUENCE: 4

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240
```

-continued

```
Gly Gly Asn Val Pro Asn Val Val Leu Glu Cys Thr Gly Ala Glu Pro
            245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
            275                 280                 285

Ala Met Lys Glu Leu Thr Leu Phe Gly Ser Phe Arg Tyr Gly Phe Asn
            290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
            325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
            355                 360
```

```
<210> SEQ ID NO 5
<211> LENGTH: 1800
<212> TYPE: DNA
<213> ORGANISM: Saccharomyces cerevisiae
<220> FEATURE:
<221> NAME/KEY: CDS
<222> LOCATION: (1)..(1800)

<400> SEQUENCE: 5
```

| | | | | | | | | | | | | | | | | |
|---|---|---|---|---|---|---|---|---|---|---|---|---|---|---|---|---|
| atg | ttg | tgt | tca | gta | att | cag | aga | cag | aca | aga | gag | gtt | tcc | aac | aca | 48 |
| Met | Leu | Cys | Ser | Val | Ile | Gln | Arg | Gln | Thr | Arg | Glu | Val | Ser | Asn | Thr | |
| 1 | | | | 5 | | | | | 10 | | | | | 15 | | |
| atg | tct | tta | gac | tca | tac | tat | ctt | ggg | ttt | gat | ctt | tcg | acc | caa | caa | 96 |
| Met | Ser | Leu | Asp | Ser | Tyr | Tyr | Leu | Gly | Phe | Asp | Leu | Ser | Thr | Gln | Gln | |
| | | | 20 | | | | | 25 | | | | | 30 | | | |
| ctg | aaa | tgt | ctc | gcc | att | aac | cag | gac | cta | aaa | att | gtc | cat | tca | gaa | 144 |
| Leu | Lys | Cys | Leu | Ala | Ile | Asn | Gln | Asp | Leu | Lys | Ile | Val | His | Ser | Glu | |
| | | 35 | | | | | 40 | | | | | 45 | | | | |
| aca | gtg | gaa | ttt | gaa | aag | gat | ctt | ccg | cat | tat | cac | aca | aag | aag | ggt | 192 |
| Thr | Val | Glu | Phe | Glu | Lys | Asp | Leu | Pro | His | Tyr | His | Thr | Lys | Lys | Gly | |
| | 50 | | | | | 55 | | | | | 60 | | | | | |
| gtc | tat | ata | cac | ggc | gac | act | atc | gaa | tgt | ccc | gta | gcc | atg | tgg | tta | 240 |
| Val | Tyr | Ile | His | Gly | Asp | Thr | Ile | Glu | Cys | Pro | Val | Ala | Met | Trp | Leu | |
| 65 | | | | | 70 | | | | | 75 | | | | | 80 | |
| gag | gct | cta | gat | ctg | gtt | ctc | tcg | aaa | tat | cgc | gag | gct | aaa | ttt | cca | 288 |
| Glu | Ala | Leu | Asp | Leu | Val | Leu | Ser | Lys | Tyr | Arg | Glu | Ala | Lys | Phe | Pro | |
| | | | | 85 | | | | | 90 | | | | | 95 | | |
| ttg | aac | aaa | gtt | atg | gcc | gtc | tca | ggg | tcc | tgc | cag | cag | cac | ggg | tct | 336 |
| Leu | Asn | Lys | Val | Met | Ala | Val | Ser | Gly | Ser | Cys | Gln | Gln | His | Gly | Ser | |
| | | | 100 | | | | | 105 | | | | | 110 | | | |
| gtc | tac | tgg | tcc | tcc | caa | gcc | gaa | tct | ctg | tta | gag | caa | ttg | aat | aag | 384 |
| Val | Tyr | Trp | Ser | Ser | Gln | Ala | Glu | Ser | Leu | Leu | Glu | Gln | Leu | Asn | Lys | |
| | | 115 | | | | | 120 | | | | | 125 | | | | |
| aaa | ccg | gaa | aaa | gat | tta | ttg | cac | tac | gtg | agc | tct | gta | gca | ttt | gca | 432 |
| Lys | Pro | Glu | Lys | Asp | Leu | Leu | His | Tyr | Val | Ser | Ser | Val | Ala | Phe | Ala | |
| | 130 | | | | | 135 | | | | | 140 | | | | | |
| agg | caa | acc | gcc | ccc | aat | tgg | caa | gac | cac | agt | act | gca | aag | caa | tgt | 480 |
| Arg | Gln | Thr | Ala | Pro | Asn | Trp | Gln | Asp | His | Ser | Thr | Ala | Lys | Gln | Cys | |
| 145 | | | | | 150 | | | | | 155 | | | | | 160 | |
| caa | gag | ttt | gaa | gag | tgc | ata | ggt | ggg | cct | gaa | aaa | atg | gct | caa | tta | 528 |
| Gln | Glu | Phe | Glu | Glu | Cys | Ile | Gly | Gly | Pro | Glu | Lys | Met | Ala | Gln | Leu | |
| | | | | 165 | | | | | 170 | | | | | 175 | | |

-continued

| | |
|---|---|
| aca ggg tcc aga gcc cat ttt aga ttt act ggt cct caa att ctg aaa<br>Thr Gly Ser Arg Ala His Phe Arg Phe Thr Gly Pro Gln Ile Leu Lys<br>            180                    185                   190 | 576 |
| att gca caa tta gaa cca gaa gct tac gaa aaa aca aag acc att tct<br>Ile Ala Gln Leu Glu Pro Glu Ala Tyr Glu Lys Thr Lys Thr Ile Ser<br>     195                    200                   205 | 624 |
| tta gtg tct aat ttt ttg act tct atc tta gtg ggc cat ctt gtt gaa<br>Leu Val Ser Asn Phe Leu Thr Ser Ile Leu Val Gly His Leu Val Glu<br>210                    215                    220 | 672 |
| tta gag gag gca gat gcc tgt ggt atg aac ctt tat gat ata cgt gaa<br>Leu Glu Glu Ala Asp Ala Cys Gly Met Asn Leu Tyr Asp Ile Arg Glu<br>225                  230                    235               240 | 720 |
| aga aaa ttc agt gat gag cta cta cat cta att gat agt tct tct aag<br>Arg Lys Phe Ser Asp Glu Leu Leu His Leu Ile Asp Ser Ser Ser Lys<br>             245                   250               255 | 768 |
| gat aaa act atc aga caa aaa tta atg aga gca ccc atg aaa aat ttg<br>Asp Lys Thr Ile Arg Gln Lys Leu Met Arg Ala Pro Met Lys Asn Leu<br>                260                    265               270 | 816 |
| ata gcg ggt acc atc tgt aaa tat ttt att gag aag tac ggt ttc aat<br>Ile Ala Gly Thr Ile Cys Lys Tyr Phe Ile Glu Lys Tyr Gly Phe Asn<br>             275                   280               285 | 864 |
| aca aac tgc aag gtc tct ccc atg act ggg gat aat tta gcc act ata<br>Thr Asn Cys Lys Val Ser Pro Met Thr Gly Asp Asn Leu Ala Thr Ile<br>290                    295                    300 | 912 |
| tgt tct tta ccc ctg cgg aag aat gac gtt ctc gtt tcc cta gga aca<br>Cys Ser Leu Pro Leu Arg Lys Asn Asp Val Leu Val Ser Leu Gly Thr<br>305                    310                    315               320 | 960 |
| agt act aca gtt ctt ctg gtc acc gat aag tat cac ccc tct ccg aac<br>Ser Thr Thr Val Leu Leu Val Thr Asp Lys Tyr His Pro Ser Pro Asn<br>                  325                    330               335 | 1008 |
| tat cat ctt ttc att cat cca act ctg cca aac cat tat atg ggt atg<br>Tyr His Leu Phe Ile His Pro Thr Leu Pro Asn His Tyr Met Gly Met<br>                   340                    345               350 | 1056 |
| att tgt tat tgt aat ggt tct ttg gca agg gag agg ata aga gac gag<br>Ile Cys Tyr Cys Asn Gly Ser Leu Ala Arg Glu Arg Ile Arg Asp Glu<br>             355                   360               365 | 1104 |
| tta aac aaa gaa cgg gaa aat aat tat gag aag act aac gat tgg act<br>Leu Asn Lys Glu Arg Glu Asn Asn Tyr Glu Lys Thr Asn Asp Trp Thr<br>370                    375                    380 | 1152 |
| ctt ttt aat caa gct gtg cta gat gac tca gaa agt agt gaa aat gaa<br>Leu Phe Asn Gln Ala Val Leu Asp Asp Ser Glu Ser Ser Glu Asn Glu<br>385                    390                    395               400 | 1200 |
| tta ggt gta tat ttt cct ctg ggg gag atc gtt cct agc gta aaa gcc<br>Leu Gly Val Tyr Phe Pro Leu Gly Glu Ile Val Pro Ser Val Lys Ala<br>                   405                    410               415 | 1248 |
| ata aac aaa agg gtt atc ttc aat cca aaa acg ggt atg att gaa aga<br>Ile Asn Lys Arg Val Ile Phe Asn Pro Lys Thr Gly Met Ile Glu Arg<br>             420                   425               430 | 1296 |
| gag gtg gcc aag ttc aaa gac aag agg cac gat gcc aaa aat att gta<br>Glu Val Ala Lys Phe Lys Asp Lys Arg His Asp Ala Lys Asn Ile Val<br>                  435                    440               445 | 1344 |
| gaa tca cag gct tta agt tgc agg gta aga ata tct ccc ctg ctt tcg<br>Glu Ser Gln Ala Leu Ser Cys Arg Val Arg Ile Ser Pro Leu Leu Ser<br>450                    455                    460 | 1392 |
| gat tca aac gca agc tca caa cag aga ctg aac gaa gat aca atc gtg<br>Asp Ser Asn Ala Ser Ser Gln Gln Arg Leu Asn Glu Asp Thr Ile Val<br>465                    470                    475               480 | 1440 |
| aag ttt gat tac gat gaa tct ccg ctg cgg gac tac cta aat aaa agg<br>Lys Phe Asp Tyr Asp Glu Ser Pro Leu Arg Asp Tyr Leu Asn Lys Arg | 1488 |

-continued

```
                485                 490                 495
cca gaa agg act ttt ttt gta ggt ggg gct tct aaa aac gat gct att    1536
Pro Glu Arg Thr Phe Phe Val Gly Gly Ala Ser Lys Asn Asp Ala Ile
            500                 505                 510 gtg aag aag ttt gct caa gtc att ggt gct aca aag ggt aat ttt agg    1584
Val Lys Lys Phe Ala Gln Val Ile Gly Ala Thr Lys Gly Asn Phe Arg
        515                 520                 525 cta gaa aca cca aac tca tgt gcc ctt ggt ggt tgt tat aag gcc atg    1632
Leu Glu Thr Pro Asn Ser Cys Ala Leu Gly Gly Cys Tyr Lys Ala Met
    530                 535                 540 tgg tca ttg tta tat gac tct aat aaa att gca gtt cct ttt gat aaa    1680
Trp Ser Leu Leu Tyr Asp Ser Asn Lys Ile Ala Val Pro Phe Asp Lys
545                 550                 555                 560 ttt ctg aat gac aat ttt cca tgg cat gta atg gaa agc ata tcc gat    1728
Phe Leu Asn Asp Asn Phe Pro Trp His Val Met Glu Ser Ile Ser Asp
                565                 570                 575 gtg gat aat gaa aat tgg gat cgc tat aat tcc aag att gtc ccc tta    1776
Val Asp Asn Glu Asn Trp Asp Arg Tyr Asn Ser Lys Ile Val Pro Leu
            580                 585                 590 agc gaa ctg gaa aag act ctc atc                                    1800
Ser Glu Leu Glu Lys Thr Leu Ile
        595                 600

<210> SEQ ID NO 6
<211> LENGTH: 600
<212> TYPE: PRT
<213> ORGANISM: Saccharomyces cerevisiae

<400> SEQUENCE: 6

Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220
```

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
            245                 250                 255

Asp Lys Thr Ile Arg Gln Lys Leu Met Arg Ala Pro Met Lys Asn Leu
        260                 265                 270

Ile Ala Gly Thr Ile Cys Lys Tyr Phe Ile Glu Lys Tyr Gly Phe Asn
    275                 280                 285

Thr Asn Cys Lys Val Ser Pro Met Thr Gly Asp Asn Leu Ala Thr Ile
290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
            340                 345                 350

Ile Cys Tyr Cys Asn Gly Ser Leu Ala Arg Glu Arg Ile Arg Asp Glu
        355                 360                 365

Leu Asn Lys Glu Arg Glu Asn Asn Tyr Glu Lys Thr Asn Asp Trp Thr
370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
                405                 410                 415

Ile Asn Lys Arg Val Ile Phe Asn Pro Lys Thr Gly Met Ile Glu Arg
            420                 425                 430

Glu Val Ala Lys Phe Lys Asp Lys Arg His Asp Ala Lys Asn Ile Val
        435                 440                 445

Glu Ser Gln Ala Leu Ser Cys Arg Val Arg Ile Ser Pro Leu Leu Ser
450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
                485                 490                 495

Pro Glu Arg Thr Phe Phe Val Gly Gly Ala Ser Lys Asn Asp Ala Ile
            500                 505                 510

Val Lys Lys Phe Ala Gln Val Ile Gly Ala Thr Lys Gly Asn Phe Arg
        515                 520                 525

Leu Glu Thr Pro Asn Ser Cys Ala Leu Gly Gly Cys Tyr Lys Ala Met
530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Asp Arg Tyr Asn Ser Lys Ile Val Pro Leu
            580                 585                 590

Ser Glu Leu Glu Lys Thr Leu Ile
        595                 600

<210> SEQ ID NO 7
<211> LENGTH: 1899
<212> TYPE: DNA
<213> ORGANISM: Saccharomyces cerevisiae
<220> FEATURE:

<221> NAME/KEY: CDS
<222> LOCATION: (1)..(1899)

<400> SEQUENCE: 7

```
atg agc agt aac aac aac aca aac aca gca cct gcc aat gca aat tct      48
Met Ser Ser Asn Asn Asn Thr Asn Thr Ala Pro Ala Asn Ala Asn Ser
1               5                   10                  15 agc cac cac cac cac cat cac cac cat cac cac cac cat cac ggt cat      96
Ser His His His His His His His His His His His His His Gly His
            20                  25                  30 ggc gga agc aac tcg acg cta aac aat ccc aag tcg tcc tta gcg gat     144
Gly Gly Ser Asn Ser Thr Leu Asn Asn Pro Lys Ser Ser Leu Ala Asp
        35                  40                  45 ggt gca cat atc ggg aac tac caa atc gtc aaa acg ctg gga gag ggg     192
Gly Ala His Ile Gly Asn Tyr Gln Ile Val Lys Thr Leu Gly Glu Gly
50                  55                  60 tcc ttt ggt aaa gtt aaa ttg gca tat cat acc act acg ggc caa aaa     240
Ser Phe Gly Lys Val Lys Leu Ala Tyr His Thr Thr Thr Gly Gln Lys
65                  70                  75                  80 gtt gct cta aaa atc att aat aag aag gtt ttg gca aag agt gat atg     288
Val Ala Leu Lys Ile Ile Asn Lys Lys Val Leu Ala Lys Ser Asp Met
            85                  90                  95 cag ggc aga att gaa aga gaa ata tct tat ctg aga ctc tta aga cac     336
Gln Gly Arg Ile Glu Arg Glu Ile Ser Tyr Leu Arg Leu Leu Arg His
        100                 105                 110 ccc cac atc atc aaa ctg tat gat gtt atc aaa tcc aaa gat gaa atc     384
Pro His Ile Ile Lys Leu Tyr Asp Val Ile Lys Ser Lys Asp Glu Ile
    115                 120                 125 att atg gtt ata gag tac gcc ggg aac gaa ttg ttt gac tat att gtt     432
Ile Met Val Ile Glu Tyr Ala Gly Asn Glu Leu Phe Asp Tyr Ile Val
130                 135                 140 cag aga gac aaa atg agc gag caa gag gca aga aga ttt ttc cag cag     480
Gln Arg Asp Lys Met Ser Glu Gln Glu Ala Arg Arg Phe Phe Gln Gln
145                 150                 155                 160 atc atc agt gcc gtc gag tac tgc cat agg cac aaa att gtc cat aga     528
Ile Ile Ser Ala Val Glu Tyr Cys His Arg His Lys Ile Val His Arg
                165                 170                 175 gat ctg aag cct gaa aac tta cta cta gat gag cat ctg aat gta aag     576
Asp Leu Lys Pro Glu Asn Leu Leu Leu Asp Glu His Leu Asn Val Lys
            180                 185                 190 att gcc gat ttt ggt ttg tca aac atc atg act gat ggt aat ttc tta     624
Ile Ala Asp Phe Gly Leu Ser Asn Ile Met Thr Asp Gly Asn Phe Leu
        195                 200                 205 aag act tct tgt ggt tct ccc aat tat gcg gct cct gaa gtt atc agc     672
Lys Thr Ser Cys Gly Ser Pro Asn Tyr Ala Ala Pro Glu Val Ile Ser
    210                 215                 220 ggt aag ctg tac gca ggc cca gaa gtg gac gtg tgg tca tgt ggg gtt     720
Gly Lys Leu Tyr Ala Gly Pro Glu Val Asp Val Trp Ser Cys Gly Val
225                 230                 235                 240 atc ctt tat gtt atg ctt tgt cgt cgt cta ccg ttt gac gat gaa agc     768
Ile Leu Tyr Val Met Leu Cys Arg Arg Leu Pro Phe Asp Asp Glu Ser
                245                 250                 255 atc cca gtg ctt ttc aag aat atc agc aac ggt gtt tac acc ttg cct     816
Ile Pro Val Leu Phe Lys Asn Ile Ser Asn Gly Val Tyr Thr Leu Pro
            260                 265                 270 aaa ttt tta tct cct gga gct gct ggg cta atc aaa aga atg tta atc     864
Lys Phe Leu Ser Pro Gly Ala Ala Gly Leu Ile Lys Arg Met Leu Ile
        275                 280                 285 gtt aat cca ttg aac aga ata agc att cat gaa att atg caa gac gat     912
Val Asn Pro Leu Asn Arg Ile Ser Ile His Glu Ile Met Gln Asp Asp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
|     |     | 290 |     |     |     |     | 295 |     |     |     |     | 300 |     |     |     |      |
| tgg | ttc | aaa | gtt | gac | ctg | cca | gaa | tat | cta | ctt | cca | cca | gat | ttg | aaa | 960  |
| Trp | Phe | Lys | Val | Asp | Leu | Pro | Glu | Tyr | Leu | Leu | Pro | Pro | Asp | Leu | Lys |      |
| 305 |     |     |     |     | 310 |     |     |     |     | 315 |     |     |     |     | 320 |      |
| cca | cac | cca | gaa | gaa | gag | aat | gaa | aat | aat | gac | tca | aaa | aag | gat | ggc | 1008 |
| Pro | His | Pro | Glu | Glu | Glu | Asn | Glu | Asn | Asn | Asp | Ser | Lys | Lys | Asp | Gly |      |
|     |     |     |     | 325 |     |     |     |     | 330 |     |     |     |     | 335 |     |      |
| agc | agc | cca | gat | aac | gat | gaa | att | gat | gac | aac | ctt | gtc | aat | att | tta | 1056 |
| Ser | Ser | Pro | Asp | Asn | Asp | Glu | Ile | Asp | Asp | Asn | Leu | Val | Asn | Ile | Leu |      |
|     |     |     | 340 |     |     |     |     | 345 |     |     |     |     | 350 |     |     |      |
| tca | tcg | acc | atg | ggt | tac | gaa | aaa | gac | gag | att | tat | gag | tcc | tta | gaa | 1104 |
| Ser | Ser | Thr | Met | Gly | Tyr | Glu | Lys | Asp | Glu | Ile | Tyr | Glu | Ser | Leu | Glu |      |
|     |     | 355 |     |     |     |     | 360 |     |     |     |     | 365 |     |     |     |      |
| tca | tca | gaa | gac | act | cct | gca | ttc | aac | gaa | att | agg | gac | gcg | tac | atg | 1152 |
| Ser | Ser | Glu | Asp | Thr | Pro | Ala | Phe | Asn | Glu | Ile | Arg | Asp | Ala | Tyr | Met |      |
| 370 |     |     |     |     | 375 |     |     |     |     | 380 |     |     |     |     |     |      |
| ttg | att | aag | gag | aat | aaa | tct | ttg | atc | aag | gat | atg | aag | gca | aac | aaa | 1200 |
| Leu | Ile | Lys | Glu | Asn | Lys | Ser | Leu | Ile | Lys | Asp | Met | Lys | Ala | Asn | Lys |      |
| 385 |     |     |     |     | 390 |     |     |     |     | 395 |     |     |     |     | 400 |      |
| agc | gtc | agt | gat | gaa | ctg | gat | acc | ttt | ctg | tcc | cag | tca | cct | cca | act | 1248 |
| Ser | Val | Ser | Asp | Glu | Leu | Asp | Thr | Phe | Leu | Ser | Gln | Ser | Pro | Pro | Thr |      |
|     |     |     |     | 405 |     |     |     |     | 410 |     |     |     |     | 415 |     |      |
| ttt | caa | caa | caa | agc | aaa | tcc | cat | caa | aag | agt | caa | gta | gat | cat | gaa | 1296 |
| Phe | Gln | Gln | Gln | Ser | Lys | Ser | His | Gln | Lys | Ser | Gln | Val | Asp | His | Glu |      |
|     |     |     | 420 |     |     |     |     | 425 |     |     |     |     | 430 |     |     |      |
| act | gcc | aag | caa | cac | gca | aga | agg | atg | gca | agt | gct | atc | act | caa | caa | 1344 |
| Thr | Ala | Lys | Gln | His | Ala | Arg | Arg | Met | Ala | Ser | Ala | Ile | Thr | Gln | Gln |      |
|     |     | 435 |     |     |     |     | 440 |     |     |     |     | 445 |     |     |     |      |
| agg | aca | tat | cac | caa | tca | ccc | ttc | atg | gat | cag | tat | aaa | gaa | gaa | gac | 1392 |
| Arg | Thr | Tyr | His | Gln | Ser | Pro | Phe | Met | Asp | Gln | Tyr | Lys | Glu | Glu | Asp |      |
| 450 |     |     |     |     | 455 |     |     |     |     | 460 |     |     |     |     |     |      |
| tct | aca | gtt | tcc | att | ttg | cct | aca | tct | tta | cct | cag | atc | cac | aga | gct | 1440 |
| Ser | Thr | Val | Ser | Ile | Leu | Pro | Thr | Ser | Leu | Pro | Gln | Ile | His | Arg | Ala |      |
| 465 |     |     |     |     | 470 |     |     |     |     | 475 |     |     |     |     | 480 |      |
| aat | atg | tta | gca | caa | ggt | tcg | cca | gct | gcc | tct | aaa | ata | tct | cct | ctt | 1488 |
| Asn | Met | Leu | Ala | Gln | Gly | Ser | Pro | Ala | Ala | Ser | Lys | Ile | Ser | Pro | Leu |      |
|     |     |     |     | 485 |     |     |     |     | 490 |     |     |     |     | 495 |     |      |
| gta | acg | aaa | aaa | tct | aaa | acg | aga | tgg | cat | ttt | ggt | ata | cga | tct | cgc | 1536 |
| Val | Thr | Lys | Lys | Ser | Lys | Thr | Arg | Trp | His | Phe | Gly | Ile | Arg | Ser | Arg |      |
|     |     |     | 500 |     |     |     |     | 505 |     |     |     |     | 510 |     |     |      |
| tca | tat | cca | tta | gac | gtt | atg | ggt | gaa | att | tat | att | gcc | ttg | aag | aat | 1584 |
| Ser | Tyr | Pro | Leu | Asp | Val | Met | Gly | Glu | Ile | Tyr | Ile | Ala | Leu | Lys | Asn |      |
|     |     | 515 |     |     |     |     | 520 |     |     |     |     | 525 |     |     |     |      |
| ttg | ggt | gcc | gaa | tgg | gcc | aag | cca | tct | gaa | gag | gat | tta | tgg | act | atc | 1632 |
| Leu | Gly | Ala | Glu | Trp | Ala | Lys | Pro | Ser | Glu | Glu | Asp | Leu | Trp | Thr | Ile |      |
| 530 |     |     |     |     | 535 |     |     |     |     | 540 |     |     |     |     |     |      |
| aaa | tta | agg | tgg | aaa | tat | gat | att | gga | aac | aag | aca | aac | act | aat | gaa | 1680 |
| Lys | Leu | Arg | Trp | Lys | Tyr | Asp | Ile | Gly | Asn | Lys | Thr | Asn | Thr | Asn | Glu |      |
| 545 |     |     |     |     | 550 |     |     |     |     | 555 |     |     |     |     | 560 |      |
| aaa | ata | cct | gat | tta | atg | aaa | atg | gta | att | caa | tta | ttt | caa | att | gaa | 1728 |
| Lys | Ile | Pro | Asp | Leu | Met | Lys | Met | Val | Ile | Gln | Leu | Phe | Gln | Ile | Glu |      |
|     |     |     |     | 565 |     |     |     |     | 570 |     |     |     |     | 575 |     |      |
| acc | aat | aat | tat | ttg | gtg | gat | ttc | aaa | ttt | gac | ggc | tgg | gaa | agt | agt | 1776 |
| Thr | Asn | Asn | Tyr | Leu | Val | Asp | Phe | Lys | Phe | Asp | Gly | Trp | Glu | Ser | Ser |      |
|     |     |     | 580 |     |     |     |     | 585 |     |     |     |     | 590 |     |     |      |
| tat | gga | gat | gat | act | act | gtt | tct | aat | att | tct | gaa | gat | gaa | atg | agt | 1824 |
| Tyr | Gly | Asp | Asp | Thr | Thr | Val | Ser | Asn | Ile | Ser | Glu | Asp | Glu | Met | Ser |      |
|     |     | 595 |     |     |     |     | 600 |     |     |     |     | 605 |     |     |     |      |
| act | ttt | tca | gcc | tac | cca | ttt | tta | cat | tta | aca | aca | aaa | cta | att | atg | 1872 |

```
Thr Phe Ser Ala Tyr Pro Phe Leu His Leu Thr Thr Lys Leu Ile Met
            610             615                 620 gaa tta gcc gtt aac agt caa agc aat                                    1899
Glu Leu Ala Val Asn Ser Gln Ser Asn
625                 630

<210> SEQ ID NO 8
<211> LENGTH: 633
<212> TYPE: PRT
<213> ORGANISM: Saccharomyces cerevisiae

<400> SEQUENCE: 8

Met Ser Ser Asn Asn Asn Thr Asn Thr Ala Pro Ala Asn Ala Asn Ser
1               5                   10                  15

Ser His His His His His His His His His His His His Gly His
            20                  25                  30

Gly Gly Ser Asn Ser Thr Leu Asn Asn Pro Lys Ser Ser Leu Ala Asp
            35                  40                  45

Gly Ala His Ile Gly Asn Tyr Gln Ile Val Lys Thr Leu Gly Glu Gly
    50                  55                  60

Ser Phe Gly Lys Val Lys Leu Ala Tyr His Thr Thr Thr Gly Gln Lys
65                  70                  75                  80

Val Ala Leu Lys Ile Ile Asn Lys Lys Val Leu Ala Lys Ser Asp Met
                85                  90                  95

Gln Gly Arg Ile Glu Arg Glu Ile Ser Tyr Leu Arg Leu Leu Arg His
            100                 105                 110

Pro His Ile Ile Lys Leu Tyr Asp Val Ile Lys Ser Lys Asp Glu Ile
        115                 120                 125

Ile Met Val Ile Glu Tyr Ala Gly Asn Glu Leu Phe Asp Tyr Ile Val
    130                 135                 140

Gln Arg Asp Lys Met Ser Glu Gln Glu Ala Arg Arg Phe Phe Gln Gln
145                 150                 155                 160

Ile Ile Ser Ala Val Glu Tyr Cys His Arg His Lys Ile Val His Arg
                165                 170                 175

Asp Leu Lys Pro Glu Asn Leu Leu Leu Asp Glu His Leu Asn Val Lys
            180                 185                 190

Ile Ala Asp Phe Gly Leu Ser Asn Ile Met Thr Asp Gly Asn Phe Leu
        195                 200                 205

Lys Thr Ser Cys Gly Ser Pro Asn Tyr Ala Ala Pro Glu Val Ile Ser
    210                 215                 220

Gly Lys Leu Tyr Ala Gly Pro Glu Val Asp Val Trp Ser Cys Gly Val
225                 230                 235                 240

Ile Leu Tyr Val Met Leu Cys Arg Arg Leu Pro Phe Asp Asp Glu Ser
                245                 250                 255

Ile Pro Val Leu Phe Lys Asn Ile Ser Asn Gly Val Tyr Thr Leu Pro
            260                 265                 270

Lys Phe Leu Ser Pro Gly Ala Ala Gly Leu Ile Lys Arg Met Leu Ile
        275                 280                 285

Val Asn Pro Leu Asn Arg Ile Ser Ile His Glu Ile Met Gln Asp Asp
    290                 295                 300

Trp Phe Lys Val Asp Leu Pro Glu Tyr Leu Leu Pro Pro Asp Leu Lys
305                 310                 315                 320

Pro His Pro Glu Glu Glu Asn Glu Asn Asn Asp Ser Lys Lys Asp Gly
                325                 330                 335

Ser Ser Pro Asp Asn Asp Glu Ile Asp Asp Asn Leu Val Asn Ile Leu
```

```
                    340                 345                 350
Ser Ser Thr Met Gly Tyr Glu Lys Asp Glu Ile Tyr Glu Ser Leu Glu
            355                 360                 365

Ser Ser Glu Asp Thr Pro Ala Phe Asn Glu Ile Arg Asp Ala Tyr Met
        370                 375                 380

Leu Ile Lys Glu Asn Lys Ser Leu Ile Lys Asp Met Lys Ala Asn Lys
385                 390                 395                 400

Ser Val Ser Asp Glu Leu Asp Thr Phe Leu Ser Gln Ser Pro Pro Thr
                405                 410                 415

Phe Gln Gln Gln Ser Lys Ser His Gln Lys Ser Gln Val Asp His Glu
            420                 425                 430

Thr Ala Lys Gln His Ala Arg Arg Met Ala Ser Ala Ile Thr Gln Gln
        435                 440                 445

Arg Thr Tyr His Gln Ser Pro Phe Met Asp Gln Tyr Lys Glu Glu Asp
    450                 455                 460

Ser Thr Val Ser Ile Leu Pro Thr Ser Leu Pro Gln Ile His Arg Ala
465                 470                 475                 480

Asn Met Leu Ala Gln Gly Ser Pro Ala Ala Ser Lys Ile Ser Pro Leu
                485                 490                 495

Val Thr Lys Lys Ser Lys Thr Arg Trp His Phe Gly Ile Arg Ser Arg
            500                 505                 510

Ser Tyr Pro Leu Asp Val Met Gly Glu Ile Tyr Ile Ala Leu Lys Asn
        515                 520                 525

Leu Gly Ala Glu Trp Ala Lys Pro Ser Glu Glu Asp Leu Trp Thr Ile
    530                 535                 540

Lys Leu Arg Trp Lys Tyr Asp Ile Gly Asn Lys Thr Asn Thr Asn Glu
545                 550                 555                 560

Lys Ile Pro Asp Leu Met Lys Met Val Ile Gln Leu Phe Gln Ile Glu
                565                 570                 575

Thr Asn Asn Tyr Leu Val Asp Phe Lys Phe Asp Gly Trp Glu Ser Ser
            580                 585                 590

Tyr Gly Asp Asp Thr Thr Val Ser Asn Ile Ser Glu Asp Glu Met Ser
        595                 600                 605

Thr Phe Ser Ala Tyr Pro Phe Leu His Leu Thr Thr Lys Leu Ile Met
    610                 615                 620

Glu Leu Ala Val Asn Ser Gln Ser Asn
625                 630

<210> SEQ ID NO 9
<211> LENGTH: 3660
<212> TYPE: DNA
<213> ORGANISM: Saccharomyces cerevisiae
<220> FEATURE:
<221> NAME/KEY: CDS
<222> LOCATION: (1)..(3660)

<400> SEQUENCE: 9 atg cga ttt ggc ctg cca tca aaa ttg gaa ctc act cct ccg ttt agg     48
Met Arg Phe Gly Leu Pro Ser Lys Leu Glu Leu Thr Pro Pro Phe Arg
1               5                   10                  15 ata ggc atc cga act caa cta acg gca cta gtt agt ata gtg gct ttg     96
Ile Gly Ile Arg Thr Gln Leu Thr Ala Leu Val Ser Ile Val Ala Leu
                20                  25                  30 ggc tca ctg att att ctg gct gta acg aca ggg gtc tat ttt acc tcg    144
Gly Ser Leu Ile Ile Leu Ala Val Thr Thr Gly Val Tyr Phe Thr Ser
            35                  40                  45
```

-continued

| | | |
|---|---|---|
| aac tat aaa aat tta agg tcc gat aga ctg tac att gcc gct cag tta<br>Asn Tyr Lys Asn Leu Arg Ser Asp Arg Leu Tyr Ile Ala Ala Gln Leu<br>50                        55                      60 | | 192 |
| aag tca tca cag att gac caa act cta aac tac tta tat tac cag gcg<br>Lys Ser Ser Gln Ile Asp Gln Thr Leu Asn Tyr Leu Tyr Tyr Gln Ala<br>65                        70                      75                      80 | | 240 |
| tac tat ttg gca tca aga gac gcc ctg caa agc tca cta aca agt tac<br>Tyr Tyr Leu Ala Ser Arg Asp Ala Leu Gln Ser Ser Leu Thr Ser Tyr<br>                  85                      90                      95 | | 288 |
| gtt gca ggt aac aag agt gca gat aat tgg gta gat tcc ttg agt gtg<br>Val Ala Gly Asn Lys Ser Ala Asp Asn Trp Val Asp Ser Leu Ser Val<br>                  100                    105                    110 | | 336 |
| att caa aaa ttt ttg agc tct tca aac ttg ttt tat gtt gct aaa gtt<br>Ile Gln Lys Phe Leu Ser Ser Ser Asn Leu Phe Tyr Val Ala Lys Val<br>                  115                    120                    125 | | 384 |
| tac gat tct tca ttt aat gct gtt ttg aac gct acg aat aat gga act<br>Tyr Asp Ser Ser Phe Asn Ala Val Leu Asn Ala Thr Asn Asn Gly Thr<br>130                        135                    140 | | 432 |
| ggt gat cta att cca gaa gat gtt tta gac agt ttg ttc cca tta tcc<br>Gly Asp Leu Ile Pro Glu Asp Val Leu Asp Ser Leu Phe Pro Leu Ser<br>145                        150                    155                    160 | | 480 |
| acc gat aca ccg cta cct tct tca ctg gaa act ata ggt ata ttg acg<br>Thr Asp Thr Pro Leu Pro Ser Ser Leu Glu Thr Ile Gly Ile Leu Thr<br>                  165                    170                    175 | | 528 |
| gat cca gta cta aat agc acc gac tat ttg atg tct atg tct tta cct<br>Asp Pro Val Leu Asn Ser Thr Asp Tyr Leu Met Ser Met Ser Leu Pro<br>                  180                    185                    190 | | 576 |
| att ttt gcc aat cct tct att atc ttg act gat tca agg gtt tac gga<br>Ile Phe Ala Asn Pro Ser Ile Ile Leu Thr Asp Ser Arg Val Tyr Gly<br>                  195                    200                    205 | | 624 |
| tac att act ata ata atg tcg gca gag ggt ctg aaa agt gtg ttc aac<br>Tyr Ile Thr Ile Ile Met Ser Ala Glu Gly Leu Lys Ser Val Phe Asn<br>210                        215                    220 | | 672 |
| gat aca act gct tta gaa cat tcc aca att gcc att att tct gca gta<br>Asp Thr Thr Ala Leu Glu His Ser Thr Ile Ala Ile Ile Ser Ala Val<br>225                        230                    235                    240 | | 720 |
| tat aat agt caa ggc aaa gct tca ggg tat cat ttt gtc ttt cca ccg<br>Tyr Asn Ser Gln Gly Lys Ala Ser Gly Tyr His Phe Val Phe Pro Pro<br>                  245                    250                    255 | | 768 |
| tat gga tca cga tca gac ctc ccg caa aaa gtt ttt tct ata aaa aat<br>Tyr Gly Ser Arg Ser Asp Leu Pro Gln Lys Val Phe Ser Ile Lys Asn<br>                  260                    265                    270 | | 816 |
| gat aca ttc att agt agc gca ttt aga aac ggg aag gga ggg tct ttg<br>Asp Thr Phe Ile Ser Ser Ala Phe Arg Asn Gly Lys Gly Gly Ser Leu<br>275                        280                    285 | | 864 |
| aaa caa acc aat atc ctt tct aca cgg aat act gct tta ggc tat tca<br>Lys Gln Thr Asn Ile Leu Ser Thr Arg Asn Thr Ala Leu Gly Tyr Ser<br>290                        295                    300 | | 912 |
| cca tgt tcg ttt aac cta gtt aat tgg gtc gcg ata gtt tca cag cct<br>Pro Cys Ser Phe Asn Leu Val Asn Trp Val Ala Ile Val Ser Gln Pro<br>305                        310                    315                    320 | | 960 |
| gag tcg gtt ttc ctt tct cca gca acg aaa cta gca aaa atc atc acc<br>Glu Ser Val Phe Leu Ser Pro Ala Thr Lys Leu Ala Lys Ile Ile Thr<br>                  325                    330                    335 | | 1008 |
| ggc act gtc atc gct att ggt gtc ttt gtc att ttg tta acc ctt cct<br>Gly Thr Val Ile Ala Ile Gly Val Phe Val Ile Leu Leu Thr Leu Pro<br>                  340                    345                    350 | | 1056 |
| cta gca cac tgg gca gtg caa cca att gta cgt cta caa aag gca act<br>Leu Ala His Trp Ala Val Gln Pro Ile Val Arg Leu Gln Lys Ala Thr<br>                  355                    360                    365 | | 1104 |

-continued

| | | | | | | | | | | | | | | | | |
|---|---|---|---|---|---|---|---|---|---|---|---|---|---|---|---|---|
| gaa | tta | att | aca | gag | ggg | aga | ggc | ctt | cga | ccg | agc | acc | cca | aga | acg | 1152 |
| Glu | Leu | Ile | Thr | Glu | Gly | Arg | Gly | Leu | Arg | Pro | Ser | Thr | Pro | Arg | Thr | |
| | | 370 | | | | 375 | | | | 380 | | | | | | |
| ata | agc | aga | gcc | agt | tca | ttc | aaa | aga | gga | ttt | agt | tct | gga | ttt | gct | 1200 |
| Ile | Ser | Arg | Ala | Ser | Ser | Phe | Lys | Arg | Gly | Phe | Ser | Ser | Gly | Phe | Ala | |
| 385 | | | | | 390 | | | | | 395 | | | | | 400 | |
| gtt | cct | tct | tcg | tta | tta | caa | ttt | aat | act | gct | gaa | gct | ggc | agc | acc | 1248 |
| Val | Pro | Ser | Ser | Leu | Leu | Gln | Phe | Asn | Thr | Ala | Glu | Ala | Gly | Ser | Thr | |
| | | | | 405 | | | | | 410 | | | | | 415 | | |
| aca | agc | gta | agt | ggc | cat | gga | ggc | agt | ggc | cat | ggc | agt | ggt | gca | gct | 1296 |
| Thr | Ser | Val | Ser | Gly | His | Gly | Gly | Ser | Gly | His | Gly | Ser | Gly | Ala | Ala | |
| | | | 420 | | | | | 425 | | | | | 430 | | | |
| ttt | tca | gca | aat | agt | agc | atg | aaa | agc | gct | ata | aac | ctt | gga | aat | gag | 1344 |
| Phe | Ser | Ala | Asn | Ser | Ser | Met | Lys | Ser | Ala | Ile | Asn | Leu | Gly | Asn | Glu | |
| | | 435 | | | | | 440 | | | | | 445 | | | | |
| aaa | atg | tca | cct | cca | gag | gag | gag | aac | aaa | ata | ccg | aat | aac | cac | acc | 1392 |
| Lys | Met | Ser | Pro | Pro | Glu | Glu | Glu | Asn | Lys | Ile | Pro | Asn | Asn | His | Thr | |
| 450 | | | | | 455 | | | | | 460 | | | | | | |
| gat | gct | aaa | ata | tca | atg | gat | ggc | tcg | cta | aat | cac | gat | ttg | ctt | gga | 1440 |
| Asp | Ala | Lys | Ile | Ser | Met | Asp | Gly | Ser | Leu | Asn | His | Asp | Leu | Leu | Gly | |
| 465 | | | | | 470 | | | | | 475 | | | | | 480 | |
| cca | cat | tcc | ttg | aga | cat | aat | gac | act | gac | aga | agt | tcc | aat | aga | tct | 1488 |
| Pro | His | Ser | Leu | Arg | His | Asn | Asp | Thr | Asp | Arg | Ser | Ser | Asn | Arg | Ser | |
| | | | | 485 | | | | | 490 | | | | | 495 | | |
| cac | att | ctc | aca | act | tct | gca | aat | tta | act | gaa | gct | agg | cta | cca | gat | 1536 |
| His | Ile | Leu | Thr | Thr | Ser | Ala | Asn | Leu | Thr | Glu | Ala | Arg | Leu | Pro | Asp | |
| | | | 500 | | | | | 505 | | | | | 510 | | | |
| tat | aga | aga | cta | ttt | tct | gat | gaa | ctt | tcc | gat | tta | aca | gaa | acc | ttc | 1584 |
| Tyr | Arg | Arg | Leu | Phe | Ser | Asp | Glu | Leu | Ser | Asp | Leu | Thr | Glu | Thr | Phe | |
| | | 515 | | | | | 520 | | | | | 525 | | | | |
| aat | act | atg | aca | gac | gca | tta | gac | caa | cat | tat | gct | ctt | cta | gaa | gaa | 1632 |
| Asn | Thr | Met | Thr | Asp | Ala | Leu | Asp | Gln | His | Tyr | Ala | Leu | Leu | Glu | Glu | |
| | | 530 | | | | | 535 | | | | | 540 | | | | |
| aga | gtt | agg | gcg | agg | aca | aaa | caa | ctc | gaa | gct | gcc | aag | att | gag | gca | 1680 |
| Arg | Val | Arg | Ala | Arg | Thr | Lys | Gln | Leu | Glu | Ala | Ala | Lys | Ile | Glu | Ala | |
| 545 | | | | | 550 | | | | | 555 | | | | | 560 | |
| gag | gcc | gca | aat | gaa | gca | aaa | acc | gtc | ttt | att | gcc | aat | att | tcg | cac | 1728 |
| Glu | Ala | Ala | Asn | Glu | Ala | Lys | Thr | Val | Phe | Ile | Ala | Asn | Ile | Ser | His | |
| | | | | 565 | | | | | 570 | | | | | 575 | | |
| gaa | ttg | aga | acg | cct | tta | aat | ggt | att | ctg | ggt | atg | acg | gct | att | tca | 1776 |
| Glu | Leu | Arg | Thr | Pro | Leu | Asn | Gly | Ile | Leu | Gly | Met | Thr | Ala | Ile | Ser | |
| | | | 580 | | | | | 585 | | | | | 590 | | | |
| atg | gaa | gaa | acc | gat | gtt | aac | aaa | ata | aga | aat | agt | tta | aaa | ctc | att | 1824 |
| Met | Glu | Glu | Thr | Asp | Val | Asn | Lys | Ile | Arg | Asn | Ser | Leu | Lys | Leu | Ile | |
| | | 595 | | | | | 600 | | | | | 605 | | | | |
| ttt | aga | tca | ggt | gag | ctt | ttg | ctt | cat | att | cta | acg | gaa | ttg | tta | act | 1872 |
| Phe | Arg | Ser | Gly | Glu | Leu | Leu | Leu | His | Ile | Leu | Thr | Glu | Leu | Leu | Thr | |
| 610 | | | | | 615 | | | | | 620 | | | | | | |
| ttt | tcc | aaa | aac | gtt | ctt | caa | aga | acg | aaa | ctg | gag | aaa | aga | gat | ttt | 1920 |
| Phe | Ser | Lys | Asn | Val | Leu | Gln | Arg | Thr | Lys | Leu | Glu | Lys | Arg | Asp | Phe | |
| 625 | | | | | 630 | | | | | 635 | | | | | 640 | |
| tgc | att | acc | gat | gtt | gcc | tta | caa | ata | aaa | tcg | ata | ttt | ggt | aaa | gtt | 1968 |
| Cys | Ile | Thr | Asp | Val | Ala | Leu | Gln | Ile | Lys | Ser | Ile | Phe | Gly | Lys | Val | |
| | | | | 645 | | | | | 650 | | | | | 655 | | |
| gca | aag | gat | cag | cgt | gtt | cgt | ctt | tca | ata | tca | ttg | ttt | cct | aat | ttg | 2016 |
| Ala | Lys | Asp | Gln | Arg | Val | Arg | Leu | Ser | Ile | Ser | Leu | Phe | Pro | Asn | Leu | |
| | | | 660 | | | | | 665 | | | | | 670 | | | |
| ata | agg | aca | atg | gtt | ctt | tgg | ggt | gat | tcc | aac | aga | att | att | caa | att | 2064 |
| Ile | Arg | Thr | Met | Val | Leu | Trp | Gly | Asp | Ser | Asn | Arg | Ile | Ile | Gln | Ile | |

-continued

```
              675                 680                 685
gtg atg aat cta gtg tcc aat gca cta aag ttc acc cct gta gat ggt    2112
Val Met Asn Leu Val Ser Asn Ala Leu Lys Phe Thr Pro Val Asp Gly
    690                 695                 700 acc gtt gat gta aga atg aaa ctg ttg ggt gaa tac gac aaa gaa tta    2160
Thr Val Asp Val Arg Met Lys Leu Leu Gly Glu Tyr Asp Lys Glu Leu
705                 710                 715                 720 agc gag aag aag caa tac aaa gaa gtg tat atc aaa aaa ggg aca gaa    2208
Ser Glu Lys Lys Gln Tyr Lys Glu Val Tyr Ile Lys Lys Gly Thr Glu
                725                 730                 735 gta acc gaa aat tta gaa act aca gat aaa tac gat ctt cca act tta    2256
Val Thr Glu Asn Leu Glu Thr Thr Asp Lys Tyr Asp Leu Pro Thr Leu
        740                 745                 750 tcg aac cat agg aaa agt gtc gat tta gaa tcc agc gct act tcc cta    2304
Ser Asn His Arg Lys Ser Val Asp Leu Glu Ser Ser Ala Thr Ser Leu
            755                 760                 765 gga agt aat aga gac act tcg aca att cag gaa gag ata aca aaa aga    2352
Gly Ser Asn Arg Asp Thr Ser Thr Ile Gln Glu Glu Ile Thr Lys Arg
        770                 775                 780 aat act gtt gcg aat gaa agt atc tat aag aaa gtg aat gac agg gaa    2400
Asn Thr Val Ala Asn Glu Ser Ile Tyr Lys Lys Val Asn Asp Arg Glu
785                 790                 795                 800 aaa gct tcg aat gat gat gta tct tct ata gta tca aca act acc agc    2448
Lys Ala Ser Asn Asp Asp Val Ser Ser Ile Val Ser Thr Thr Thr Ser
                805                 810                 815 tcg tat gat aac gct atc ttc aat agt cag ttc aat aaa gca cct ggc    2496
Ser Tyr Asp Asn Ala Ile Phe Asn Ser Gln Phe Asn Lys Ala Pro Gly
                820                 825                 830 tca gat gat gaa gaa ggt ggt aac cta gga aga cct atc gaa aac ccc    2544
Ser Asp Asp Glu Glu Gly Gly Asn Leu Gly Arg Pro Ile Glu Asn Pro
            835                 840                 845 aaa acg tgg gtt att tct att gaa gtg gaa gac act ggg cct ggt att    2592
Lys Thr Trp Val Ile Ser Ile Glu Val Glu Asp Thr Gly Pro Gly Ile
850                 855                 860 gac cct tcc tta caa gaa tct gta ttt cat cca ttt gtt caa ggt gat    2640
Asp Pro Ser Leu Gln Glu Ser Val Phe His Pro Phe Val Gln Gly Asp
865                 870                 875                 880 caa aca ttg tcc agg caa tat ggt ggt act ggc tta ggt cta tca atc    2688
Gln Thr Leu Ser Arg Gln Tyr Gly Gly Thr Gly Leu Gly Leu Ser Ile
                885                 890                 895 tgt aga cag tta gca aat atg atg cat gga acg atg aaa tta gag tcg    2736
Cys Arg Gln Leu Ala Asn Met Met His Gly Thr Met Lys Leu Glu Ser
            900                 905                 910 aaa gta ggt gtt ggt agt aaa ttc act ttt acc ttg cca tta aat caa    2784
Lys Val Gly Val Gly Ser Lys Phe Thr Phe Thr Leu Pro Leu Asn Gln
        915                 920                 925 act aaa gag atc agt ttt gca gat atg gag ttt cct ttt gag gac gaa    2832
Thr Lys Glu Ile Ser Phe Ala Asp Met Glu Phe Pro Phe Glu Asp Glu
    930                 935                 940 ttt aat cct gag agt aga aag aac aga aga gtc aag ttt agt gtt gct    2880
Phe Asn Pro Glu Ser Arg Lys Asn Arg Arg Val Lys Phe Ser Val Ala
945                 950                 955                 960 aaa agc atc aag agc cga caa tcc aca tca tct gtt gca aca cca gct    2928
Lys Ser Ile Lys Ser Arg Gln Ser Thr Ser Ser Val Ala Thr Pro Ala
                965                 970                 975 aca aat aga agt agc cta acc aac gac gtg cta ccg gag gta aga agt    2976
Thr Asn Arg Ser Ser Leu Thr Asn Asp Val Leu Pro Glu Val Arg Ser
            980                 985                 990 aaa ggt aag cat gag acg aaa gat  gtt gga aat cct aac  atg gga aga    3024
```

```
Lys Gly Lys His Glu Thr Lys Asp Val Gly Asn Pro Asn Met Gly Arg
            995                 1000                1005 gaa gaa aaa aac gac aat gga ggg ctt gaa caa ctg cag gaa aaa           3069
Glu Glu Lys Asn Asp Asn Gly Gly Leu Glu Gln Leu Gln Glu Lys
    1010                1015                1020 aat att aaa cct tct ata tgt ctt aca ggt gct gaa gtt aac gaa           3114
Asn Ile Lys Pro Ser Ile Cys Leu Thr Gly Ala Glu Val Asn Glu
1025                1030                1035 caa aat tcc ttg tct tct aag cat cgt tct cga cat gaa ggt cta           3159
Gln Asn Ser Leu Ser Ser Lys His Arg Ser Arg His Glu Gly Leu
    1040                1045                1050 ggt tct gtc aat ctt gat aga cca ttt ttg caa agt act ggt aca           3204
Gly Ser Val Asn Leu Asp Arg Pro Phe Leu Gln Ser Thr Gly Thr
    1055                1060                1065 gcc aca tca agt aga aac atc ccc aca gtc aaa gac gat aaa               3249
Ala Thr Ser Ser Arg Asn Ile Pro Thr Val Lys Asp Asp Lys
    1070                1075                1080 aat gaa aca agt gtc aaa att ttg gtt gta gaa gat aat cat gta           3294
Asn Glu Thr Ser Val Lys Ile Leu Val Val Glu Asp Asn His Val
    1085                1090                1095 aat cag gaa gtt atc aaa aga atg ttg aac ttg gag ggc att gaa           3339
Asn Gln Glu Val Ile Lys Arg Met Leu Asn Leu Glu Gly Ile Glu
    1100                1105                1110 aat att gaa ctg gct tgc gat ggc caa gaa gca ttc gac aaa gtt           3384
Asn Ile Glu Leu Ala Cys Asp Gly Gln Glu Ala Phe Asp Lys Val
    1115                1120                1125 aaa gaa ttg aca tct aag ggc gaa aat tat aat atg att ttc atg           3429
Lys Glu Leu Thr Ser Lys Gly Glu Asn Tyr Asn Met Ile Phe Met
    1130                1135                1140 gat gtc cag atg cct aaa gtg gat ggt tta ctt tct acc aag atg           3474
Asp Val Gln Met Pro Lys Val Asp Gly Leu Leu Ser Thr Lys Met
    1145                1150                1155 ata agg cgc gat tta ggt tat acc tca cct att gtc gct cta acc           3519
Ile Arg Arg Asp Leu Gly Tyr Thr Ser Pro Ile Val Ala Leu Thr
    1160                1165                1170 gct ttt gct gac gat agc aac att aaa gaa tgt ttg gaa tca gga           3564
Ala Phe Ala Asp Asp Ser Asn Ile Lys Glu Cys Leu Glu Ser Gly
    1175                1180                1185 atg aac gga ttt tta tcg aaa cca atc aaa aga cca aaa ttg aaa           3609
Met Asn Gly Phe Leu Ser Lys Pro Ile Lys Arg Pro Lys Leu Lys
    1190                1195                1200 act att ctt act gag ttt tgt gca gca tat cag gga aag aaa aat           3654
Thr Ile Leu Thr Glu Phe Cys Ala Ala Tyr Gln Gly Lys Lys Asn
    1205                1210                1215 aac aaa                                                                3660
Asn Lys
    1220

<210> SEQ ID NO 10
<211> LENGTH: 1220
<212> TYPE: PRT
<213> ORGANISM: Saccharomyces cerevisiae

<400> SEQUENCE: 10

Met Arg Phe Gly Leu Pro Ser Lys Leu Glu Leu Thr Pro Pro Phe Arg
1               5                   10                  15

Ile Gly Ile Arg Thr Gln Leu Thr Ala Leu Val Ser Ile Val Ala Leu
            20                  25                  30

Gly Ser Leu Ile Ile Leu Ala Val Thr Thr Gly Val Tyr Phe Thr Ser
        35                  40                  45
```

-continued

```
Asn Tyr Lys Asn Leu Arg Ser Asp Arg Leu Tyr Ile Ala Ala Gln Leu
         50                  55                  60

Lys Ser Ser Gln Ile Asp Gln Thr Leu Asn Tyr Leu Tyr Tyr Gln Ala
 65                  70                  75                  80

Tyr Tyr Leu Ala Ser Arg Asp Ala Leu Gln Ser Ser Leu Thr Ser Tyr
                 85                  90                  95

Val Ala Gly Asn Lys Ser Ala Asp Asn Trp Val Asp Ser Leu Ser Val
                100                 105                 110

Ile Gln Lys Phe Leu Ser Ser Ser Asn Leu Phe Tyr Val Ala Lys Val
            115                 120                 125

Tyr Asp Ser Ser Phe Asn Ala Val Leu Asn Ala Thr Asn Asn Gly Thr
130                 135                 140

Gly Asp Leu Ile Pro Glu Asp Val Leu Asp Ser Leu Phe Pro Leu Ser
145                 150                 155                 160

Thr Asp Thr Pro Leu Pro Ser Ser Leu Glu Thr Ile Gly Ile Leu Thr
                165                 170                 175

Asp Pro Val Leu Asn Ser Thr Asp Tyr Leu Met Ser Met Ser Leu Pro
                180                 185                 190

Ile Phe Ala Asn Pro Ser Ile Ile Leu Thr Asp Ser Arg Val Tyr Gly
            195                 200                 205

Tyr Ile Thr Ile Ile Met Ser Ala Glu Gly Leu Lys Ser Val Phe Asn
210                 215                 220

Asp Thr Thr Ala Leu Glu His Ser Thr Ile Ala Ile Ser Ala Val
225                 230                 235                 240

Tyr Asn Ser Gln Gly Lys Ala Ser Gly Tyr His Phe Val Phe Pro Pro
                245                 250                 255

Tyr Gly Ser Arg Ser Asp Leu Pro Gln Lys Val Phe Ser Ile Lys Asn
                260                 265                 270

Asp Thr Phe Ile Ser Ser Ala Phe Arg Asn Gly Lys Gly Gly Ser Leu
            275                 280                 285

Lys Gln Thr Asn Ile Leu Ser Thr Arg Asn Thr Ala Leu Gly Tyr Ser
            290                 295                 300

Pro Cys Ser Phe Asn Leu Val Asn Trp Val Ala Ile Val Ser Gln Pro
305                 310                 315                 320

Glu Ser Val Phe Leu Ser Pro Ala Thr Lys Leu Ala Lys Ile Ile Thr
                325                 330                 335

Gly Thr Val Ile Ala Ile Gly Val Phe Val Ile Leu Thr Leu Pro
                340                 345                 350

Leu Ala His Trp Ala Val Gln Pro Ile Val Arg Leu Gln Lys Ala Thr
            355                 360                 365

Glu Leu Ile Thr Glu Gly Arg Gly Leu Arg Pro Ser Thr Pro Arg Thr
370                 375                 380

Ile Ser Arg Ala Ser Ser Phe Lys Arg Gly Phe Ser Ser Gly Phe Ala
385                 390                 395                 400

Val Pro Ser Ser Leu Leu Gln Phe Asn Thr Ala Glu Ala Gly Ser Thr
                405                 410                 415

Thr Ser Val Ser Gly His Gly Gly Ser Gly His Gly Ser Gly Ala Ala
                420                 425                 430

Phe Ser Ala Asn Ser Ser Met Lys Ser Ala Ile Asn Leu Gly Asn Glu
            435                 440                 445

Lys Met Ser Pro Pro Glu Glu Asn Lys Ile Pro Asn Asn His Thr
450                 455                 460
```

```
Asp Ala Lys Ile Ser Met Asp Gly Ser Leu Asn His Asp Leu Leu Gly
465                 470                 475                 480

Pro His Ser Leu Arg His Asn Asp Thr Asp Arg Ser Ser Asn Arg Ser
                485                 490                 495

His Ile Leu Thr Thr Ser Ala Asn Leu Thr Glu Ala Arg Leu Pro Asp
            500                 505                 510

Tyr Arg Arg Leu Phe Ser Asp Glu Leu Ser Asp Leu Thr Glu Thr Phe
        515                 520                 525

Asn Thr Met Thr Asp Ala Leu Asp Gln His Tyr Ala Leu Leu Glu Glu
    530                 535                 540

Arg Val Arg Ala Arg Thr Lys Gln Leu Glu Ala Ala Lys Ile Glu Ala
545                 550                 555                 560

Glu Ala Ala Asn Glu Ala Lys Thr Val Phe Ile Ala Asn Ile Ser His
                565                 570                 575

Glu Leu Arg Thr Pro Leu Asn Gly Ile Leu Gly Met Thr Ala Ile Ser
            580                 585                 590

Met Glu Glu Thr Asp Val Asn Lys Ile Arg Asn Ser Leu Lys Leu Ile
    595                 600                 605

Phe Arg Ser Gly Glu Leu Leu Leu His Ile Leu Thr Glu Leu Leu Thr
610                 615                 620

Phe Ser Lys Asn Val Leu Gln Arg Thr Lys Leu Glu Lys Arg Asp Phe
625                 630                 635                 640

Cys Ile Thr Asp Val Ala Leu Gln Ile Lys Ser Ile Phe Gly Lys Val
            645                 650                 655

Ala Lys Asp Gln Arg Val Arg Leu Ser Ile Ser Leu Phe Pro Asn Leu
        660                 665                 670

Ile Arg Thr Met Val Leu Trp Gly Asp Ser Asn Arg Ile Ile Gln Ile
    675                 680                 685

Val Met Asn Leu Val Ser Asn Ala Leu Lys Phe Thr Pro Val Asp Gly
    690                 695                 700

Thr Val Asp Val Arg Met Lys Leu Leu Gly Glu Tyr Asp Lys Glu Leu
705                 710                 715                 720

Ser Glu Lys Lys Gln Tyr Lys Glu Val Tyr Ile Lys Lys Gly Thr Glu
                725                 730                 735

Val Thr Glu Asn Leu Glu Thr Thr Asp Lys Tyr Asp Leu Pro Thr Leu
            740                 745                 750

Ser Asn His Arg Lys Ser Val Asp Leu Glu Ser Ser Ala Thr Ser Leu
        755                 760                 765

Gly Ser Asn Arg Asp Thr Ser Thr Ile Gln Glu Glu Ile Thr Lys Arg
    770                 775                 780

Asn Thr Val Ala Asn Glu Ser Ile Tyr Lys Lys Val Asn Asp Arg Glu
785                 790                 795                 800

Lys Ala Ser Asn Asp Asp Val Ser Ser Ile Val Ser Thr Thr Thr Ser
                805                 810                 815

Ser Tyr Asp Asn Ala Ile Phe Asn Ser Gln Phe Asn Lys Ala Pro Gly
            820                 825                 830

Ser Asp Asp Glu Glu Gly Gly Asn Leu Gly Arg Pro Ile Glu Asn Pro
        835                 840                 845

Lys Thr Trp Val Ile Ser Ile Glu Val Glu Asp Thr Gly Pro Gly Ile
    850                 855                 860

Asp Pro Ser Leu Gln Glu Ser Val Phe His Pro Phe Val Gln Gly Asp
865                 870                 875                 880

Gln Thr Leu Ser Arg Gln Tyr Gly Gly Thr Gly Leu Gly Leu Ser Ile
```

```
                      885                 890                 895
            Cys Arg Gln Leu Ala Asn Met Met His Gly Thr Met Lys Leu Glu Ser
                900                 905                 910
            Lys Val Gly Val Gly Ser Lys Phe Thr Phe Thr Leu Pro Leu Asn Gln
                915                 920                 925
            Thr Lys Glu Ile Ser Phe Ala Asp Met Glu Phe Pro Phe Glu Asp Glu
                930                 935                 940
            Phe Asn Pro Glu Ser Arg Lys Asn Arg Arg Val Lys Phe Ser Val Ala
            945                 950                 955                 960
            Lys Ser Ile Lys Ser Arg Gln Ser Thr Ser Ser Val Ala Thr Pro Ala
                            965                 970                 975
            Thr Asn Arg Ser Ser Leu Thr Asn Asp Val Leu Pro Glu Val Arg Ser
                        980                 985                 990
            Lys Gly Lys His Glu Thr Lys Asp Val Gly Asn Pro Asn Met Gly Arg
                    995                1000                1005
            Glu Glu Lys Asn Asp Asn Gly Gly Leu Glu Gln Leu Gln Glu Lys
                1010                1015                1020
            Asn Ile Lys Pro Ser Ile Cys Leu Thr Gly Ala Glu Val Asn Glu
                1025                1030                1035
            Gln Asn Ser Leu Ser Ser Lys His Arg Ser Arg His Glu Gly Leu
                1040                1045                1050
            Gly Ser Val Asn Leu Asp Arg Pro Phe Leu Gln Ser Thr Gly Thr
                1055                1060                1065
            Ala Thr Ser Ser Arg Asn Ile Pro Thr Val Lys Asp Asp Asp Lys
                1070                1075                1080
            Asn Glu Thr Ser Val Lys Ile Leu Val Val Glu Asp Asn His Val
                1085                1090                1095
            Asn Gln Glu Val Ile Lys Arg Met Leu Asn Leu Glu Gly Ile Glu
                1100                1105                1110
            Asn Ile Glu Leu Ala Cys Asp Gly Gln Glu Ala Phe Asp Lys Val
                1115                1120                1125
            Lys Glu Leu Thr Ser Lys Gly Glu Asn Tyr Asn Met Ile Phe Met
                1130                1135                1140
            Asp Val Gln Met Pro Lys Val Asp Gly Leu Leu Ser Thr Lys Met
                1145                1150                1155
            Ile Arg Arg Asp Leu Gly Tyr Thr Ser Pro Ile Val Ala Leu Thr
                1160                1165                1170
            Ala Phe Ala Asp Asp Ser Asn Ile Lys Glu Cys Leu Glu Ser Gly
                1175                1180                1185
            Met Asn Gly Phe Leu Ser Lys Pro Ile Lys Arg Pro Lys Leu Lys
                1190                1195                1200
            Thr Ile Leu Thr Glu Phe Cys Ala Ala Tyr Gln Gly Lys Lys Asn
                1205                1210                1215
            Asn Lys
                1220

<210> SEQ ID NO 11
<211> LENGTH: 1866
<212> TYPE: DNA
<213> ORGANISM: Saccharomyces cerevisiae
<220> FEATURE:
<221> NAME/KEY: CDS
<222> LOCATION: (1)..(1866)

<400> SEQUENCE: 11
```

-continued

| | |
|---|---|
| atg agc ttt tcc acc ata aat agc aac gtc aat aaa acc acc ggc gat<br>Met Ser Phe Ser Thr Ile Asn Ser Asn Val Asn Lys Thr Thr Gly Asp<br>1               5                   10                  15 | 48 |
| agc aat aat aac acc acc gag aac agt tcg act gca gac ctt tta gga<br>Ser Asn Asn Asn Thr Thr Glu Asn Ser Ser Thr Ala Asp Leu Leu Gly<br>            20                  25                  30 | 96 |
| atg gac ttg ttg cag agc ggg cct cga ctg atg aac acg atg cag cca<br>Met Asp Leu Leu Gln Ser Gly Pro Arg Leu Met Asn Thr Met Gln Pro<br>        35                  40                  45 | 144 |
| aac aac tct tct gac atg ctg cac att aac aac aag act aat aac gtt<br>Asn Asn Ser Ser Asp Met Leu His Ile Asn Asn Lys Thr Asn Asn Val<br>50                  55                  60 | 192 |
| caa caa cca gct gga aac aca aat atc agc agt gct aat gcg gga gca<br>Gln Gln Pro Ala Gly Asn Thr Asn Ile Ser Ser Ala Asn Ala Gly Ala<br>65                  70                  75                  80 | 240 |
| aag gct cca gca aat gag ttc gta aga aaa ctg ttc agg ata ctg gaa<br>Lys Ala Pro Ala Asn Glu Phe Val Arg Lys Leu Phe Arg Ile Leu Glu<br>                85                  90                  95 | 288 |
| aac aat gaa tat cct gac att gta act tgg act gag aac ggc aaa agt<br>Asn Asn Glu Tyr Pro Asp Ile Val Thr Trp Thr Glu Asn Gly Lys Ser<br>            100                 105                 110 | 336 |
| ttc gtc gtt ttg gac aca gga aag ttc act acg cat ata ttg cct aat<br>Phe Val Val Leu Asp Thr Gly Lys Phe Thr Thr His Ile Leu Pro Asn<br>        115                 120                 125 | 384 |
| cac ttc aaa cat tca aat ttt gca tct ttt gta agg caa cta aac aag<br>His Phe Lys His Ser Asn Phe Ala Ser Phe Val Arg Gln Leu Asn Lys<br>130                 135                 140 | 432 |
| tat gac ttt cac aag gtt aag aga agt ccc gag gaa aga cag aga tgt<br>Tyr Asp Phe His Lys Val Lys Arg Ser Pro Glu Glu Arg Gln Arg Cys<br>145                 150                 155                 160 | 480 |
| aaa tat ggc gaa caa agt tgg gag ttt cag cat cca gaa ttt aga gtc<br>Lys Tyr Gly Glu Gln Ser Trp Glu Phe Gln His Pro Glu Phe Arg Val<br>                165                 170                 175 | 528 |
| cat tac gga aaa ggt ctc gat aac atc aaa agg aaa att ccg gcg caa<br>His Tyr Gly Lys Gly Leu Asp Asn Ile Lys Arg Lys Ile Pro Ala Gln<br>            180                 185                 190 | 576 |
| agg aaa gtg ctt ttg gat gaa tct caa aag gct ctt ttg cat ttc aat<br>Arg Lys Val Leu Leu Asp Glu Ser Gln Lys Ala Leu Leu His Phe Asn<br>        195                 200                 205 | 624 |
| agt gaa ggc act aac ccc aac aat cct tct ggg tct ctt ttg aat gaa<br>Ser Glu Gly Thr Asn Pro Asn Asn Pro Ser Gly Ser Leu Leu Asn Glu<br>210                 215                 220 | 672 |
| tcc acc aca gag ctg ttg tta agc aat acc gta agt aaa gat gca ttt<br>Ser Thr Thr Glu Leu Leu Leu Ser Asn Thr Val Ser Lys Asp Ala Phe<br>225                 230                 235                 240 | 720 |
| gga aat cta aga agg cga gta gac aaa cta caa aag gag ttg gat atg<br>Gly Asn Leu Arg Arg Arg Val Asp Lys Leu Gln Lys Glu Leu Asp Met<br>                245                 250                 255 | 768 |
| tcc aaa atg gag agt tat gct act aaa gta gaa cta caa aag ttg aac<br>Ser Lys Met Glu Ser Tyr Ala Thr Lys Val Glu Leu Gln Lys Leu Asn<br>            260                 265                 270 | 816 |
| tcg aaa tac aat acg gtt atc gaa agt ttg ata aca ttc aag acc ata<br>Ser Lys Tyr Asn Thr Val Ile Glu Ser Leu Ile Thr Phe Lys Thr Ile<br>        275                 280                 285 | 864 |
| aat gaa aat tta ctc aac aac ttc aac act ctg tgt tcc act ttg gca<br>Asn Glu Asn Leu Leu Asn Asn Phe Asn Thr Leu Cys Ser Thr Leu Ala<br>290                 295                 300 | 912 |
| aat aat ggt att gaa gtg cca ata ttt ggc gac aat gga aac cgt aac<br>Asn Asn Gly Ile Glu Val Pro Ile Phe Gly Asp Asn Gly Asn Arg Asn<br>305                 310                 315                 320 | 960 |

-continued

```
cca act ggt aat acc aac cca gca aca aca aca gct atc caa agc aac       1008
Pro Thr Gly Asn Thr Asn Pro Ala Thr Thr Thr Ala Ile Gln Ser Asn
            325                 330                 335 aac aac acc aac aat gct tct ccg gca aca tct aca gtt tcc tta caa       1056
Asn Asn Thr Asn Asn Ala Ser Pro Ala Thr Ser Thr Val Ser Leu Gln
        340                 345                 350 cta cct aat tta ccc gat cag aat agc cta aca cca aat gct caa aat       1104
Leu Pro Asn Leu Pro Asp Gln Asn Ser Leu Thr Pro Asn Ala Gln Asn
    355                 360                 365 aac aca gtc acg cta cga aaa ggt ttc cat gta ctg ttg gtg gaa gat       1152
Asn Thr Val Thr Leu Arg Lys Gly Phe His Val Leu Leu Val Glu Asp
370                 375                 380 gac gca gtg tct ata cag ttg tgt tca aaa ttt tta cgg aaa tat ggc       1200
Asp Ala Val Ser Ile Gln Leu Cys Ser Lys Phe Leu Arg Lys Tyr Gly
385                 390                 395                 400 tgt act gtc caa gtt gtc agc gac ggt ctt tca gct atc tca aca cta       1248
Cys Thr Val Gln Val Val Ser Asp Gly Leu Ser Ala Ile Ser Thr Leu
            405                 410                 415 gag aag tat agg tat gat ttg gtt tta atg gac att gtt atg cca aac       1296
Glu Lys Tyr Arg Tyr Asp Leu Val Leu Met Asp Ile Val Met Pro Asn
        420                 425                 430 cta gat ggt gcc aca gcg aca tcc att gtc aga agt ttt gat aat gag       1344
Leu Asp Gly Ala Thr Ala Thr Ser Ile Val Arg Ser Phe Asp Asn Glu
    435                 440                 445 act ccc atc att gcc atg aca ggt aac att atg aat caa gac ttg atc       1392
Thr Pro Ile Ile Ala Met Thr Gly Asn Ile Met Asn Gln Asp Leu Ile
450                 455                 460 aca tac tta caa cat gga atg aat gat atc ttg gcc aaa cca ttc acg       1440
Thr Tyr Leu Gln His Gly Met Asn Asp Ile Leu Ala Lys Pro Phe Thr
465                 470                 475                 480 agg gat gat tta cac tca att tta ata cgt tat cta aag gac cgt att       1488
Arg Asp Asp Leu His Ser Ile Leu Ile Arg Tyr Leu Lys Asp Arg Ile
            485                 490                 495 cct tta tgc gaa cag caa tta cca cct cgc aac tct tcg cca caa act       1536
Pro Leu Cys Glu Gln Gln Leu Pro Pro Arg Asn Ser Ser Pro Gln Thr
        500                 505                 510 cat tcc aac acc aat act gct aat tcg aat cct aat acg att aat gaa       1584
His Ser Asn Thr Asn Thr Ala Asn Ser Asn Pro Asn Thr Ile Asn Glu
    515                 520                 525 cag tcg tta gcc atg tta cca caa gat aat ccg tca act act acc cct       1632
Gln Ser Leu Ala Met Leu Pro Gln Asp Asn Pro Ser Thr Thr Thr Pro
530                 535                 540 gtt acc cca ggt gcc tct ata tct tct gca cag cat gtt caa caa ggt       1680
Val Thr Pro Gly Ala Ser Ile Ser Ser Ala Gln His Val Gln Gln Gly
545                 550                 555                 560 caa caa gaa cag cag cat caa att ttc cat gct cag cag cag cag cag       1728
Gln Gln Glu Gln Gln His Gln Ile Phe His Ala Gln Gln Gln Gln Gln
            565                 570                 575 cat cac aac gcc att gct aat gct agg tca gac gta gcc ata ccg aat       1776
His His Asn Ala Ile Ala Asn Ala Arg Ser Asp Val Ala Ile Pro Asn
        580                 585                 590 ttg gaa cat gaa atc aac act gta cca cat tcc tca atg ggt tcc act       1824
Leu Glu His Glu Ile Asn Thr Val Pro His Ser Ser Met Gly Ser Thr
    595                 600                 605 ccg caa tta cca caa tct aca ctt caa gaa aac cag cta tca                1866
Pro Gln Leu Pro Gln Ser Thr Leu Gln Glu Asn Gln Leu Ser
610                 615                 620
```

<210> SEQ ID NO 12

<211> LENGTH: 622
<212> TYPE: PRT
<213> ORGANISM: Saccharomyces cerevisiae

<400> SEQUENCE: 12

```
Met Ser Phe Ser Thr Ile Asn Ser Asn Val Asn Lys Thr Thr Gly Asp
1               5                   10                  15

Ser Asn Asn Asn Thr Thr Glu Asn Ser Ser Thr Ala Asp Leu Leu Gly
            20                  25                  30

Met Asp Leu Leu Gln Ser Gly Pro Arg Leu Met Asn Thr Met Gln Pro
        35                  40                  45

Asn Asn Ser Ser Asp Met Leu His Ile Asn Asn Lys Thr Asn Asn Val
50                  55                  60

Gln Gln Pro Ala Gly Asn Thr Asn Ile Ser Ser Ala Asn Ala Gly Ala
65                  70                  75                  80

Lys Ala Pro Ala Asn Glu Phe Val Arg Lys Leu Phe Arg Ile Leu Glu
                85                  90                  95

Asn Asn Glu Tyr Pro Asp Ile Val Thr Trp Thr Glu Asn Gly Lys Ser
            100                 105                 110

Phe Val Val Leu Asp Thr Gly Lys Phe Thr Thr His Ile Leu Pro Asn
        115                 120                 125

His Phe Lys His Ser Asn Phe Ala Ser Phe Val Arg Gln Leu Asn Lys
    130                 135                 140

Tyr Asp Phe His Lys Val Lys Arg Ser Pro Glu Arg Gln Arg Cys
145                 150                 155                 160

Lys Tyr Gly Glu Gln Ser Trp Glu Phe Gln His Pro Glu Phe Arg Val
                165                 170                 175

His Tyr Gly Lys Gly Leu Asp Asn Ile Lys Arg Lys Ile Pro Ala Gln
            180                 185                 190

Arg Lys Val Leu Leu Asp Glu Ser Gln Lys Ala Leu Leu His Phe Asn
        195                 200                 205

Ser Glu Gly Thr Asn Pro Asn Pro Ser Gly Ser Leu Leu Asn Glu
    210                 215                 220

Ser Thr Thr Glu Leu Leu Leu Ser Asn Thr Val Ser Lys Asp Ala Phe
225                 230                 235                 240

Gly Asn Leu Arg Arg Arg Val Asp Lys Leu Gln Lys Glu Leu Asp Met
                245                 250                 255

Ser Lys Met Glu Ser Tyr Ala Thr Lys Val Glu Leu Gln Lys Leu Asn
            260                 265                 270

Ser Lys Tyr Asn Thr Val Ile Glu Ser Leu Ile Thr Phe Lys Thr Ile
        275                 280                 285

Asn Glu Asn Leu Leu Asn Asn Phe Asn Thr Leu Cys Ser Thr Leu Ala
    290                 295                 300

Asn Asn Gly Ile Glu Val Pro Ile Phe Gly Asp Asn Gly Asn Arg Asn
305                 310                 315                 320

Pro Thr Gly Asn Thr Asn Pro Ala Thr Thr Ala Ile Gln Ser Asn
                325                 330                 335

Asn Asn Thr Asn Asn Ala Ser Pro Ala Thr Ser Thr Val Ser Leu Gln
            340                 345                 350

Leu Pro Asn Leu Pro Asp Gln Asn Ser Leu Thr Pro Asn Ala Gln Asn
        355                 360                 365

Asn Thr Val Thr Leu Arg Lys Gly Phe His Val Leu Leu Val Glu Asp
    370                 375                 380

Asp Ala Val Ser Ile Gln Leu Cys Ser Lys Phe Leu Arg Lys Tyr Gly
```

```
                385                 390                 395                 400
        Cys Thr Val Gln Val Val Ser Asp Gly Leu Ser Ala Ile Ser Thr Leu
                            405                 410                 415

Glu Lys Tyr Arg Tyr Asp Leu Val Leu Met Asp Ile Val Met Pro Asn
                            420                 425                 430

Leu Asp Gly Ala Thr Ala Thr Ser Ile Val Arg Ser Phe Asp Asn Glu
                            435                 440                 445

Thr Pro Ile Ile Ala Met Thr Gly Asn Ile Met Asn Gln Asp Leu Ile
                    450                 455                 460

Thr Tyr Leu Gln His Gly Met Asn Asp Ile Leu Ala Lys Pro Phe Thr
        465                 470                 475                 480

Arg Asp Asp Leu His Ser Ile Leu Ile Arg Tyr Leu Lys Asp Arg Ile
                            485                 490                 495

Pro Leu Cys Glu Gln Gln Leu Pro Pro Arg Asn Ser Ser Pro Gln Thr
                        500                 505                 510

His Ser Asn Thr Asn Thr Ala Asn Ser Asn Pro Asn Thr Ile Asn Glu
                    515                 520                 525

Gln Ser Leu Ala Met Leu Pro Gln Asp Asn Pro Ser Thr Thr Thr Pro
                530                 535                 540

Val Thr Pro Gly Ala Ser Ile Ser Ser Ala Gln His Val Gln Gln Gly
        545                 550                 555                 560

Gln Gln Glu Gln Gln His Gln Ile Phe His Ala Gln Gln Gln Gln
                            565                 570                 575

His His Asn Ala Ile Ala Asn Ala Arg Ser Asp Val Ala Ile Pro Asn
                        580                 585                 590

Leu Glu His Glu Ile Asn Thr Val Pro His Ser Ser Met Gly Ser Thr
                    595                 600                 605

Pro Gln Leu Pro Gln Ser Thr Leu Gln Glu Asn Gln Leu Ser
                610                 615                 620

<210> SEQ ID NO 13
<211> LENGTH: 1305
<212> TYPE: DNA
<213> ORGANISM: Saccharomyces cerevisiae
<220> FEATURE:
<221> NAME/KEY: CDS
<222> LOCATION: (1)..(1305)

<400> SEQUENCE: 13 atg gac tac aac aag aga tct tcg gtc tca acc gtg cct aat gca gct       48
Met Asp Tyr Asn Lys Arg Ser Ser Val Ser Thr Val Pro Asn Ala Ala
1               5                   10                  15 ccc ata aga gtc gga ttc gtc ggt ctc aac gca gcc aaa gga tgg gca       96
Pro Ile Arg Val Gly Phe Val Gly Leu Asn Ala Ala Lys Gly Trp Ala
            20                  25                  30 atc aag aca cat tac ccc gcc ata ctg caa cta tcg tca caa ttt caa      144
Ile Lys Thr His Tyr Pro Ala Ile Leu Gln Leu Ser Ser Gln Phe Gln
        35                  40                  45 atc act gcc tta tac agt cca aaa att gag act tct att gcc acc att      192
Ile Thr Ala Leu Tyr Ser Pro Lys Ile Glu Thr Ser Ile Ala Thr Ile
    50                  55                  60 cag cgt cta aaa ttg agt aat gcc act gct ttt ccc act tta gag tca      240
Gln Arg Leu Lys Leu Ser Asn Ala Thr Ala Phe Pro Thr Leu Glu Ser
65                  70                  75                  80 ttt gca tca tct tcc act ata gat atg ata gtg ata gct atc caa gtg      288
Phe Ala Ser Ser Ser Thr Ile Asp Met Ile Val Ile Ala Ile Gln Val
                85                  90                  95
```

-continued

| | |
|---|---|
| gcc agc cat tat gaa gtt gtt atg cct ctc ttg gaa ttc tcc aaa aat<br>Ala Ser His Tyr Glu Val Val Met Pro Leu Leu Glu Phe Ser Lys Asn<br>            100                105               110 | 336 |
| aat ccg aac ctc aag tat ctt ttc gta gaa tgg gcc ctt gca tgt tca<br>Asn Pro Asn Leu Lys Tyr Leu Phe Val Glu Trp Ala Leu Ala Cys Ser<br>        115                120               125 | 384 |
| cta gat caa gcc gaa tcc att tat aag gct gct gct gaa cgt ggg gtt<br>Leu Asp Gln Ala Glu Ser Ile Tyr Lys Ala Ala Ala Glu Arg Gly Val<br>130                135               140 | 432 |
| caa acc atc atc tct tta caa ggt cgt aaa tca cca tat att ttg aga<br>Gln Thr Ile Ile Ser Leu Gln Gly Arg Lys Ser Pro Tyr Ile Leu Arg<br>145                150               155              160 | 480 |
| gca aaa gaa tta ata tct caa ggc tat atc ggc gac att aat tcg atc<br>Ala Lys Glu Leu Ile Ser Gln Gly Tyr Ile Gly Asp Ile Asn Ser Ile<br>                165               170              175 | 528 |
| gag att gct gga aat ggc ggt tgg tac ggc tac gaa agg cct gtt aaa<br>Glu Ile Ala Gly Asn Gly Gly Trp Tyr Gly Tyr Glu Arg Pro Val Lys<br>                    180               185              190 | 576 |
| tca cca aaa tac atc tat gaa atc ggg aac ggt gta gat ctg gta acc<br>Ser Pro Lys Tyr Ile Tyr Glu Ile Gly Asn Gly Val Asp Leu Val Thr<br>                        195               200              205 | 624 |
| aca aca ttt ggt cac aca atc gat att tta caa tac atg aca agt tcg<br>Thr Thr Phe Gly His Thr Ile Asp Ile Leu Gln Tyr Met Thr Ser Ser<br>        210                215               220 | 672 |
| tac ttt tcc agg ata aat gca atg gtt ttc aat aat att cca gag caa<br>Tyr Phe Ser Arg Ile Asn Ala Met Val Phe Asn Asn Ile Pro Glu Gln<br>225                230               235              240 | 720 |
| gag ctg ata gat gag cgt ggt aac cga ttg ggc cag cga gtc cca aag<br>Glu Leu Ile Asp Glu Arg Gly Asn Arg Leu Gly Gln Arg Val Pro Lys<br>                        245               250              255 | 768 |
| aca gta ccg gat cat ctt tta ttc caa ggc aca ttg tta aat ggc aat<br>Thr Val Pro Asp His Leu Leu Phe Gln Gly Thr Leu Leu Asn Gly Asn<br>            260               265              270 | 816 |
| gtt cca gtg tca tgc agt ttc aaa ggt ggc aaa cct acc aaa aaa ttt<br>Val Pro Val Ser Cys Ser Phe Lys Gly Gly Lys Pro Thr Lys Lys Phe<br>                275               280              285 | 864 |
| acc aaa aat ttg gtc att gac att cac ggt acc aag gga gat ttg aaa<br>Thr Lys Asn Leu Val Ile Asp Ile His Gly Thr Lys Gly Asp Leu Lys<br>290                295               300 | 912 |
| ctt gaa ggc gat gcc ggc ttc gca gaa att tca aat ctg gtc ctt tac<br>Leu Glu Gly Asp Ala Gly Phe Ala Glu Ile Ser Asn Leu Val Leu Tyr<br>305                310               315              320 | 960 |
| tac agt gga act aga gca aac gac ttc ccg cta gcc aat gga caa caa<br>Tyr Ser Gly Thr Arg Ala Asn Asp Phe Pro Leu Ala Asn Gly Gln Gln<br>                        325               330              335 | 1008 |
| gct cct tta gac ccg ggg tat gat gca ggt aaa gaa atc atg gaa gta<br>Ala Pro Leu Asp Pro Gly Tyr Asp Ala Gly Lys Glu Ile Met Glu Val<br>                  340               345              350 | 1056 |
| tat cat tta cga aat tat aat gcc att gtg ggt aat att cat cga ctg<br>Tyr His Leu Arg Asn Tyr Asn Ala Ile Val Gly Asn Ile His Arg Leu<br>                        355               360              365 | 1104 |
| tat caa tct atc tct gac ttc cac ttc aat aca aag aaa att cct gaa<br>Tyr Gln Ser Ile Ser Asp Phe His Phe Asn Thr Lys Lys Ile Pro Glu<br>370                375               380 | 1152 |
| tta ccc tca caa ttt gta atg caa ggt ttc gat ttc gaa ggc ttt ccc<br>Leu Pro Ser Gln Phe Val Met Gln Gly Phe Asp Phe Glu Gly Phe Pro<br>385                390               395              400 | 1200 |
| acc ttg atg gat gct ctg ata tta cac agg tta atc gag agc gtt tat<br>Thr Leu Met Asp Ala Leu Ile Leu His Arg Leu Ile Glu Ser Val Tyr<br>                        405               410              415 | 1248 |

```
aaa agt aac atg atg ggc tcc aca tta aac gtt agc aat atc tcg cat    1296
Lys Ser Asn Met Met Gly Ser Thr Leu Asn Val Ser Asn Ile Ser His
            420                 425                 430 tat agt tta                                                        1305
Tyr Ser Leu
        435

<210> SEQ ID NO 14
<211> LENGTH: 435
<212> TYPE: PRT
<213> ORGANISM: Saccharomyces cerevisiae

<400> SEQUENCE: 14

Met Asp Tyr Asn Lys Arg Ser Ser Val Ser Thr Val Pro Asn Ala Ala
1               5                   10                  15

Pro Ile Arg Val Gly Phe Val Gly Leu Asn Ala Ala Lys Gly Trp Ala
            20                  25                  30

Ile Lys Thr His Tyr Pro Ala Ile Leu Gln Leu Ser Ser Gln Phe Gln
        35                  40                  45

Ile Thr Ala Leu Tyr Ser Pro Lys Ile Glu Thr Ser Ile Ala Thr Ile
    50                  55                  60

Gln Arg Leu Lys Leu Ser Asn Ala Thr Ala Phe Pro Thr Leu Glu Ser
65                  70                  75                  80

Phe Ala Ser Ser Thr Ile Asp Met Ile Val Ile Ala Ile Gln Val
                85                  90                  95

Ala Ser His Tyr Glu Val Val Met Pro Leu Leu Glu Phe Ser Lys Asn
            100                 105                 110

Asn Pro Asn Leu Lys Tyr Leu Phe Val Glu Trp Ala Leu Ala Cys Ser
        115                 120                 125

Leu Asp Gln Ala Glu Ser Ile Tyr Lys Ala Ala Glu Arg Gly Val
130                 135                 140

Gln Thr Ile Ile Ser Leu Gln Gly Arg Lys Ser Pro Tyr Ile Leu Arg
145                 150                 155                 160

Ala Lys Glu Leu Ile Ser Gln Gly Tyr Ile Gly Asp Ile Asn Ser Ile
                165                 170                 175

Glu Ile Ala Gly Asn Gly Gly Trp Tyr Gly Tyr Glu Arg Pro Val Lys
            180                 185                 190

Ser Pro Lys Tyr Ile Tyr Glu Ile Gly Asn Gly Val Asp Leu Val Thr
        195                 200                 205

Thr Thr Phe Gly His Thr Ile Asp Ile Leu Gln Tyr Met Thr Ser Ser
210                 215                 220

Tyr Phe Ser Arg Ile Asn Ala Met Val Phe Asn Asn Ile Pro Glu Gln
225                 230                 235                 240

Glu Leu Ile Asp Glu Arg Gly Asn Arg Leu Gly Gln Arg Val Pro Lys
                245                 250                 255

Thr Val Pro Asp His Leu Leu Phe Gln Gly Thr Leu Leu Asn Gly Asn
            260                 265                 270

Val Pro Val Ser Cys Ser Phe Lys Gly Gly Lys Pro Thr Lys Lys Phe
        275                 280                 285

Thr Lys Asn Leu Val Ile Asp Ile His Gly Thr Lys Gly Asp Leu Lys
290                 295                 300

Leu Glu Gly Asp Ala Gly Phe Ala Glu Ile Ser Asn Leu Val Leu Tyr
305                 310                 315                 320

Tyr Ser Gly Thr Arg Ala Asn Asp Phe Pro Leu Ala Asn Gly Gln Gln
                325                 330                 335
```

```
Ala Pro Leu Asp Pro Gly Tyr Asp Ala Gly Lys Glu Ile Met Glu Val
            340                 345                 350

Tyr His Leu Arg Asn Tyr Asn Ala Ile Val Gly Asn Ile His Arg Leu
            355                 360                 365

Tyr Gln Ser Ile Ser Asp Phe His Phe Asn Thr Lys Lys Ile Pro Glu
        370                 375                 380

Leu Pro Ser Gln Phe Val Met Gln Gly Phe Asp Phe Glu Gly Phe Pro
385                 390                 395                 400

Thr Leu Met Asp Ala Leu Ile Leu His Arg Leu Ile Glu Ser Val Tyr
                405                 410                 415

Lys Ser Asn Met Met Gly Ser Thr Leu Asn Val Ser Asn Ile Ser His
                420                 425                 430

Tyr Ser Leu
        435

<210> SEQ ID NO 15
<211> LENGTH: 1230
<212> TYPE: DNA
<213> ORGANISM: Lipomyces starkeyi
<220> FEATURE:
<221> NAME/KEY: CDS
<222> LOCATION: (1)..(1230)

<400> SEQUENCE: 15 atg agt gag aag gca gag atc gag gtt ccg ccg caa aaa tcg aca ttc      48
Met Ser Glu Lys Ala Glu Ile Glu Val Pro Pro Gln Lys Ser Thr Phe
1               5                   10                  15 cct cgc agt gtg cac ttc gct cca ctt cat att cca ctg gag aga cgc      96
Pro Arg Ser Val His Phe Ala Pro Leu His Ile Pro Leu Glu Arg Arg
            20                  25                  30 cta cag act ttg gca gtc tta ttc cac act gtc gcg cta cca tac tgc     144
Leu Gln Thr Leu Ala Val Leu Phe His Thr Val Ala Leu Pro Tyr Cys
        35                  40                  45 atc ggt ctg ttc ttt ctc atg ctc gcg ttc cct cct ttt tgg cca tta     192
Ile Gly Leu Phe Phe Leu Met Leu Ala Phe Pro Pro Phe Trp Pro Leu
    50                  55                  60 ttg gta atg tat gtc ata tac gca tac ggg ttc gac cac tcg agc tcg     240
Leu Val Met Tyr Val Ile Tyr Ala Tyr Gly Phe Asp His Ser Ser Ser
65                  70                  75                  80 aac gga gag atc tcc cgc cgg cga tcg ccg ctg ttt cga aga ctc ccg     288
Asn Gly Glu Ile Ser Arg Arg Arg Ser Pro Leu Phe Arg Arg Leu Pro
                85                  90                  95 ttg ttc agg ctg tat tgt gat tac ttc ccc atc cac att cac cgg gag     336
Leu Phe Arg Leu Tyr Cys Asp Tyr Phe Pro Ile His Ile His Arg Glu
            100                 105                 110 gtt ccg ctc gag ccg acg ttt cct ggt cgc ctt cgc gaa ccg agt ggc     384
Val Pro Leu Glu Pro Thr Phe Pro Gly Arg Leu Arg Glu Pro Ser Gly
        115                 120                 125 ctt gtc gag cgg tgg att gcg aag atg ttc ggc gtg cag gac gct gtt     432
Leu Val Glu Arg Trp Ile Ala Lys Met Phe Gly Val Gln Asp Ala Val
    130                 135                 140 gtc gag gga aat gaa tct gac gtt aag gcc acg gcc aac ggc aat ggg     480
Val Glu Gly Asn Glu Ser Asp Val Lys Ala Thr Ala Asn Gly Asn Gly
145                 150                 155                 160 acg acg aaa gaa atc gga ccg acg tat gtt ttc ggc tat cat ccg cat     528
Thr Thr Lys Glu Ile Gly Pro Thr Tyr Val Phe Gly Tyr His Pro His
                165                 170                 175 gga att gtt agc ttg ggt gcg ttt ggt gct att ggt acg gaa ggc gct     576
Gly Ile Val Ser Leu Gly Ala Phe Gly Ala Ile Gly Thr Glu Gly Ala
```

```
                    180                 185                 190
gga tgg gag aag ctc ttt cct ggg atc ccg gtg tca ctg ctg act ctc     624
Gly Trp Glu Lys Leu Phe Pro Gly Ile Pro Val Ser Leu Leu Thr Leu
            195                 200                 205 gaa aca aat ttc agc ctt cca ttt tac aga gag tat ttg ctg tca ctt     672
Glu Thr Asn Phe Ser Leu Pro Phe Tyr Arg Glu Tyr Leu Leu Ser Leu
    210                 215                 220 ggg att gct tca gta tct cga cgg tct tgt acc aat ctc ctc aaa cac     720
Gly Ile Ala Ser Val Ser Arg Arg Ser Cys Thr Asn Leu Leu Lys His
225                 230                 235                 240 gac caa tcc atc tgc atc gtt atc ggc ggc gcc caa gag tcg ctc tta     768
Asp Gln Ser Ile Cys Ile Val Ile Gly Gly Ala Gln Glu Ser Leu Leu
                245                 250                 255 gcg gaa cca ggc act cta gat ctg atc ctc gtt aaa cgt cgc ggt ttt     816
Ala Glu Pro Gly Thr Leu Asp Leu Ile Leu Val Lys Arg Arg Gly Phe
            260                 265                 270 gtc aaa ctt gca atg tca acg gcg cgg gta tct gac caa ccg att tgt     864
Val Lys Leu Ala Met Ser Thr Ala Arg Val Ser Asp Gln Pro Ile Cys
    275                 280                 285 ctt gtt ccg atc ctc agt ttc ggc gag aac gac gtg tac gac caa gtc     912
Leu Val Pro Ile Leu Ser Phe Gly Glu Asn Asp Val Tyr Asp Gln Val
290                 295                 300 cgc ggg gac cga tcg tcg aag ttg tat aag atc cag act ttt atc aag     960
Arg Gly Asp Arg Ser Ser Lys Leu Tyr Lys Ile Gln Thr Phe Ile Lys
305                 310                 315                 320 aaa gcg gcc ggg ttt acg cta cca ttg atg tat gcg cgc ggt ata ttt    1008
Lys Ala Ala Gly Phe Thr Leu Pro Leu Met Tyr Ala Arg Gly Ile Phe
                325                 330                 335 aat tac gac ttt ggg ctg atg ccg tac cgc agg caa atg acg ctc gtg    1056
Asn Tyr Asp Phe Gly Leu Met Pro Tyr Arg Arg Gln Met Thr Leu Val
            340                 345                 350 gtc ggc aag ccg att gca gtg ccg tac gtg gcc cag cct acg gag gct    1104
Val Gly Lys Pro Ile Ala Val Pro Tyr Val Ala Gln Pro Thr Glu Ala
    355                 360                 365 gaa atc gaa gtg tat cac aag cag tac atg gat gaa ttg agg agg tta    1152
Glu Ile Glu Val Tyr His Lys Gln Tyr Met Asp Glu Leu Arg Arg Leu
370                 375                 380 tgg gac acg tat aag gac gac tat ttt gta gac cac aag ggc aag ggg    1200
Trp Asp Thr Tyr Lys Asp Asp Tyr Phe Val Asp His Lys Gly Lys Gly
385                 390                 395                 400 gtc aag aat tcc gag atg cgt ttt gtg gag                            1230
Val Lys Asn Ser Glu Met Arg Phe Val Glu
                405                 410

<210> SEQ ID NO 16
<211> LENGTH: 410
<212> TYPE: PRT
<213> ORGANISM: Lipomyces starkeyi

<400> SEQUENCE: 16

Met Ser Glu Lys Ala Glu Ile Glu Val Pro Pro Gln Lys Ser Thr Phe
1               5                   10                  15

Pro Arg Ser Val His Phe Ala Pro Leu His Ile Pro Leu Glu Arg Arg
            20                  25                  30

Leu Gln Thr Leu Ala Val Leu Phe His Thr Val Ala Leu Pro Tyr Cys
        35                  40                  45

Ile Gly Leu Phe Phe Leu Met Leu Ala Phe Pro Pro Phe Trp Pro Leu
    50                  55                  60

Leu Val Met Tyr Val Ile Tyr Ala Tyr Gly Phe Asp His Ser Ser Ser
```

```
                65                  70                  75                  80
        Asn Gly Glu Ile Ser Arg Arg Ser Pro Leu Phe Arg Arg Leu Pro
                            85                  90                  95

Leu Phe Arg Leu Tyr Cys Asp Tyr Phe Pro Ile His Ile His Arg Glu
                        100                 105                 110

Val Pro Leu Glu Pro Thr Phe Pro Gly Arg Leu Arg Glu Pro Ser Gly
                    115                 120                 125

Leu Val Glu Arg Trp Ile Ala Lys Met Phe Gly Val Gln Asp Ala Val
                130                 135                 140

Val Glu Gly Asn Glu Ser Asp Val Lys Ala Thr Ala Asn Gly Asn Gly
        145                 150                 155                 160

Thr Thr Lys Glu Ile Gly Pro Thr Tyr Val Phe Gly Tyr His Pro His
                        165                 170                 175

Gly Ile Val Ser Leu Gly Ala Phe Gly Ala Ile Gly Thr Glu Gly Ala
                    180                 185                 190

Gly Trp Glu Lys Leu Phe Pro Gly Ile Pro Val Ser Leu Leu Thr Leu
                195                 200                 205

Glu Thr Asn Phe Ser Leu Pro Phe Tyr Arg Glu Tyr Leu Leu Ser Leu
            210                 215                 220

Gly Ile Ala Ser Val Ser Arg Arg Ser Cys Thr Asn Leu Leu Lys His
        225                 230                 235                 240

Asp Gln Ser Ile Cys Ile Val Ile Gly Gly Ala Gln Glu Ser Leu Leu
                        245                 250                 255

Ala Glu Pro Gly Thr Leu Asp Leu Ile Leu Val Lys Arg Arg Gly Phe
                    260                 265                 270

Val Lys Leu Ala Met Ser Thr Ala Arg Val Ser Asp Gln Pro Ile Cys
                275                 280                 285

Leu Val Pro Ile Leu Ser Phe Gly Glu Asn Asp Val Tyr Asp Gln Val
            290                 295                 300

Arg Gly Asp Arg Ser Ser Lys Leu Tyr Lys Ile Gln Thr Phe Ile Lys
        305                 310                 315                 320

Lys Ala Ala Gly Phe Thr Leu Pro Leu Met Tyr Ala Arg Gly Ile Phe
                        325                 330                 335

Asn Tyr Asp Phe Gly Leu Met Pro Tyr Arg Arg Gln Met Thr Leu Val
                    340                 345                 350

Val Gly Lys Pro Ile Ala Val Pro Tyr Val Ala Gln Pro Thr Glu Ala
                355                 360                 365

Glu Ile Glu Val Tyr His Lys Gln Tyr Met Asp Glu Leu Arg Arg Leu
            370                 375                 380

Trp Asp Thr Tyr Lys Asp Asp Tyr Phe Val Asp His Lys Gly Lys Gly
        385                 390                 395                 400

Val Lys Asn Ser Glu Met Arg Phe Val Glu
                        405                 410

<210> SEQ ID NO 17
<211> LENGTH: 1254
<212> TYPE: DNA
<213> ORGANISM: Saccharomyces cerevisiae
<220> FEATURE:
<221> NAME/KEY: CDS
<222> LOCATION: (1)..(1254)

<400> SEQUENCE: 17 atg tca gga aca ttc aat gat ata aga aga agg aag aag gaa gaa gga        48
Met Ser Gly Thr Phe Asn Asp Ile Arg Arg Arg Lys Lys Glu Glu Gly
1               5                   10                  15
```

```
agc cct aca gcc ggt att acc gaa agg cat gag aat aag tct ttg tca    96
Ser Pro Thr Ala Gly Ile Thr Glu Arg His Glu Asn Lys Ser Leu Ser
        20                  25                  30 agc atc gat aaa aga gaa cag act ctc aaa cca caa cta gag tca tgc    144
Ser Ile Asp Lys Arg Glu Gln Thr Leu Lys Pro Gln Leu Glu Ser Cys
    35                  40                  45 tgt cca ttg gcg acc cct ttt gaa aga agg tta caa act ctg gct gta    192
Cys Pro Leu Ala Thr Pro Phe Glu Arg Arg Leu Gln Thr Leu Ala Val
50                  55                  60 gca tgg cac act tct tca ttt gta ctc ttc tcc ata ttt acg tta ttt    240
Ala Trp His Thr Ser Ser Phe Val Leu Phe Ser Ile Phe Thr Leu Phe
65                  70                  75                  80 gca atc tcg aca cca gca ctg tgg gtt ctt gct att cca tat atg att    288
Ala Ile Ser Thr Pro Ala Leu Trp Val Leu Ala Ile Pro Tyr Met Ile
                85                  90                  95 tat ttt ttt ttc gat agg tct cct gca act ggc gaa gtg gta aat cga    336
Tyr Phe Phe Phe Asp Arg Ser Pro Ala Thr Gly Glu Val Val Asn Arg
            100                 105                 110 tac tct ctt cga ttt cgt tca ttg ccc att tgg aag tgg tat tgt gat    384
Tyr Ser Leu Arg Phe Arg Ser Leu Pro Ile Trp Lys Trp Tyr Cys Asp
        115                 120                 125 tat ttc cct ata agt ttg att aaa act gtc aat tta aaa cca act ttt    432
Tyr Phe Pro Ile Ser Leu Ile Lys Thr Val Asn Leu Lys Pro Thr Phe
    130                 135                 140 acg ctt tca aaa aat aag aga gtt aac gaa aaa aat tac aag att aga    480
Thr Leu Ser Lys Asn Lys Arg Val Asn Glu Lys Asn Tyr Lys Ile Arg
145                 150                 155                 160 ttg tgg cca act aag tat tcc att aat ctc aaa agc aac tct act att    528
Leu Trp Pro Thr Lys Tyr Ser Ile Asn Leu Lys Ser Asn Ser Thr Ile
                165                 170                 175 gac tat cgc aac cag gaa tgt aca ggg cca acg tac tta ttt ggt tac    576
Asp Tyr Arg Asn Gln Glu Cys Thr Gly Pro Thr Tyr Leu Phe Gly Tyr
            180                 185                 190 cat cca cac ggc ata gga gca ctt ggt gcg ttt gga gcg ttt gca aca    624
His Pro His Gly Ile Gly Ala Leu Gly Ala Phe Gly Ala Phe Ala Thr
        195                 200                 205 gaa ggt tgt aac tat tcc aag att ttc cca ggt att cct att tct ctg    672
Glu Gly Cys Asn Tyr Ser Lys Ile Phe Pro Gly Ile Pro Ile Ser Leu
    210                 215                 220 atg aca ctg gtc aca caa ttt cat atc cca ttg tat aga gac tac tta    720
Met Thr Leu Val Thr Gln Phe His Ile Pro Leu Tyr Arg Asp Tyr Leu
225                 230                 235                 240 ttg gcg tta ggt att tct tca gta tct cgg aaa aac gct tta agg act    768
Leu Ala Leu Gly Ile Ser Ser Val Ser Arg Lys Asn Ala Leu Arg Thr
                245                 250                 255 cta agc aaa aat cag tcg atc tgc att gtt gtt ggt ggc gct agg gaa    816
Leu Ser Lys Asn Gln Ser Ile Cys Ile Val Val Gly Gly Ala Arg Glu
            260                 265                 270 tct tta tta agt tca aca aat ggt aca caa ctg att tta aac aaa aga    864
Ser Leu Leu Ser Ser Thr Asn Gly Thr Gln Leu Ile Leu Asn Lys Arg
        275                 280                 285 aag ggt ttt att aaa ctg gcc att caa acg ggg aat att aac cta gtg    912
Lys Gly Phe Ile Lys Leu Ala Ile Gln Thr Gly Asn Ile Asn Leu Val
    290                 295                 300 cct gtg ttt gca ttt gga gag gtg gac tgt tat aat gtt ctg agc aca    960
Pro Val Phe Ala Phe Gly Glu Val Asp Cys Tyr Asn Val Leu Ser Thr
305                 310                 315                 320 aaa aaa gat tca gtc ctg ggt aaa atg caa cta tgg ttc aaa gaa aac    1008
Lys Lys Asp Ser Val Leu Gly Lys Met Gln Leu Trp Phe Lys Glu Asn
```

-continued

```
                    325                 330                 335
ttt ggt ttt acc att ccc att ttc tac gca aga gga tta ttc aat tac    1056
Phe Gly Phe Thr Ile Pro Ile Phe Tyr Ala Arg Gly Leu Phe Asn Tyr
            340                 345                 350 gat ttc ggt ttg ttg cca ttt aga gcg cct atc aat gtt gtt gtt gga    1104
Asp Phe Gly Leu Leu Pro Phe Arg Ala Pro Ile Asn Val Val Val Gly
                355                 360                 365 agg cct ata tac gtt gaa aag aaa ata aca aat ccg cca gat gat gtt    1152
Arg Pro Ile Tyr Val Glu Lys Lys Ile Thr Asn Pro Pro Asp Asp Val
370                 375                 380 gtt aat cat ttc cat gat ttg tat att gcg gag ttg aaa aga cta tat    1200
Val Asn His Phe His Asp Leu Tyr Ile Ala Glu Leu Lys Arg Leu Tyr
385                 390                 395                 400 tac gaa aat aga gaa aaa tat ggg gta ccg gat gca gaa ttg aag ata    1248
Tyr Glu Asn Arg Glu Lys Tyr Gly Val Pro Asp Ala Glu Leu Lys Ile
                405                 410                 415 gtt ggg                                                             1254
Val Gly
```

<210> SEQ ID NO 18
<211> LENGTH: 418
<212> TYPE: PRT
<213> ORGANISM: Saccharomyces cerevisiae

<400> SEQUENCE: 18

```
Met Ser Gly Thr Phe Asn Asp Ile Arg Arg Arg Lys Lys Glu Glu Gly
1               5                   10                  15

Ser Pro Thr Ala Gly Ile Thr Glu Arg His Glu Asn Lys Ser Leu Ser
            20                  25                  30

Ser Ile Asp Lys Arg Glu Gln Thr Leu Lys Pro Gln Leu Glu Ser Cys
        35                  40                  45

Cys Pro Leu Ala Thr Pro Phe Glu Arg Arg Leu Gln Thr Leu Ala Val
    50                  55                  60

Ala Trp His Thr Ser Ser Phe Val Leu Phe Ser Ile Phe Thr Leu Phe
65                  70                  75                  80

Ala Ile Ser Thr Pro Ala Leu Trp Val Leu Ala Ile Pro Tyr Met Ile
                85                  90                  95

Tyr Phe Phe Phe Asp Arg Ser Pro Ala Thr Gly Glu Val Val Asn Arg
            100                 105                 110

Tyr Ser Leu Arg Phe Arg Ser Leu Pro Ile Trp Lys Trp Tyr Cys Asp
        115                 120                 125

Tyr Phe Pro Ile Ser Leu Ile Lys Thr Val Asn Leu Lys Pro Thr Phe
    130                 135                 140

Thr Leu Ser Lys Asn Lys Arg Val Asn Glu Lys Asn Tyr Lys Ile Arg
145                 150                 155                 160

Leu Trp Pro Thr Lys Tyr Ser Ile Asn Leu Lys Ser Asn Ser Thr Ile
                165                 170                 175

Asp Tyr Arg Asn Gln Glu Cys Thr Gly Pro Thr Tyr Leu Phe Gly Tyr
            180                 185                 190

His Pro His Gly Ile Gly Ala Leu Gly Ala Phe Gly Ala Phe Ala Thr
        195                 200                 205

Glu Gly Cys Asn Tyr Ser Lys Ile Phe Pro Gly Ile Pro Ile Ser Leu
    210                 215                 220

Met Thr Leu Val Thr Gln Phe His Ile Pro Leu Tyr Arg Asp Tyr Leu
225                 230                 235                 240

Leu Ala Leu Gly Ile Ser Ser Val Ser Arg Lys Asn Ala Leu Arg Thr
```

```
                    245                 250                 255
Leu Ser Lys Asn Gln Ser Ile Cys Ile Val Val Gly Gly Ala Arg Glu
            260                 265                 270

Ser Leu Leu Ser Ser Thr Asn Gly Thr Gln Leu Ile Leu Asn Lys Arg
        275                 280                 285

Lys Gly Phe Ile Lys Leu Ala Ile Gln Thr Gly Asn Ile Asn Leu Val
290                 295                 300

Pro Val Phe Ala Phe Gly Glu Val Asp Cys Tyr Asn Val Leu Ser Thr
305                 310                 315                 320

Lys Lys Asp Ser Val Leu Gly Lys Met Gln Leu Trp Phe Lys Glu Asn
            325                 330                 335

Phe Gly Phe Thr Ile Pro Ile Phe Tyr Ala Arg Gly Leu Phe Asn Tyr
        340                 345                 350

Asp Phe Gly Leu Leu Pro Phe Arg Ala Pro Ile Asn Val Val Val Gly
                355                 360                 365

Arg Pro Ile Tyr Val Glu Lys Lys Ile Thr Asn Pro Pro Asp Asp Val
    370                 375                 380

Val Asn His Phe His Asp Leu Tyr Ile Ala Glu Leu Lys Arg Leu Tyr
385                 390                 395                 400

Tyr Glu Asn Arg Glu Lys Tyr Gly Val Pro Asp Ala Glu Leu Lys Ile
                405                 410                 415

Val Gly

<210> SEQ ID NO 19
<211> LENGTH: 1512
<212> TYPE: DNA
<213> ORGANISM: Phaeodactylum tricornutum
<220> FEATURE:
<221> NAME/KEY: CDS
<222> LOCATION: (1)..(1512)

<400> SEQUENCE: 19 atg gat gtc ttt ggc agc aaa ttg gtt gaa gcg ctc tcc gtc tat cat      48
Met Asp Val Phe Gly Ser Lys Leu Val Glu Ala Leu Ser Val Tyr His
1               5                   10                  15 gct tcc tgg ctg ctt ggt tta agc gtc aca gta gcg gta gcg atc gca      96
Ala Ser Trp Leu Leu Gly Leu Ser Val Thr Val Ala Val Ala Ile Ala
                20                  25                  30 atc aaa atg tcc tcc aat caa aaa agt cgc tcg cct ctg cac cga aag     144
Ile Lys Met Ser Ser Asn Gln Lys Ser Arg Ser Pro Leu His Arg Lys
            35                  40                  45 ttt tct ttc aca tcc gtc gga atg gcc atc gga atc ttc ccc gaa tcg     192
Phe Ser Phe Thr Ser Val Gly Met Ala Ile Gly Ile Phe Pro Glu Ser
        50                  55                  60 gtc aaa gct ccc aca aca atc atc aac gcg gca atc tac ttt tca aca     240
Val Lys Ala Pro Thr Thr Ile Ile Asn Ala Ala Ile Tyr Phe Ser Thr
65                  70                  75                  80 tgt ccg gcc gag aag gat ctc att gaa ctg gcg gta aaa cct atg ctt     288
Cys Pro Ala Glu Lys Asp Leu Ile Glu Leu Ala Val Lys Pro Met Leu
                85                  90                  95 gct ttc acg cga ctg tca acg att cct gtc ccg gaa acg gcc aac tgc     336
Ala Phe Thr Arg Leu Ser Thr Ile Pro Val Pro Glu Thr Ala Asn Cys
            100                 105                 110 cga cct tcc acg cgg tct ttt gcg cca tcg gaa ctc att cgg aag gtt     384
Arg Pro Ser Thr Arg Ser Phe Ala Pro Ser Glu Leu Ile Arg Lys Val
        115                 120                 125 gaa ata tca ggt aaa tgc atc aag tcg aca aat gat gtc ata ttt aag     432
Glu Ile Ser Gly Lys Cys Ile Lys Ser Thr Asn Asp Val Ile Phe Lys
```

-continued

|  |  |  |  |  |  |  |  |  |  |  |  |  |  |  |  |
|--|--|--|--|--|--|--|--|--|--|--|--|--|--|--|--|
| 130 | | | | 135 | | | | 140 | | | | | | | |

```
cac ctg caa gag tcg ctc tcg aca gag cga gac gat ttg ccg tgg tgg      480
His Leu Gln Glu Ser Leu Ser Thr Glu Arg Asp Asp Leu Pro Trp Trp
145             150                 155                 160 gag ttt cta gtg gtc gaa aac gtt ggc gag ggc gag tct gcc gtc gtt      528
Glu Phe Leu Val Val Glu Asn Val Gly Glu Gly Glu Ser Ala Val Val
                165                 170                 175 cta cgg atg cac cac gcc cta gcg gat ggt att tcg cta gta cac gtt      576
Leu Arg Met His His Ala Leu Ala Asp Gly Ile Ser Leu Val His Val
            180                 185                 190 ttt gaa aag ttc ata acc tac gaa gat ggt tcg ccg gtt ttg tcc att      624
Phe Glu Lys Phe Ile Thr Tyr Glu Asp Gly Ser Pro Val Leu Ser Ile
        195                 200                 205 att ctg tcc aac atg gcg cag aag agc aaa gtc gag aaa acg cac aaa      672
Ile Leu Ser Asn Met Ala Gln Lys Ser Lys Val Glu Lys Thr His Lys
    210                 215                 220 aca aat ccc ttc cgc ctt gct tgg atg ctt gtc cga gat gct acc aag      720
Thr Asn Pro Phe Arg Leu Ala Trp Met Leu Val Arg Asp Ala Thr Lys
225                 230                 235                 240 gtc ctc acg ttg ggt ctt tcg cgt tcg gac gat ccc act atc ttt acc      768
Val Leu Thr Leu Gly Leu Ser Arg Ser Asp Asp Pro Thr Ile Phe Thr
                245                 250                 255 gaa ccg aat cag acg tat gtg cat tcg cag cat cga gaa tgt gtg gtt      816
Glu Pro Asn Gln Thr Tyr Val His Ser Gln His Arg Glu Cys Val Val
            260                 265                 270 ttc cca acg ttt tca ttg gcc ttc gtt aag cgg ctg aaa aca gca gcc      864
Phe Pro Thr Phe Ser Leu Ala Phe Val Lys Arg Leu Lys Thr Ala Ala
        275                 280                 285 aac gtg acc gtt aac gat att ctc atg acg gcc gtc agc caa gcg gta      912
Asn Val Thr Val Asn Asp Ile Leu Met Thr Ala Val Ser Gln Ala Val
    290                 295                 300 cac gag tac tgc cga gct gaa tcc tgc tcg gtc ttg atg gga aaa gga      960
His Glu Tyr Cys Arg Ala Glu Ser Cys Ser Val Leu Met Gly Lys Gly
305                 310                 315                 320 gca tcg ctt cag tca cgt gca tta ttg ccg ata gcg ttg ccg cga tcc     1008
Ala Ser Leu Gln Ser Arg Ala Leu Leu Pro Ile Ala Leu Pro Arg Ser
                325                 330                 335 gcg tca gac ttg gaa cat cct tcc acg gct ttg cgc aac aag tgg tgt     1056
Ala Ser Asp Leu Glu His Pro Ser Thr Ala Leu Arg Asn Lys Trp Cys
            340                 345                 350 ctt gtt tcg gca aat atg agc att ggc tgt gtc gac cta gtg gat cgt     1104
Leu Val Ser Ala Asn Met Ser Ile Gly Cys Val Asp Leu Val Asp Arg
        355                 360                 365 ctt aat tcg atc cac cag act act gtt cac tta aaa gga agc cca att     1152
Leu Asn Ser Ile His Gln Thr Thr Val His Leu Lys Gly Ser Pro Ile
    370                 375                 380 gcc atg gtc caa ctc agt ctg caa aac aaa ttg gca agt cga ttg cct     1200
Ala Met Val Gln Leu Ser Leu Gln Asn Lys Leu Ala Ser Arg Leu Pro
385                 390                 395                 400 aaa ata gtc gct cga caa acc atg ctg gac att ttt cga agg cat tcg     1248
Lys Ile Val Ala Arg Gln Thr Met Leu Asp Ile Phe Arg Arg His Ser
                405                 410                 415 ctt gtc ttt tcc aac gtt ccc ggc cca gat cgt ccg tgt caa ttg gcc     1296
Leu Val Phe Ser Asn Val Pro Gly Pro Asp Arg Pro Cys Gln Leu Ala
            420                 425                 430 ggg caa aca gcc act gga gta caa atg ttc tat agc aac ctg att cct     1344
Gly Gln Thr Ala Thr Gly Val Gln Met Phe Tyr Ser Asn Leu Ile Pro
        435                 440                 445 caa gtt gga ttg ctg tcg tac gcc ggg aac att tac ggt aat ata gtc     1392
```

```
Gln Val Gly Leu Leu Ser Tyr Ala Gly Asn Ile Tyr Gly Asn Ile Val
    450                 455                 460 cta gac act ggt gcc gtg ccc aac gct gaa tct ttg gct ggc cat tac      1440
Leu Asp Thr Gly Ala Val Pro Asn Ala Glu Ser Leu Ala Gly His Tyr
465                 470                 475                 480 gca aag gcg ctt gtc gac atg gcg acc ctg ctc aac gtc gac aaa att      1488
Ala Lys Ala Leu Val Asp Met Ala Thr Leu Leu Asn Val Asp Lys Ile
                485                 490                 495 cca acg aat tta cag tcg tac ttc                                      1512
Pro Thr Asn Leu Gln Ser Tyr Phe
            500
```

<210> SEQ ID NO 20
<211> LENGTH: 504
<212> TYPE: PRT
<213> ORGANISM: Phaeodactylum tricornutum

<400> SEQUENCE: 20

```
Met Asp Val Phe Gly Ser Lys Leu Val Glu Ala Leu Ser Val Tyr His
1               5                   10                  15

Ala Ser Trp Leu Leu Gly Leu Ser Val Thr Val Ala Val Ala Ile Ala
                20                  25                  30

Ile Lys Met Ser Ser Asn Gln Lys Ser Arg Ser Pro Leu His Arg Lys
            35                  40                  45

Phe Ser Phe Thr Ser Val Gly Met Ala Ile Gly Ile Phe Pro Glu Ser
    50                  55                  60

Val Lys Ala Pro Thr Thr Ile Ile Asn Ala Ala Ile Tyr Phe Ser Thr
65                  70                  75                  80

Cys Pro Ala Glu Lys Asp Leu Ile Glu Leu Ala Val Lys Pro Met Leu
                85                  90                  95

Ala Phe Thr Arg Leu Ser Thr Ile Pro Val Pro Glu Thr Ala Asn Cys
                100                 105                 110

Arg Pro Ser Thr Arg Ser Phe Ala Pro Ser Glu Leu Ile Arg Lys Val
            115                 120                 125

Glu Ile Ser Gly Lys Cys Ile Lys Ser Thr Asn Asp Val Ile Phe Lys
    130                 135                 140

His Leu Gln Glu Ser Leu Ser Thr Glu Arg Asp Asp Leu Pro Trp Trp
145                 150                 155                 160

Glu Phe Leu Val Val Glu Asn Val Gly Glu Gly Glu Ser Ala Val Val
                165                 170                 175

Leu Arg Met His His Ala Leu Ala Asp Gly Ile Ser Leu Val His Val
                180                 185                 190

Phe Glu Lys Phe Ile Thr Tyr Glu Asp Gly Ser Pro Val Leu Ser Ile
            195                 200                 205

Ile Leu Ser Asn Met Ala Gln Lys Ser Lys Val Glu Lys Thr His Lys
    210                 215                 220

Thr Asn Pro Phe Arg Leu Ala Trp Met Leu Val Arg Asp Ala Thr Lys
225                 230                 235                 240

Val Leu Thr Leu Gly Leu Ser Arg Ser Asp Asp Pro Thr Ile Phe Thr
                245                 250                 255

Glu Pro Asn Gln Thr Tyr Val His Ser Gln His Arg Glu Cys Val Val
                260                 265                 270

Phe Pro Thr Phe Ser Leu Ala Phe Val Lys Arg Leu Lys Thr Ala Ala
            275                 280                 285

Asn Val Thr Val Asn Asp Ile Leu Met Thr Ala Val Ser Gln Ala Val
    290                 295                 300
```

-continued

```
His Glu Tyr Cys Arg Ala Glu Ser Cys Ser Val Leu Met Gly Lys Gly
305                 310                 315                 320

Ala Ser Leu Gln Ser Arg Ala Leu Leu Pro Ile Ala Leu Pro Arg Ser
                325                 330                 335

Ala Ser Asp Leu Glu His Pro Ser Thr Ala Leu Arg Asn Lys Trp Cys
            340                 345                 350

Leu Val Ser Ala Asn Met Ser Ile Gly Cys Val Asp Leu Val Asp Arg
        355                 360                 365

Leu Asn Ser Ile His Gln Thr Thr Val His Leu Lys Gly Ser Pro Ile
    370                 375                 380

Ala Met Val Gln Leu Ser Leu Gln Asn Lys Leu Ala Ser Arg Leu Pro
385                 390                 395                 400

Lys Ile Val Ala Arg Gln Thr Met Leu Asp Ile Phe Arg Arg His Ser
                405                 410                 415

Leu Val Phe Ser Asn Val Pro Gly Pro Asp Arg Pro Cys Gln Leu Ala
            420                 425                 430

Gly Gln Thr Ala Thr Gly Val Gln Met Phe Tyr Ser Asn Leu Ile Pro
        435                 440                 445

Gln Val Gly Leu Leu Ser Tyr Ala Gly Asn Ile Tyr Gly Asn Ile Val
    450                 455                 460

Leu Asp Thr Gly Ala Val Pro Asn Ala Glu Ser Leu Ala Gly His Tyr
465                 470                 475                 480

Ala Lys Ala Leu Val Asp Met Ala Thr Leu Leu Asn Val Asp Lys Ile
                485                 490                 495

Pro Thr Asn Leu Gln Ser Tyr Phe
            500
```